(12) United States Patent
Delahaye et al.

(10) Patent No.: US 8,691,281 B2
(45) Date of Patent: Apr. 8, 2014

(54) SOLID PHARMACEUTICAL COMPOSITION CONTAINING 6-OXO-6,7,8,9,10,11-HEXAHYDROCYCLOHEPTA (C)CHROMEN-3-YL SULFAMATE AND POLYMORPHS THEREOF

(75) Inventors: Delphine Delahaye, Massy (FR); Christian Diolez, Palaiseau (FR); Alain Rolland, Palaiseau (FR); Francis Diancourt, Epernon (FR); Gérard Coquerel, Boos (FR); Damien Martins, Rouen (FR); Barry Victor Lloyd Potter, Bath (GB); Lok Wai Lawrence Woo, Bath (GB)

(73) Assignee: Ipsen Pharma S.A.S., Boulogne-Billancourt (FR)

( * ) Notice: Subject to any disclaimer, the term of this patent is extended or adjusted under 35 U.S.C. 154(b) by 0 days.

(21) Appl. No.: 13/430,523

(22) Filed: Mar. 26, 2012

(65) Prior Publication Data
US 2012/0321714 A1    Dec. 20, 2012

Related U.S. Application Data

(63) Continuation of application No. 13/201,614, filed as application No. PCT/FR2010/000117 on Feb. 12, 2010, now abandoned.

(30) Foreign Application Priority Data

Feb. 13, 2009    (FR) ...................................... 0900655
Feb. 13, 2009    (FR) ...................................... 0900656

(51) Int. Cl.
| | | |
|---|---|---|
| *A61K 9/14* | (2006.01) |
| *B32B 5/16* | (2006.01) |
| *B32B 9/00* | (2006.01) |
| *B32B 15/02* | (2006.01) |
| *B32B 17/02* | (2006.01) |
| *B32B 19/00* | (2006.01) |
| *B32B 21/02* | (2006.01) |
| *B32B 23/02* | (2006.01) |
| *B32B 27/02* | (2006.01) |
| *A01N 43/16* | (2006.01) |
| *A61K 31/35* | (2006.01) |

(52) U.S. Cl.
USPC ............................ 424/489; 428/402; 514/455

(58) Field of Classification Search
None
See application file for complete search history.

(56) References Cited

FOREIGN PATENT DOCUMENTS

| | | |
|---|---|---|
| CN | 1444940 | 10/2003 |
| CN | 1989961 | 7/2007 |
| EP | 0 880 514 | 4/2005 |
| WO | WO 2008065428 A2 * | 6/2008 |

OTHER PUBLICATIONS

Caira, Topics in Current Chemistry, vol. 198, pp. 163-208, XP001156954 (1998).
Foster et al., Breast Cancer Research and Treatment, Kluwer Academic Publishers, vol. 111, No. 1, pp. 129-138, XP019600734 (2007).
Foster et al., Endocrinology, vol. 149, No. 8, pp. 4035-4042, XP002597970 (2008).
Stanway et al., Clinical Cancer Research, The American Association for Cancer Research, vol. 12, No. 5, pp. 1585-1592, XP002479602 (2006).
Woo et al., Chemistry and Biology, Current Biology, vol. 7, No. 10, pp. 773-791, XP001055209 (2000).
International Search Report for International Application No. PCT/FR2010/000117, mailed Dec. 27, 2010.

* cited by examiner

*Primary Examiner* — Robert T Crow
*Assistant Examiner* — Doan Phan
(74) *Attorney, Agent, or Firm* — Hunton & Williams LLP

(57) ABSTRACT

The present invention relates to a solid pharmaceutical composition including the active principle 6-oxo-6,7,8,9,10,11-hexahydrocyclohepta[c]chromen-3-yl sulfamate. The present invention also relates to polymorphs of the 6-oxo-6,7,8,9,10,11-hexahydrocyclohepta[c]chromen-3-yl sulfamate compound.

15 Claims, 26 Drawing Sheets

Figure 3: Calculated X-ray diffraction diagram of the DMSO solvate of form 2 of compound 1

Figure 5: Calculated X-ray powder diffraction diagram of variety I of compound 1

Figure 8: IR spectrum of variety I of compound 1

Figure 9: NMR spectrum of the solid of variety I of compound 1

Figure 11: Experimental X-ray powder diffraction diagram of the DMSO solvate of compound 1

Figure 12: Calculated X-ray diffraction diagram of the DMSO solvate of form 3 of compound 1

Figure 13: Experimental X-ray powder diffraction diagram of the DMSO solvate of form 3 of compound 1

Figure 17: IR spectrum of polymorphic form III of compound 1

Figure 18: NMR spectrum of the solid of polymorphic form III of compound 1

Figure 20: Experimental X-ray powder diffraction diagram of 1,4-dioxane hemisolvate of compound 1

Figure 21: TG-DSC thermogram of 1,4-dioxane hemisolvate of compound 1

Figure 22: Experimental X-ray powder diffraction diagram of polymorphic form II of compound 1

Figure 23: DSC thermogram of polymorphic form II of compound 1

Figure 24: IR spectrum of polymorphic form II of compound 1

Figure 25: NMR spectrum of the solid of polymorphic form II of compound 1

SOLID PHARMACEUTICAL COMPOSITION CONTAINING 6-OXO-6,7,8,9,10,11-HEXAHYDROCYCLOHEPTA (C)CHROMEN-3-YL SULFAMATE AND POLYMORPHS THEREOF

This application is a Continuation of U.S. patent application Ser. No. 13/201,614, filed Aug. 15, 2011, which is a national stage of filing of PCT/FR2010/000117, filed Feb. 12, 2010, the subject matter of which is incorporated herein in its entirety. This application further claims priority to FR 0900655, filed Feb. 13, 2009, and FR 0900656, filed Feb. 13, 2009, the subject matter of which is incorporated herein in its entirety.

DETAILED DESCRIPTION OF THE INVENTION

The present invention relates to a solid pharmaceutical composition comprising as active ingredient the compound 6-oxo-6,7,8,9,10,11-hexahydrocyclohepta[c]chromen-3-yl sulphamate. The invention also relates to the preparation of this pharmaceutical composition, its use as a medicament, and more particularly as a medicament for the treatment of certain cancers, compound 1 targeting the enzyme steroid sulphatase.

A composition according to the invention, containing as active ingredient the compound 6-oxo-6,7,8,9,10,11-hexahydrocyclohepta[c]chromen-3-yl sulphamate (hereafter also called compound 1) has the advantage of being a stable oral pharmaceutical composition and offering appropriate bioavailability.

Compound 1, of structure:

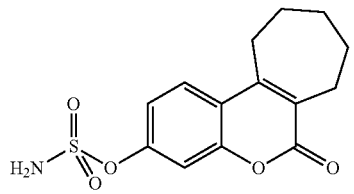 [SMILES: NS(=O)(=O)Oc1ccc2c3c(c(=O)oc2c1)CCCCC3]

is described in patent EP 880514. Nowadays, increasing attention is being paid to this compound for its sulphatase inhibiting activity and the therapeutic applications that this involves, as described by L. W. Woo, et al., in *Chemistry & Biology*, 2000, 7,773-91. The inhibition of the steroid-sulphatase (STS), the enzyme responsible for the hydrolysis of steroid sulphates, represents for example a promising novel treatment for postmenopausal patients with hormone-dependent breast cancer (*Clin. Cancer Res.* 2006; 12 (5).

As a general rule, the pharmaceutical compositions such as tablets can be produced according to three processes: wet granulation, dry granulation and direct compression.

Compound 1 belongs to Class 2 of the Biopharmaceutical Classification System or BCS proposed by G. Amidon (cf. G. L. Amidon et al., "A theoretical basis for a biopharmaceutical drug classification: the correlation of in vitro drug dissolution and in vivo bioavailability", Pharm. Res. 12 (1995) 413-420). Its absorption, and therefore its bioavailability, thus strongly depend on the dissolution rate of the pharmaceutical form administered.

The processes and formulations known from the prior art using aqueous phases, such as the self-emulsifying formulations ("Self-Emulsifying Drug Delivery Systems") used in a standard fashion in order to increase the solubility of the compounds of Class 2 are not suitable, as the excipients and the aqueous phases used are not compatible with compound 1, and lead to chemical degradations during the production stage.

Due to problems of stability and a low solubility of compound 1, it was difficult to obtain a formulation allowing the production of tablets which are sufficiently stable over time and comprising a sufficient concentration of active ingredient. Furthermore, the composition which was poorly compressible resulted in fragmentations during the dry pressing as well as too slow a dissolution profile. Due to the instability of compound 1 in the presence of water, being easily hydrolyzable, it was difficult to envisage a wet granulation process.

Unexpectedly, formulations making it possible to obtain dry oral forms of compound 1 by a wet granulation process have been obtained.

In the case of wet granulation, the components are mixed and granulated in wet phase by means of a binder. The binder can be either dissolved in the wet phase or incorporated in the mixture of powder to be granulated. The wet granules are then sieved, dried and optionally ground, before compression in order to form the tablets.

Unexpectedly, a novel solid pharmaceutical composition has been found, intended for the administration by oral route of compound 1, making it possible to solve the problems specific to this active ingredient and to obtain it by a wet granulation process.

This oral composition, in the form of a tablet or gelatin capsule, is stable with rapid dissolution of the solid form thus providing immediate release with effective bioavailability.

A subject of the present invention is therefore a solid pharmaceutical composition containing as active ingredient 6-oxo-6,7,8,9,10,11-hexahydrocyclohepta[c]chromen-3-yl sulphamate and at least one pharmaceutically acceptable excipient.

A subject of the present invention is also a solid pharmaceutical composition containing as active ingredient 6-oxo-6,7,8,9,10,11-hexahydrocyclohepta[c]chromen-3-yl sulphamate and at least one pharmaceutically acceptable excipient, for oral administration and preferably for oral administration with immediate release.

A subject of the present invention is also a solid pharmaceutical composition for administration by oral route comprising compound 1 as active ingredient and at least one disintegration agent as well as one or more agents protecting against moisture.

Such agents therefore protect the active ingredient against hydrolysis, thus preventing its degradation. Preferably, compound 1 is micronized.

It was observed that this degradation occurs mainly during the manufacture of the pharmaceutical composition and in particular during the wet granulation stage. Unexpectedly, it was shown that the addition of excipients, used for their properties as binders and diluents in the technical field considered, provided an effect of protecting the active ingredient.

A subject of the present invention is also the manufacturing process of the pharmaceutical compositions as described below. It is thus possible to carry out the process according to the invention using adjuvants and excipients of the standard type for the manufacture of the tablets using wet granulation.

By "oral administration with immediate release" or "oral form with immediate release" or also "composition with immediate release", is meant according to the invention an administration or oral composition allowing in vitro dissolution of at least 80% by weight of the active ingredient in 45 minutes, preferably in 30 minutes according to the appropriate in vitro dissolution test, developed for compound 1. This test is carried out with a paddle dissolution apparatus at 37° C. under stirring at 100 rpm, in a buffered hydrochloric acid solution at pH 1.2 according to the US Pharmacopeia standards, and comprising 0.1% a surfactant, cetyl trimethyl ammonium bromide, which makes it possible to obtain sufficient solubility of the active ingredient in the test medium. The assay is carried out by ultra-violet (UV)/visible absorption spectrophotometry at a wavelength of 311 nm.

By the term "gliding agents" or "flow agents" used according to the invention, is also meant the adjuvants and excipients sometimes called lubricants and agents improving the fluidity and flow of the granules.

By the term "centesimal formulation" is meant according to the invention a given proportion of active ingredient or excipient in % by weight, with respect to the total weight of the composition.

The term "binding agent" or binder denotes, according to the invention, adjuvants or excipients used to maintain the structure and cohesion of the galenic form. They have the property of allowing assembly in the form of granules of the ingredients during the granulation stage and ensuring the cohesion of the galenic form after compression.

The term "disintegration agent" denotes, according to the invention, excipients or adjuvants which can be added to the formulations in order to facilitate the disintegration of the tablets when they are found in a liquid environment, such as water or the gastric juices.

DESCRIPTION OF THE FIGURES

FIGS. 1 and 2 show the effect of the excipients as well as the in vitro behaviour of the solid composition.

Figure 1:
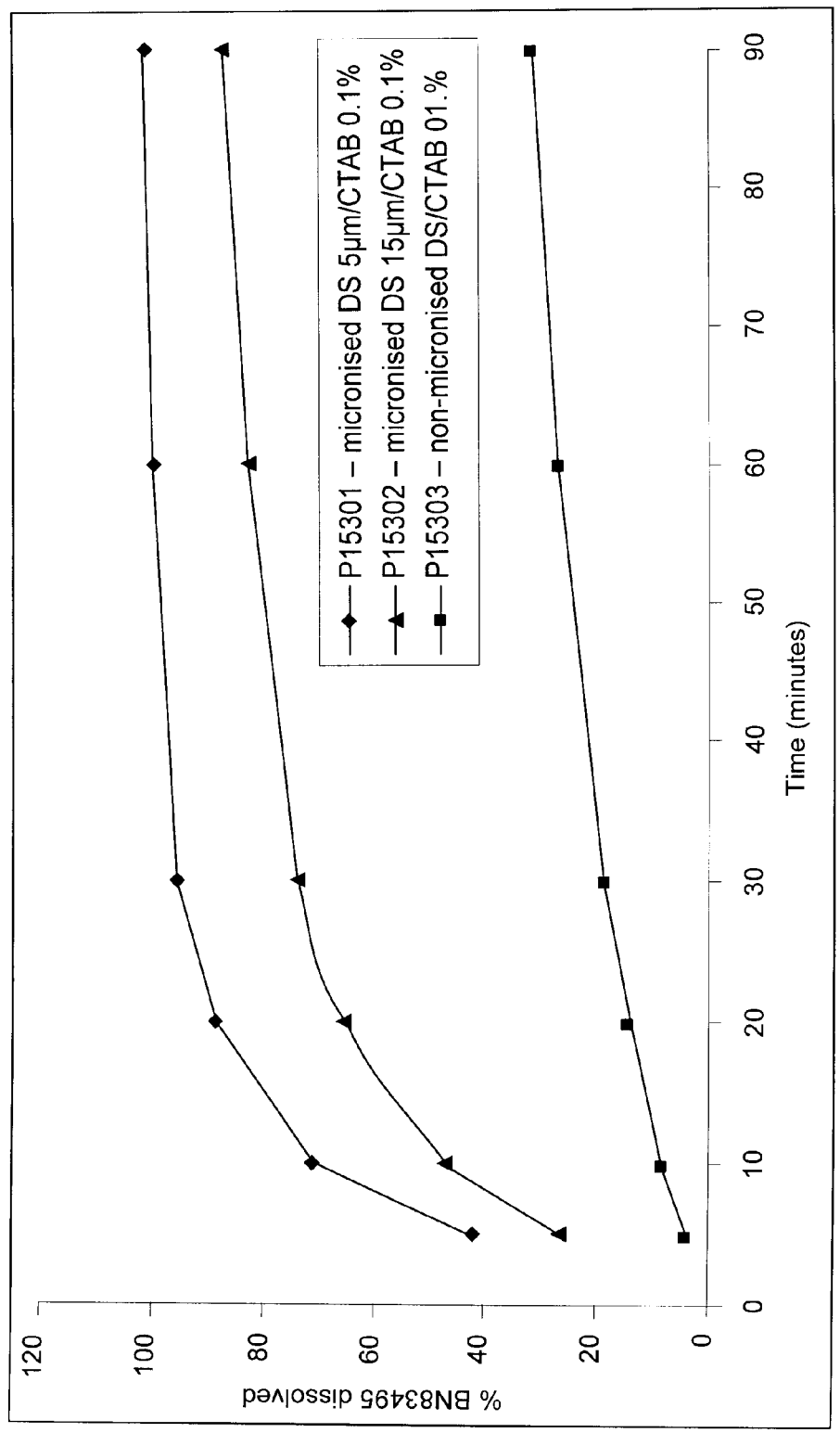
FIG. 1: shows the comparative dissolution curves of the composition of compound 1 as a function of time and the influence of the micronization of the active ingredient in the composition. Each curve corresponds to a solid composition comprising compound 1 with a different micronization.

The present invention exhibits numerous advantages, in particular the combination:
  of increased stability and
  of increased bioavailability linked to the immediate dissolution (at least 80% in 30 minutes) of the pharmaceutical form.

Preferably, the process used for the preparation of the tablet according to the invention passes through a wet granulation stage preceding the stage of formation of the tablet.

In fact, it was unexpectedly shown that, in spite of the low stability of compound 1 in aqueous phase, the tablet can be prepared by a process comprising a wet granulation stage. The production of the tablet according to this process benefits from a stabilization of compound 1 in aqueous phase in the presence of well-chosen excipients.

According to a first characteristic of the invention, compound 1 is obtained by an appropriate treatment in order to obtain a particle size comprised between 0.1 and 20 μm. Preferentially, compound 1 has a particle size comprised between 1 and 15 μm, and more preferentially between 2 and 10 μm. Even more preferentially compound 1 has a size of 5 μm±2 μm.

Pharmaceutically acceptable excipients appropriate for the manufacture of the pharmaceutical compositions of the invention can be, for example, maltodextrin, mannitol, microcrystalline cellulose, lactose, corn starch, sodium starch glycolate, croscarmellose sodium, partially cross-linked poly(N-vinyl-2-pyrrolidone) or crospovidone, polyvinylpyrrolidone, copolymers of N-vinyl-2-pyrrolidone and vinyl acetate (or copovidones) such as the copolymer Kollidon VA64, carboxymethylcellulose, pregelatinized starch, methylcellulose, polyethylene glycol, macrogols, polyglycols, polyoxyethylene, pyrrolidone-2, colloidal silica, talc, magnesium stearate, sodium stearyl fumarate, calcium stearate, hydrogenated vegetable oil, sodium lauryl sulphate, calcium phosphate, sugars, dextrin, starch, gelatin, cellulose, wax, or also water, organic solvents such as glycerol or the glycols, as well as mixtures thereof, in varying proportions, with or without water. These excipients, added to the active ingredient, have the function of being:
  diluents, such as for example mannitol, lactose or lactose monohydrate, starch, calcium carbonate, microcrystalline cellulose, or maltodextrin;
  disintegration agents, such as for example starch, croscarmellose sodium, sodium starch glycolate, or crospovidone;

binders, such as for example polyvinylpyrrolidone, copolymers of N-vinyl-2-pyrrolidone and vinyl acetate (or copovidones), carboxymethylcellulose, pregelatinized starch, or methylcellulose;

flow agents or gliding agent, such as for example colloidal silica, or talc;

lubricants, such as for example magnesium stearate, sodium stearyl fumarate, calcium stearate, stearic acid or hydrogenated vegetable oil;

solubilizing agents, such as macrogol (polyethylene glycol), polyglycol, polyoxyethylene glycol, polydiol, pyrrolidone-2, or polyvinylpyrrolidone;

surfactants (or surface active agents) such as sodium lauryl sulphate.

A subject of the present invention is also a solid pharmaceutical composition for administration by oral route of compound 1 as active ingredient, characterized in that it comprises compound 1 and at least one disintegration agent, one or more diluents and one or more binders. Preferably, the compound is micronized.

Preferably, the pharmaceutical composition according to the invention, in the solid form for oral administration, is a gelatin capsule. Preferably, the pharmaceutical composition according to the invention, in the solid form for oral administration, is a tablet.

In the compositions below, each type of excipient can be alone or in a mixture. Thus "x % of a binder" means x % of a binder alone or of a mixture of binders.

The composition according to the invention, can be formulated in a gelatin capsule according to a centesimal formulation containing: 1 to 30% active ingredient, preferably 5 to 20%; 40 to 92% diluent, preferably 65 to 92%, very preferentially 75 to 90%; 0 to 10% binder, preferably, 0 to 8%; 0 to 30% disintegration agent, preferably 0 to 20%; 0 to 5% surfactant, preferably 0%; 0 to 5% solubilizing agent, preferably 0%; 0.1 to 3% flow agent, preferably 0.9 to 1.4%; 0.5 to 3% lubricant, preferably 0.6 to 2.8%.

Preferentially, the pharmaceutical composition as defined above is a gelatin capsule; and more preferentially a gelatin capsule of centesimal formulation comprising 5 to 30% active ingredient; 40 to 92% diluent; 0 to 8% binder, preferably 0 to 5%; 0 to 30% disintegration agent; 0 to 5% surfactant; 0 to 5% solubilizing agent; 0.1 to 3% flow agent; and 0.5 to 3% lubricant.

The preferred pharmaceutically acceptable excipients for formulating these gelatin capsules are mannitol, lactose, corn starch, colloidal silica, magnesium stearate, and sodium lauryl sulphate, and more particularly mannitol, lactose, colloidal silica, and magnesium stearate.

The composition according to the invention can also be formulated in a tablet, preferably film-coated, of centesimal formulation containing: 1 to 30% by weight active ingredient with respect to the total weight of the composition, preferably 5 to 20% and very preferentially 8 to 20%; 40 to 92% diluent, preferably 65 to 92% and very preferentially 70 to 85%; 0.1 to 20% disintegration agent, preferably 0.1 to 10% and very preferentially 1 to 5%; 0.1 to 8% binder, preferably 2 to 5%; 0.1 to 3% gliding agent, preferably 0.5 to 1.4%; 0.2 to 3% lubricant, preferably 0.5 to 2.8%.

The excipients preferred for formulating these tablets are maltodextrin, mannitol, microcrystalline cellulose, lactose or lactose monohydrate, corn starch, sodium starch glycolate, crospovidone, polyvinylpyrrolidone, copovidone, carboxymethylcellulose, colloidal silica, sodium stearyl fumarate, and magnesium stearate and more particularly microcrystalline cellulose, lactose, sodium starch glycolate, copovidone, colloidal silica, and magnesium stearate.

Preferentially also, the pharmaceutical composition as defined above is a tablet, preferably film-coated, of centesimal formulation comprising 8 to 20% active ingredient; 70 to 85% diluent; 1 to 5% disintegration agent; 2 to 5% binder; 0.5 to 1.4% flow agent; and 0.5 to 2.8% lubricant with respect to the total weight of the tablet as well as approximately 4.5 to 5%, preferably 4.8% coating solution with respect to the total weight of the coated tablet.

Preferably, a pharmaceutical composition according to the present invention comprises a diluent selected from the following excipients: mannitol, lactose or lactose monohydrate, starch, calcium carbonate, microcrystalline cellulose, or maltodextrin.

Preferably, a pharmaceutical composition according to the present invention comprises a disintegration agent selected from the following excipients: starch, croscarmellose sodium, sodium starch glycolate, or crospovidone.

Preferably, a pharmaceutical composition according to the present invention comprises a binder selected from the following excipients: polyvinylpyrrolidone, copolymers of N-vinyl-2-pyrrolidone and vinyl acetate (copovidones), carboxymethylcellulose (CMC), pregelatinized starch, or methylcellulose.

Preferably, a pharmaceutical composition according to the present invention comprises a lubricant selected from the following excipients: magnesium stearate, sodium stearyl fumarate, calcium stearate or hydrogenated vegetable oil.

Preferably, a pharmaceutical composition according to the present invention comprises either microcrystalline cellulose (MCC) and/or copovidone or microcrystalline cellulose (MCC) and/or carboxymethylcellulose (CMC). Preferably, the CMC is at a level of 4 to 6%. Very preferentially, a pharmaceutical composition according to the present invention comprises microcrystalline cellulose (MCC). Very preferentially, a pharmaceutical composition according to the present invention comprises copovidone. Very preferentially also, a pharmaceutical composition according to the present invention comprises microcrystalline cellulose (MCC) and copovidone. Very preferentially, a pharmaceutical composition according to the present invention comprises microcrystalline cellulose (MCC). Very preferentially, a pharmaceutical composition according to the present invention comprises carboxymethylcellulose (CMC). Very preferentially, a pharmaceutical composition according to the present invention comprises microcrystalline cellulose (MCC) and carboxymethylcellulose (CMC).

Preferably also, the flow agent chosen is colloidal silica (or colloidal solution of silicon dioxide).

Preferably also, the lubricant chosen is magnesium stearate. The disintegration agent which is added to the formulation of the tablets as excipient increases the dissolution rate, and makes it possible to achieve immediate dissolution, even with tablets with high cohesion. According to the literature (e.g. J. Balasubramaniam, T. Bee, Pharmaceutical Technology Europe, Vol. 21, Number 9, 2009, pp 44-49), the most effective disintegration agents are crospovidone type A and B, followed by croscarmellose sodium.

Preferably, in the formulations of tablets according to the present invention, the disintegration agent used is sodium starch glycolate, and preferentially at a level of 1 to 5% and very preferentially of 3 to 4%.

Preferably, the pharmaceutical composition according to the present invention is a tablet containing 8 to 20% compound 1; 20 to 40% lactose and 25 to 50% micro-crystalline cellulose used as diluents; 2 to 8% copovidone used as binding agent; 1 to 5% sodium starch glycolate used as disintegration agent; 0.2 to 1.4% flow agent; and 0.5 to 2% lubricant with respect to the total weight of the tablet, and, very preferentially, 8 to 15% compound 1; 30 to 40% lactose and 40 to 50% micro-crystalline cellulose used as diluents; 2 to 5% copovidone used as binding agent; 3 to 4.5% sodium starch glycolate used as disintegration agent; 0.2 to 1.4% flow agent; and 0.5 to 2% lubricant with respect to the total weight of the tablet.

Very preferentially also, the pharmaceutical composition as described above is a tablet containing approximately 10% compound 1; 36.5% lactose; 45% micro-crystalline cellulose; 3% copovidone; 4% sodium starch glycolate; 0.5% colloidal silica; 1% magnesium stearate with respect to the total weight of the tablet. The term "approximately" means±0.5%.

According to a variant of the invention, the composition can comprise a coating or film coating.

Preferably such a coating has no significant effect on the immediate release of the active ingredient, i.e. the in vivo release kinetics of the active ingredient are unchanged.

Preferably also, the coating has the advantage of masking the taste of the active ingredient and allows secure handling for processing the solid composition in the form of a tablet.

The coating processes which can be used for the tablet described in the invention are well known to a person skilled in the art.

When the tablet comprises a coating the latter preferably comprises a polymer chosen from the group constituted by the polyethylene glycols, ethylcellulose, hydroxyethylcellulose, hydroxypropylmethylcellullose (hypromellose) but not limited to these. It is possible to use in particular a film-coating mixture containing polyethylene glycol (macrogol) and hydroxypropylmethylcellullose already formulated, for the aqueous film coating of solid oral pharmaceutical forms such as that marketed under the name Opadry® II white (lactose monohydrate, hypromellose, titanium dioxide (E171), triacetin) by the company Colorcon. Opadry® II white is soluble in water, and allows immediate disintegration of the oral pharmaceutical composition in the form of a tablet.

Preferably, the solid pharmaceutical composition according to the present invention is presented in tablet form. The invention also relates to tablets with immediate dissolution as well as tablets covered with a coating or film.

Pharmaceutical compositions are described as examples and in no way limit the scope of the invention.

Thus, a subject of the invention is also a process for the preparation of the compound according to the invention as described previously, from 6-oxo-6,7,8,9,10,11-hexahydro-cyclohepta[c]chromen-3-yl sulphamate characterized in that it comprises a stage of reducing the size of the particles.

Preferentially, the size of the particles is reduced by micronization, either in aprotic solvent medium, or by dry route.

Preferentially also, the size of the particles is reduced by wet grinding with an aprotic organic solvent.

The invention also relates to the manufacturing process of the solid pharmaceutical compositions of the invention, characterized by the following stages:
sieving of the components;
preparation of the tablets without coating (wet granulation, mixing and compression);
preparation of the coating solution.

Preferably, according to the process according to the invention, during the wet granulation stage, the mass of water with respect to the total mass of the active ingredient and of the binder, diluent and disintegration agent mixed beforehand, is comprised between approximately 10 and 30%.

Preferably, according to the process according to the invention, after the wet granulation stage, the granules are dried until residual moisture of less than 3% is obtained.

The composition during all the stages of the manufacturing process is produced by means of conventional equipment known to a person skilled in the art.

A formulation according to the present invention can be prepared according to the following process: a first mixture is produced constituted by the active ingredient which is first sieved at the same time as certain excipients included in the composition comprising a binder, and one or more diluents as well as a disintegration agent.

The sieving stage is carried out using a sieve in a suitable device such as a manual sieve.

The sieved substances are then introduced into a mixer-granulator and mixed for approximately 5 min. The mixing speed depends on the equipment chosen.

A mass of water for the granulation is then prepared so that its proportion with respect to the solid phase to be granulated is preferentially comprised between approximately 10 and 30%. By solid phase to be granulated is meant the total mass of the active ingredient and of the excipients mixed beforehand, added to the mass of binder.

The binder for the granulation is added to the mixer in its pulverulent form or preferentially dissolved in the mass of water in order to constitute the granulation solution.

The mixture obtained at the start of the process is then granulated by wet route with the granulation solution, in a mixer-granulator preferably of "high shear" type. The granulation time after the addition of the solution to be granulated is less than 10 min and preferentially less than 5 minutes.

The granules resulting from this last stage can then be dried in a conventional device such as for example a fluidized bed dryer. Preferably, the granules are dried until a residual moisture of less than 3% is obtained. The granules thus dried constitute the part conventionally called the internal phase of the tablet. They are then calibrated by grinding.

A second mixture is produced, which is constituted by the calibrated granules obtained previously and a so-called external phase constituted by: a portion of disintegration agent, a flow agent which makes it possible to improve the fluidity of the powder, and finally a lubricant.

The excipients of the external phase are first sieved in a suitable device such as a manual sieve.

The granules, the disintegration agent and the flow agent are then mixed, then the lubricant is introduced.

For the preparation of formulation in the form of tablets, the final resultant mixture can then be made into tablets using a press, of rotary type for example.

The hardness of a 400 mg tablet can be comprised between 6 and 12 kPascal (kPa). The hardness of a 100 mg tablet can be comprised between 4 and 8 kPa.

The tablets can then be coated in a film coating turbine by spraying of a coating suspension which has been prepared beforehand, preferably by addition of 16% of Opadry II® in purified water.

The temperature of the product during the film coating is comprised between 35 and 55° C., Preferably, the gain in mass of the tablet after drying is between 4 and 6% of the mass of the tablet before film coating.

The tablets can then be packaged and stored in blister packs or bottles.

According to the invention the non-coated tablet preferably does not exceed a total weight of 800 mg, preferably 400 mg.

The invention finally relates to the use of a pharmaceutical composition according to the invention as described previously for treating cancers, preferentially the hormone-dependent cancers, and also preferentially, breast, prostate, endometrial or ovarian cancers.

The present application also relates to polymorphs of the compound 6-oxo-6,7,8,9,10,11-hexahydrocyclohepta[c]chromen-3-yl sulphamate (or sulphamic acid 6,7,8,9,10,11-hexahydro-6-oxobenzo[b]cyclohepta[d]pyran-3-yl ester or compound 1). The invention also relates to the preparation of these polymorphic forms, their use as active ingredient, and more particularly as active ingredient for the treatment of certain cancers. The invention also relates to the pharmaceutical compositions containing these polymorphic forms as active ingredient.

The form succinctly described by Woo and called variety I hereafter produces characteristic absorption bands in the infrared. The Applicant obtained single crystals of suitable size and quality for a complete characterization of its structure.

The crystals obtained in the prior art do not allow good bioavailability and their preparation cannot be transferred to the industrial scale.

Moreover, the Applicant obtained crystals of compound 1 by an industrial process. Microscopic observation makes it possible to observe progressive opacification of the crystal from approximately 140-145° C. The phenomenon is not reversible: the crystal does not recover its initial appearance after slow or rapid cooling down. In DSC, an endothermic phenomenon corresponding to a solid-solid transition is observed as from 140° C. A second endothermic peak is observed at 170° C. corresponding to the melting of the non-converted variety I. A third endothermic peak is observed at 180° C. This third peak corresponds to the melting of another polymorphic form generated during the solid-solid transition. By X-ray powder diffraction carried out on the compound successively heated to 160° C. then cooled down to a temperature comprised between 18 and 25° C., peaks additional to those characteristic of variety I of compound 1 are observed, these peaks corresponding to another polymorphic form generated during the heating.

Thus, the crystals obtained under industrial conditions exhibit heterogeneities detected by DSC and/or by X-ray powder diffraction after heating to 160° C., heterogeneities which allow the germination and the growth of another crystalline form during the heating of the compound, making the product unstable during heating.

By heterogeneities is meant here defects in or on the crystals including macles or polytypism which can be detected by a conventional optical microscope or a microscope equipped with a polarized light device and/or by differential enthalpic analysis and/or by X-ray powder diffraction and/or by confocal Raman microscopy. The presence of such heterogeneities in the crystals can thus lead to numerous problems during storage of the active ingredient, or during the manufacturing process of tablets, gelatin capsules, creams, or other galenic forms. For example, a relative humidity stress can lead to unacceptable behaviour for a pharmaceutically active ingredient. Furthermore, as shown by Y. Mnyukh in *Fundamentals of solid-state phase transitions, ferromagnetism and ferroelectricity* (2001), the defects can pre-code a solid—solid transition via a mechanism—growth germination.

Now, for a clinical development of this molecule it is necessary to choose a crystalline form, achieve its production under industrial conditions, key factors being its thermal stability and its bioavailability.

The technical problem that the Applicant proposes to resolve is therefore to provide a stable and bioavailable form of compound 1 under conditions which can be used on an industrial scale.

A person skilled in the art knows that the treatment aimed at reducing the size of the particles by mechanical treatment can introduce defects, residual stresses in the crystallized phases, a polymorphic transition, a partial or total amorphization, optionally associated with a chemical degradation (*Jet-milling; from a particle perspective predicting particle fracture based on mechanical material properties* Onno M. de Vegt; PhD thesis University of Groningen; 19 Oct. 2007; Garnier, S.; Petit, S.; Mallet, F.; Petit, M.-N.; Lemarchand, a; Coste, S.; Lefebvre, J.; Coquerel, G., *Influence of ageing, grinding and preheating on the thermal behaviour of α-lactose monohydrate. Int. J. Pharm.* 2008, 361, 131-140).

The ability of a compound to exist under more than one crystalline form is defined by the term polymorphism and its different crystalline forms are known as "polymorphic varieties" or "polymorphs". Polymorphism can influence numerous properties of the solid state of an active ingredient. Different polymorphs of a substance can differ considerably from one to another, by their physical properties which can directly influence their solubility for example. Polymorphism has been demonstrated for numerous organic compounds.

Very unexpectedly, the Applicant has now found that an appropriate treatment of compound 1 obtained under industrial conditions, aim at reducing the size of the particles can produce variety I of compound 1 with a particle size compatible with the formulation of the active compound while concomitantly reducing the concentration of heterogeneities in the crystals, thus providing a stable and bioavailable form of compound 1 under conditions which can be used on an industrial scale. The DSC and X-ray powder diffraction analyses as described in the experimental part make it possible to demonstrate that the variety I thus obtained has an increased stability.

Thus, this variety I of low particle size, which is a subject of the invention, can be characterized by different analytical methods such as X-ray powder diffraction, differential scanning calorimetry (DSC) analysis, Raman spectroscopy, infrared spectroscopy or NMR of the solid.

Also, a subject of the invention is the solvate of crystalline DMSO of form 2 of compound 1, exhibiting using X-ray powder diffraction the characteristic peaks expressed as an angle (°2 theta) to ±0.1°2 theta:. 7.6; 18,7; 24.2; 29.9.

Very unexpectedly, the Applicant has now found that the crystals of form I obtained under industrial conditions having heterogeneities which allow the germination and growth of another crystalline form during heating of the compound: form III, stable at high temperature. A subject of the present invention is this novel form III of compound 1. This form III has the advantage of being thermodynamically stable at temperatures greater than 145° C.

Several synthesis routes exist for compound 1 of form III, according to the invention, of which one is via the intermediate of another novel crystalline form of compound 1, called form II.

Variety I of compound 1 can be characterized by X-ray powder diffraction with a diffraction diagram having in particular characteristic peaks expressed as an angle (°2 theta) to approximately ±0.1°2 theta: 7.5; 10.9; 13.1; 17.7; 19.0.

The angles (°2 theta) with a error of ±0.1°2 theta represent the reflection angle according to Bragg's Law i.e. the angle of incidence of the X-ray beam on the sample.

Variety I of compound 1 before reduction of the size of the particles can be characterized by a single crystal X-ray analysis.

Figure 6:
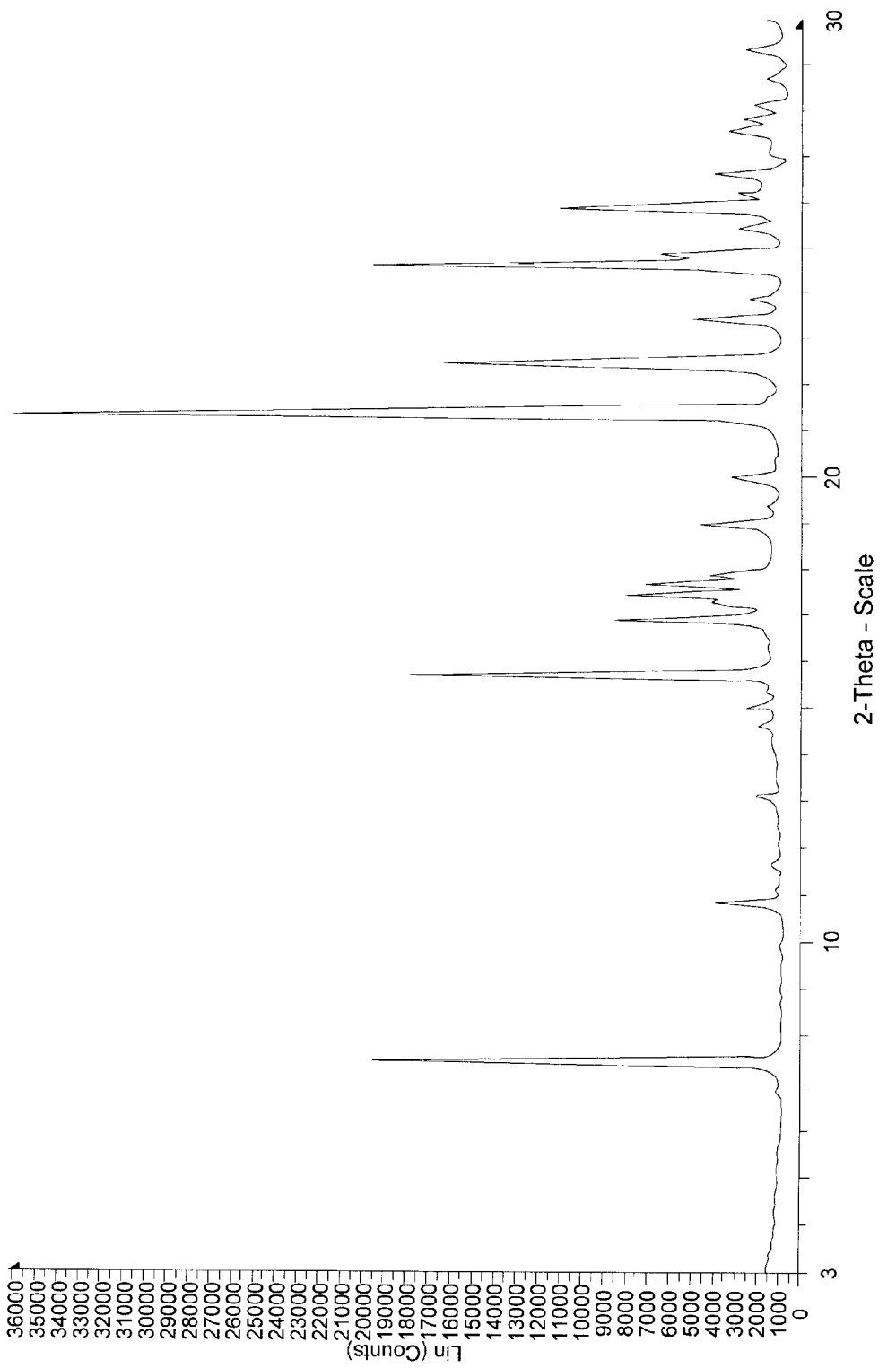
FIG. 6: experimental X-ray powder diffraction diagram of variety I of compound 1

Variety I of compound 1, of reduced particle size, can be characterized by an X-ray powder diffraction diagram (FIG. 6).

Figure 7:
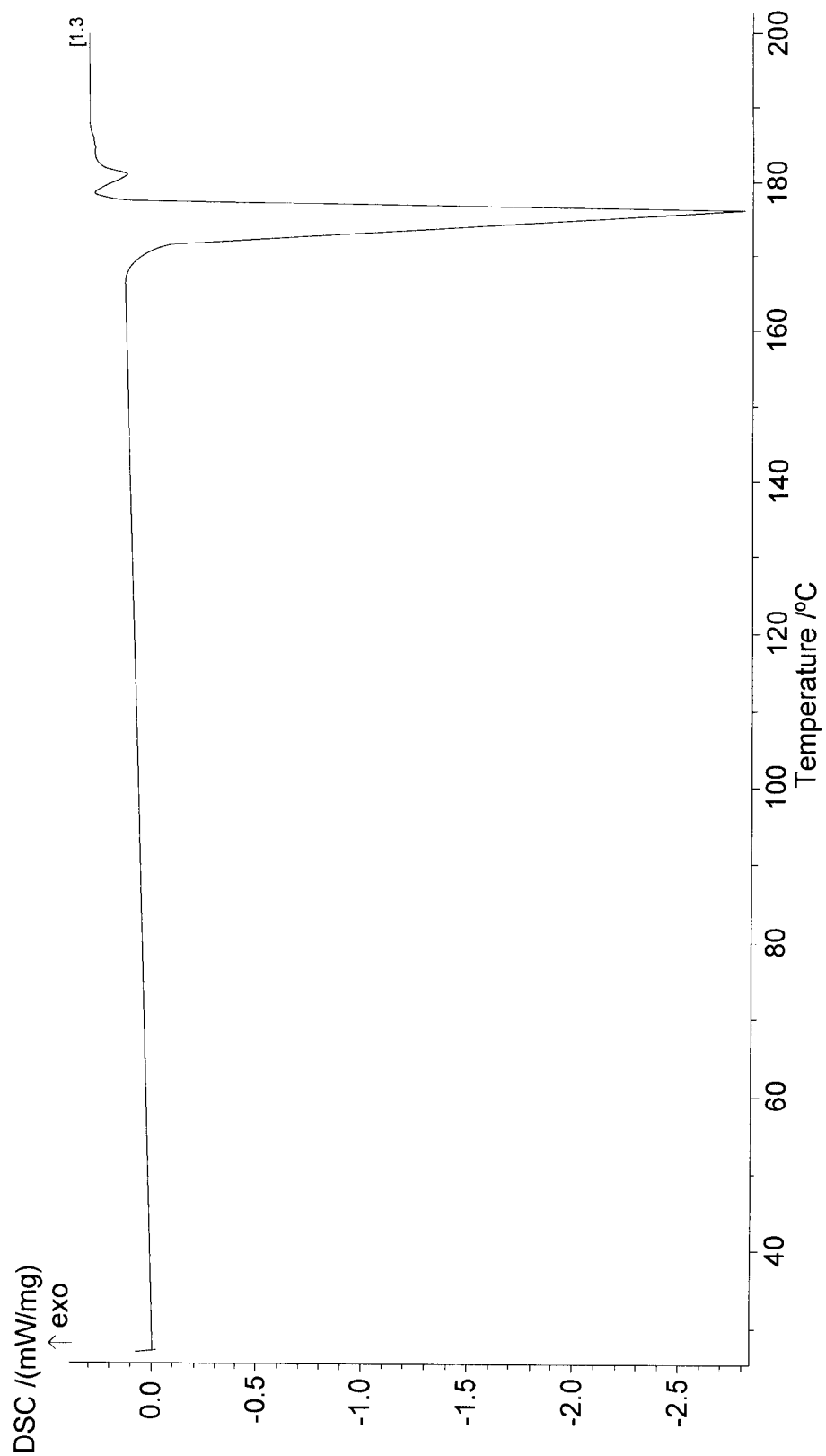
FIG. 7: DSC thermogram of variety I of compound 1

Variety I of compound 1, as described above, can also be characterized by a DSC thermogram (FIG. 7).

Figure 8:
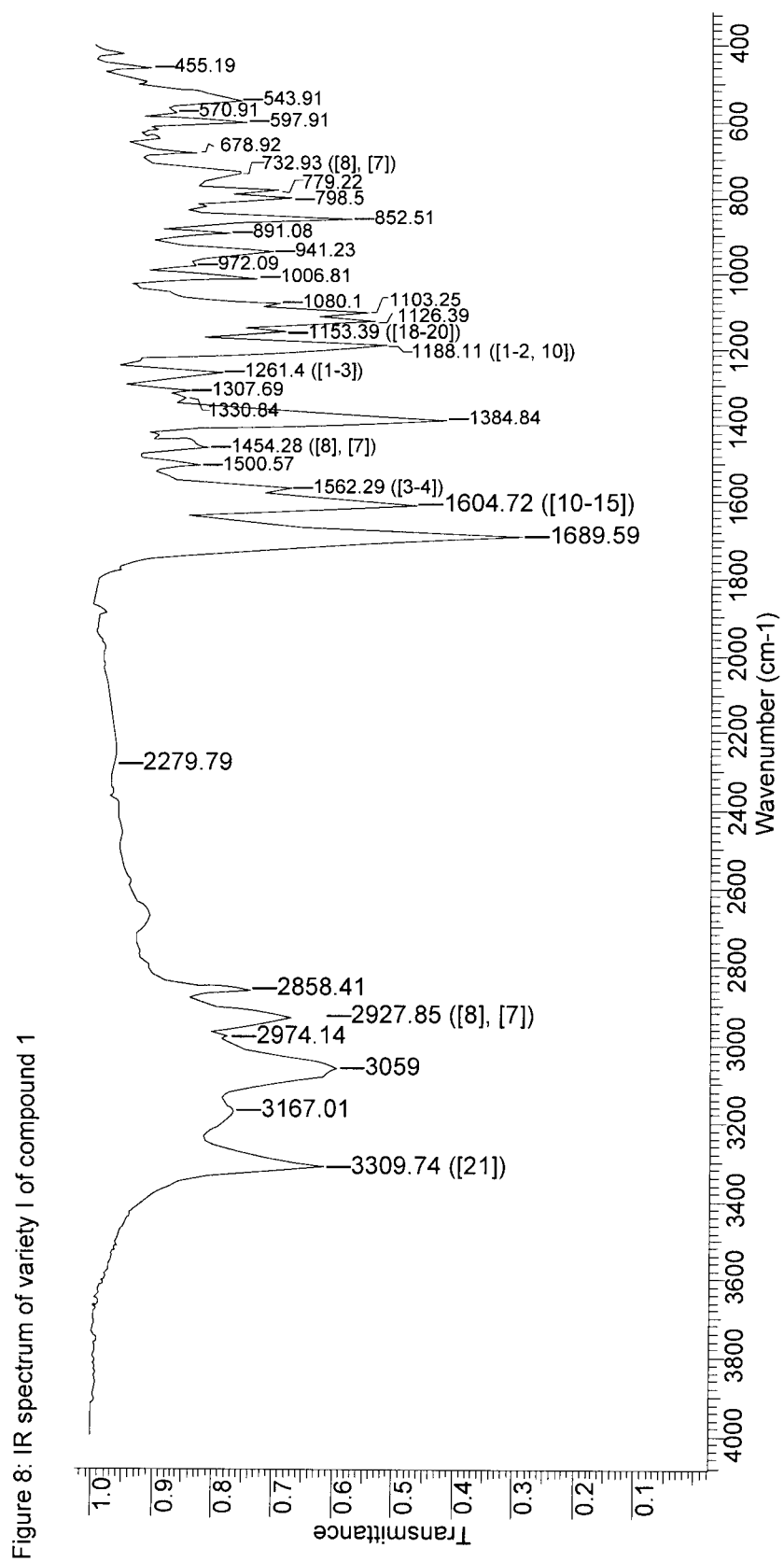
FIG. 8: IR spectrum of variety I of compound 1

Variety I of compound 1, as described above, can also be characterized by an infrared spectrum (FIG. 8).

Figure 9:
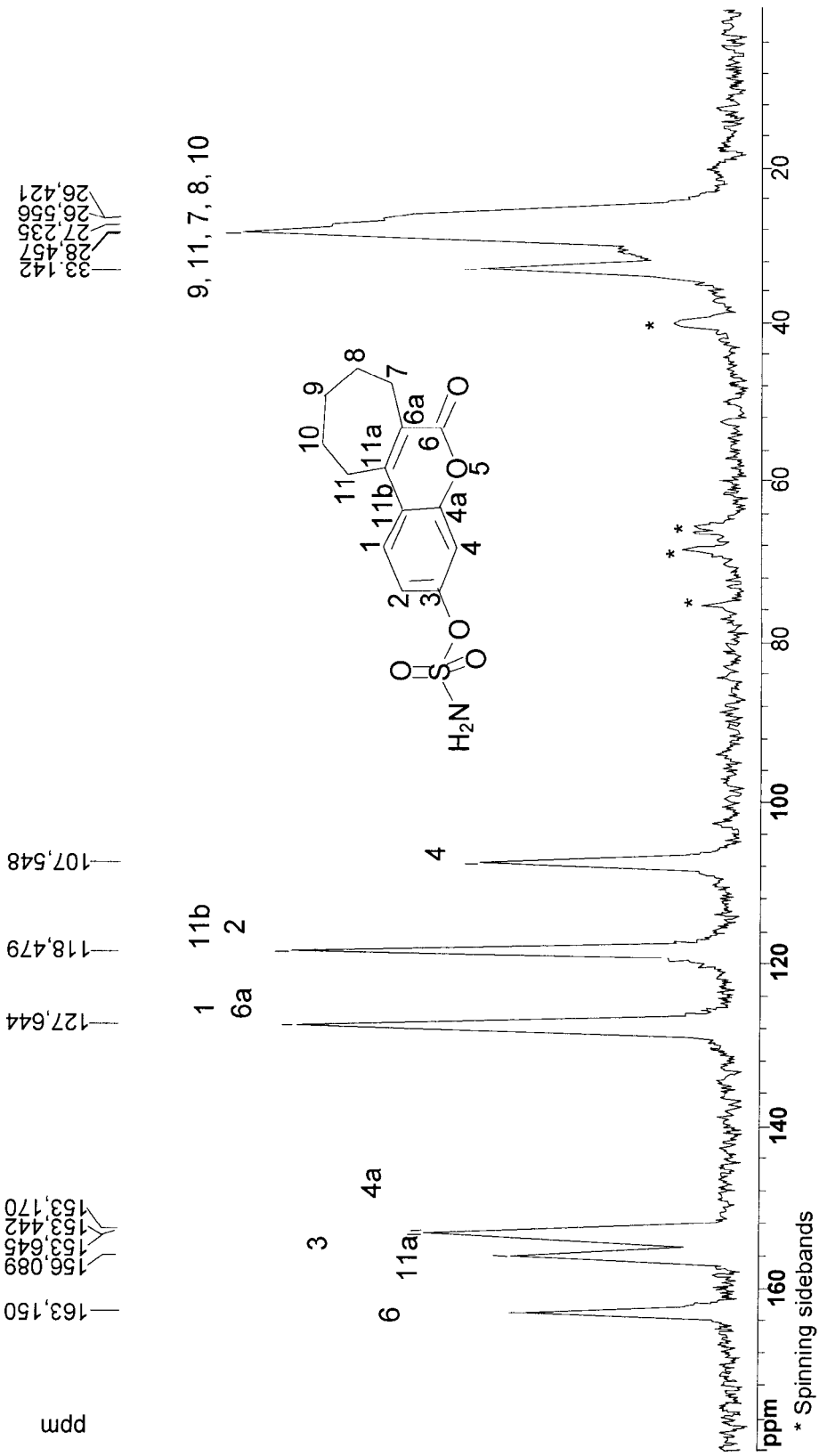
FIG. 9: NMR spectrum of the solid of variety I of compound 1

Variety I of compound 1, as described above, can also be characterized by an NMR spectrum of the solid (FIG. 9).

The Applicant therefore proposes variety 1 of compound 1 obtained by an appropriate treatment in order to obtain a particle size comprised between 0.1 and 20 μm.

The present invention has numerous advantages, in particular an increased stability and a bioavailability.

A subject of the present invention is therefore a polymorphic compound of 6-oxo-6,7,8,9,10,11-hexahydrocyclohepta[c]chromen-3-yl sulphamate of particle size comprised between 0.1 and 20 μm, and exhibiting by X-ray powder diffraction the characteristic peaks expressed as an angle (°2 theta) to ±0.1°2 theta: 7.5; 10.9; 13.1; 17.7; 19.0.

Preferentially, the compound according to the invention has a particle size comprised between 1 and 15 μm.

More preferentially, the compound according to the invention has a particle size comprised between 3 and 7 μm.

Even more preferentially the compound according to the invention has a size of 5 μm±1 μm.

Preferably, the compound as defined above exhibits by X-ray powder diffraction the characteristic peaks expressed as an angle (°2 theta) to ±0.1°2 theta: 7.5; 10.9; 13.1; 15.0; 15.8; 17.0; 17.7; 19.0; 22.5.

Preferentially also, the compound as defined above exhibits by X-ray powder diffraction carried out after heating to 160° C. then returning to a temperature comprised between 18 and 25° C. the following characteristic peaks expressed as an angle (°2 theta) to ±0.1°2 theta: 7.5; 10.9; 13.1; 17.7; 19.0 without additional peaks corresponding to the form generated during the heating to 160° C.

Very preferentially, the compound as defined above exhibits using DSC with a temperature gradient of 5° C.·min$^{-1}$ an endothermic melting peak at 170° C.±5° C. and an endothermic peak at 180° C.±2° C. it being understood that the peak at 180° C. represents at maximum 10% of the enthalpy exchanged during melting at 170° C.

Very preferentially also, the compound as defined above does not exhibit using DSC an endothermic event between 140 and 155° C.

Yet more preferentially, the compound as defined above exhibits using infrared spectroscopy, the characteristic peaks expressed in cm$^{-1}$ to ±5 cm-1: 3310; 3167; 3059; 891; 798; 733; 679; 455; and even more preferentially the characteristic peaks expressed in cm$^{-1}$ to ±5 cm-1: 3310; 3167; 3059; 2928; 2858; 1690; 1605; 1454; 1385; 1261; 1188; 1126; 941; 891; 853; 798; 733; 679; 598; 544; 455.

According to a variant, the invention relates to a compound as defined above as a medicament.

The compound according to the invention can be formulated in various pharmaceutical compositions. In the case of a solid form, it can be for example powder, granules, tablets, gelatin capsules, liposomes or suppositories. In the case of a liquid form, it can be for example, solutions, emulsions, suspensions or syrups. The administration of compound according to the invention can be done for example by topical, oral, parenteral route, by intramuscular, sub-cutaneous injection and in particular in the form of a gelatin capsule, tablet, patch or cream.

Appropriate supports or excipients can be, for example, maltodextrin, mannitol, microcrystalline cellulose, lactose, corn starch, sodium starch glycolate, croscarmellose sodium, polyvinyl-polypyrrolidone (or crospovidone), polyvinylpyrrolidone, carboxymethylcellulose, pregelatinized starch, methylcellulose, polyethylene glycol, macrogol, polyglycol, polyoxyethylene, polydiol, pyrrolidone-2, colloidal silica, talc, magnesium stearate, sodium stearyl fumarate, calcium stearate, hydrogenated vegetable oil, sodium lauryl sulphate, calcium phosphate, sugars, dextrin, starch, gelatin, cellulose, wax, or also water, organic solvents such as glycerol or the glycols, similarly their mixtures, in varying proportions, with or without water. These supports, added to the active ingredient, serve as:

diluents, such as mannitol, lactose, starch, calcium carbonate, microcrystalline cellulose, or maltodextrin;
 disintegration agents, such as starch, sodium croscarmellose, sodium starch glycolate, or crospovidone;
 binders, such as polyvinylpyrrolidone, carboxymethylcellulose, pregelatinized starch, or methylcellulose;
 flow agents, such as colloidal silica, or talc;
 lubricants, such as magnesium stearate, sodium stearyl fumarate, calcium stearate or hydrogenated vegetable oil;
 solubilizing agents, such as polyethylene glycol, macrogol, polyglycol, polyoxyethylene, polydiol, pyrrolidone-2, or polyvinylpyrrolidone;
 surfactants (or surface active agents) such as sodium lauryl sulphate.

The composition according to the invention, can be formulated in a gelatin capsule containing: 5 to 30% active ingredient (preferentially 6 to 13%); 40 to 92% diluent (preferentially 65 to 92%; very preferentially 85 to 90%); 0 to 30% disintegration agent (preferentially 0 to 22%; very preferentially 0%); 0 to 5% surfactant (preferentially 0%); 0 to 5% solubilizing agent (preferentially 0%); 0.1 to 3% flow agent (preferentially 0.9 to 1.4%); 0.5 to 3% lubricant (preferentially 0.6 to 2.8%).

The preferred excipients for formulating these gelatin capsules are mannitol, lactose, corn starch, colloidal silica, magnesium stearate, and sodium lauryl sulphate, and more particularly mannitol, lactose, colloidal silica, and magnesium stearate.

The composition according to the invention, can also be formulated in a tablet containing: 5 to 30% active ingredient (preferentially 7 to 15% and very preferentially 10 to 15%); 40 to 92% diluent (preferentially 34 to 89% and very preferentially 70 to 85%); 0 to 40% disintegration agent (preferentially 0 to 20% and very preferentially 3 to 5%); 0 to 8% binder (preferentially 2 to 5%); 0.1 to 3% flow agent (preferentially 0.5 to 1.4%); 0.5 to 3% lubricant (preferentially 0.5 to 2.8%).

The excipients preferred for formulating these tablets are maltodextrin, mannitol, microcrystalline cellulose, lactose, corn starch, sodium starch glycolate, crospovidone, polyvinylpyrrolidone, carboxymethylcellulose, colloidal silica, magnesium stearylfumarate, and magnesium stearate and more particularly microcrystalline cellulose, lactose, sodium starch glycolate, polyvinylpyrrolidone, colloidal silica, and magnesium stearate.

According to a variant, the invention relates to a pharmaceutical composition comprising, as active ingredient, 6-oxo-6,7,8,9,10,11-hexahydrocyclohepta[c]chromen-3-yl sulphamate of particle size comprised between 0.1 and 20 μm, in combination with at least one pharmaceutically acceptable support; preferentially, 6-oxo-6,7,8,9,10,11-hexahydrocyclohepta[c]chromen-3-yl sulphamate has a particle size comprised between 1 and 15 μm; more preferentially between 3 and 7 μm and more preferentially also 6-oxo-6,7,8,9,10,11-hexahydrocyclohepta[c]chromen-3-yl sulphamate has a size of 5 μm±1 μm.

Preferentially, the pharmaceutical composition as defined above, comprises as active ingredient, compound 1 of variety I as defined previously.

Very preferentially, the pharmaceutical composition as defined above is a gelatin capsule; and more preferentially also a gelatin capsule comprising 5 to 30% active ingredient; 40 to 92% diluent; 0 to 30% disintegration agent; 0 to 5% surfactant; 0 to 5% solubilizing agent; 0.1 to 3% flow agent; and 0.5 to 3% lubricant.

Very preferentially also, the pharmaceutical composition as defined above is a tablet, and more preferentially also a tablet comprising 5 to 30% active ingredient; 40 to 92% diluent; 0 to 40% disintegration agent; 0 to 8% binder; 0.1 to 3% flow agent; and 0.5 to 3% lubricant.

The synthesis routes for compound 1 are envisaged in the prior art, as described in patent EP 880514 or by L. W. Woo, et al. in *Chemistry & Biology*, 2000, 7, 773-91.

The Applicant has now found that this compound can be synthesized in two chemical stages. The first stage consists of condensing in a strong acid (such as sulphuric acid, trifluoroacetic acid or methanesulphonic acid) 2-carbetoxycycloheptanone with resorcinol, intermediate 3-hydroxy-8,9,10,11-tetrahydrocyclohepta[c]chromen-6(7H)-one is isolated by precipitation using an alcohol/water mixture (for example by adding ethanol then water). In a second stage, sulphonylisocyanate chloride is converted, in toluenic solution, to sulphamoyl chloride, by the action of formic acid, then condensed with the previous intermediate dissolved in a solvent such as DMA. The reaction medium is treated with water and extracted by an organic solvent (preferably 2-methyltetrahydrofurane: MeTHF), and crude compound 1 is then precipitated from the organic phase by adding an antisolvent (preferably methylcyclohexane). Finally pure compound 1 is obtained by recrystallization of the crude product by dissolution in acetone or ethyl acetate while hot and precipitation by adding an antisolvent (preferably methylcyclohexane).

As a result, a subject of the invention is also the preparation process for 6-oxo-6,7,8,9,10,11-hexahydrocyclohepta[c]chromen-3-yl sulphamate characterized in that it comprises the following stages:
  condensation of 2-carbetoxycycloheptanone with resorcinol in a strong acid,
  isolation of 3-hydroxy-8,9,10,11-tetrahydrocyclohepta[c]chromen-6(7H)-one thus obtained by precipitation using an alcohol/water mixture,
    condensation of 3-hydroxy-8,9,10,11-tetrahydrocyclohepta[c]chromen-6(7H)-one with chloride sulphamoyl in an aprotic solvent,
    recrystallization of the crude product obtained by dissolution in acetone while hot or ethyl acetate and the addition of an antisolvent such as methylcyclohexane.

The compound according to the invention, as described previously, is obtained from compound 1 in the form of variety I by a treatment aimed at reducing the size of the particles.

Thus, a subject of the invention is also a process for the preparation of the compound according to the invention as described previously, from 6-oxo-6,7,8,9,10,11-hexahydrocyclohepta[c]chromen-3-yl sulphamate characterized in that it comprises a stage of reducing the size of the particles.

Preferentially, the size of the particles is reduced by micronization.

Preferentially also, the size of the particles is reduced by wet grinding with an organic non-protic solvent.

A subject of the present invention is also a polymorphic compound of 6-oxo-6,7,8,9,10,11-hexahydrocyclohepta[c]chromen-3-yl sulphamate, exhibiting using X-ray powder diffraction the characteristic peaks expressed as an angle (°2 theta) to ±0.1°2 theta: 8.6; 11.3; 28.6 (compound of form III). Preferably, this compound form III exhibits the characteristic peaks expressed as an angle (°2 theta) to ±0.1°2 theta: 8.6; 11.3; 12.0; 16.6; 20.9; 23.0; 28.6.

A more particular subject of the invention is a compound of form III as defined previously which, using single crystal X-ray diffraction, exhibits the following cell parameters:

| Cell structure | Monoclinic |
|---|---|
| Space group | Cc (no. 9) |
| Cell parameter a | 11.327(1) Å |
| Cell parameter b | 20.489(2) Å |
| Cell parameter c | 7.870(1) Å |
| Cell parameter β | 131.55(1)° |
| Cell volume | 1366.9(2) Å$^3$ |
| Number of molecules per cell: Z | 4 |
| Calculated density | 1.53 g·cm$^{-3}$ | the following reduced coordinates ($\times 10^4$) and the equivalent isotropic motion parameters of ($\text{Å}2 \times 10^3$):

|  | X | y | Z | U(eq) |
|---|---|---|---|---|
| S(1) | 14534(1) | −1891(1) | 11571(1) | 41(1) |
| O(1) | 9079(2) | −569(1) | 5756(3) | 39(1) |
| O(2) | 13824(2) | −1450(1) | 12407(3) | 48(1) |
| O(3) | 6862(3) | −250(1) | 2510(3) | 57(1) |
| O(4) | 13672(3) | −1754(1) | 9246(3) | 62(1) |
| O(5) | 14551(3) | −2522(1) | 12277(5) | 73(1) |
| N(1) | 16289(3) | −1661(2) | 12982(5) | 55(1) |
| C(1) | 12910(3) | −904(1) | 11114(4) | 36(1) |
| C(2) | 11424(3) | −995(1) | 9041(4) | 37(1) |
| C(3) | 10541(3) | −449(1) | 7814(4) | 31(1) |
| C(4) | 11093(3) | 187(1) | 8587(4) | 32(1) |
| C(5) | 12593(3) | 249(1) | 10745(4) | 40(1) |
| C(6) | 13504(3) | −284(1) | 11996(4) | 42(1) |
| C(7) | 8111(3) | −78(1) | 4284(4) | 39(1) |
| C(8) | 8699(3) | 589(1) | 4976(4) | 37(1) |
| C(9) | 10098(3) | 718(1) | 7049(4) | 34(1) |
| C(10) | 10637(3) | 1421(1) | 7790(5) | 43(1) |
| C(11) | 9541(4) | 1809(1) | 7904(5) | 46(1) |
| C(12) | 8072(4) | 2076(1) | 5641(5) | 56(1) |
| C(13) | 6921(4) | 1568(2) | 3890(5) | 55(1) |
| C(14) | 7630(4) | 1111(1) | 3226(5) | 48(1) | the following coordinates of the hydrogen atoms ($\times 10^4$) and equivalent isotropic displacement parameters ($\text{Å}^2 \times 10^3$) (U(eq) equals a third of the value of the orthogonal tensor Uij):

|  | X | y | Z | U(eq) |
|---|---|---|---|---|
| HN1 | 16970(60) | −1842(18) | 14350(80) | 78(13) |
| HN2 | 16430(50) | −1342(19) | 12870(60) | 56(12) |
| H(2) | 11025 | −1412 | 8483 | 44 |
| H(5) | 12982 | 664 | 11349 | 48 |
| H(6) | 14506 | −231 | 13414 | 50 |
| H(10A) | 10682 | 1631 | 6729 | 52 |
| H(10B) | 11693 | 1424 | 9273 | 52 |
| H(11A) | 9218 | 1531 | 8530 | 55 |

-continued

| | X | y | Z | U(eq) |
|---|---|---|---|---|
| H(11B) | 10129 | 2172 | 8944 | 55 |
| H(12A) | 7523 | 2355 | 5918 | 67 |
| H(12B) | 8398 | 2347 | 5004 | 67 |
| H(13A) | 6016 | 1789 | 2538 | 66 |
| H(13B) | 6550 | 1309 | 4487 | 66 |
| H(14A) | 6778 | 901 | 1798 | 57 |
| H(14B) | 8227 | 1369 | 2988 | 57 | the following interplanar spacings:

| H | K | L | 2Theta/deg | d/Å | I/rel, | |F(hkl)| |
|---|---|---|---|---|---|---|
| 0 | 2 | 0 | 8.63 | 10.24 | 16.76 | 35.88 |
| 1 | 1 | 0 | 11.29 | 7.83 | 37.69 | 49.89 |
| -1 | 1 | 1 | 12.05 | 7.34 | 59.53 | 66.98 |
| 1 | 3 | 0 | 16.66 | 5.32 | 57.37 | 91.43 |
| -1 | 3 | 1 | 17.18 | 5.16 | 11.98 | 43.15 |
| 0 | 2 | 1 | 17.35 | 5.11 | 92.5 | 121.09 |
| -2 | 2 | 1 | 17.92 | 4.95 | 73.94 | 111.89 |
| 2 | 0 | 0 | 20.94 | 4.24 | 13.54 | 79.54 |
| -2 | 0 | 2 | 22.60 | 3.93 | 89.64 | 221.49 |
| 2 | 2 | 0 | 22.69 | 3.92 | 23.89 | 81.17 |
| 0 | 4 | 1 | 22.99 | 3.87 | 27.76 | 88.74 |
| -2 | 4 | 1 | 23.43 | 3.79 | 43.01 | 112.65 |
| 1 | 1 | 1 | 23.81 | 3.73 | 20.41 | 78.91 |
| 1 | 5 | 0 | 24.10 | 3.69 | 13.86 | 65.87 |
| -2 | 2 | 2 | 24.23 | 3.67 | 3.27 | 32.19 |
| -3 | 1 | 1 | 24.64 | 3.61 | 12.1 | 63 |
| -1 | 1 | 2 | 24.92 | 3.57 | 10.88 | 60.46 |
| -3 | 1 | 2 | 25.73 | 3.46 | 100 | 189.5 |
| 0 | 6 | 0 | 26.07 | 3.41 | 11.99 | 94.11 |
| 2 | 4 | 0 | 27.29 | 3.27 | 2.04 | 28.78 |
| -3 | 3 | 1 | 27.59 | 3.23 | 12.23 | 71.34 |
| -3 | 3 | 2 | 28.57 | 3.12 | 46.83 | 144.9 |

Preferentially a subject of the invention is a compound (form IIII) as defined previously which exhibits using DSC at 5° C.·min$^{-1}$ an endothermic melting peak of 180° C.±2° C.

Preferably the compound (form III) according to the invention, as defined previously, exhibits using infrared spectroscopy the following characteristic peaks expressed in cm$^{-1}$ to ±5 cm$^{-1}$: 3406; 3217; 1678; 1011; 563;
and very preferentially the following characteristic peaks expressed in cm$^{-1}$ to ±5 cm$^{-1}$: 3406; 3217; 3082; 2924; 1678; 1385; 1269; 1134; 1011; 934; 845; 601; 563; 536.

According to a variant, a subject of the invention is a compound of form III as defined above, as a medicament.

A subject of the invention is also a pharmaceutical composition comprising as active ingredient, a compound of form IIII as defined previously, in combination with at least one pharmaceutically acceptable support.

Also, a subject of the invention is the crystalline DMSO solvate of form 1 of compound 1, exhibiting using X-ray powder diffraction the characteristic peaks expressed as an angle (°2 theta) to ±0.1°2 theta: 6.6; 10.9; 13.1; 14.3; 15.7; 16.7; 17.4; 18.3; 19.6; 20.8; 21.9; 22.6; 23.0; 24.7; 24.9; 25.2; 25.5; 25.8; 26.6; 26.9; 27.2; 28.3.

Also, a subject of the invention is the crystalline DMSO solvate of form 3 of compound 1, exhibiting using X-ray powder diffraction the characteristic peaks expressed as an angle (°2 theta) to ±0.1°2 theta: 9.8; 13.9; 16.0; 17.7; 19.1; 22.1.

Furthermore, a subject of the invention is also the crystalline 1,4-dioxane hemisolvate of compound 1, exhibiting using X-ray powder diffraction the characteristic peaks expressed as an angle (°2 theta) to ±0.1°2 theta: 9.8; 10.0; 10.8; 13.6; 13.9; 14.1; 15.9; 16.1; 18.0; 18.3; 19.0; 19.6; 20.0; 20.1; 20.2; 20.6; 21.4; 21.7; 21.8; 22.0; 22.2; 22.3; 23.4; 23.9; 24.3; 24.4; 24.9; 25.3; 25.4; 26.2; 27.0; 27.1; 27.3; 27.5; 28.2; 28.4; 28.5; 28.7; 29.1; 29.4.

Moreover, a subject of the invention is also the polymorphic compound of compound 1, a compound of form II, exhibiting using X-ray powder diffraction the characteristic peaks expressed as an angle (°2 theta) to ±0.1°2 theta: 9.4; 10.7; 12.8; 18.2; 18.9; 19.7; 20.4; 23.2; and preferentially the characteristic peaks expressed as an angle (°2 theta) to ±0.1°2 theta: 9.4; 10.7; 12.2; 12.8; 15.1; 18.2; 18.9; 19.7; 20.4; 21.1; 22.0; 23.2.

Preferentially, this compound of form II exhibits using DSC at 5° C.·min$^{-1}$ an endothermic melting peak at 165° C.±5° C.; more preferentially, it exhibits using infrared spectroscopy the characteristic peaks expressed in cm$^{-1}$ to ±5 cm$^{-1}$: 3356; 3321; 3186; 1504; 872; 787; and even more preferentially the characteristic peaks expressed in cm$^{-1}$ to ±5 cm$^{-1}$: 3356; 3321; 3186; 3078; 2932; 2851; 1693; 1609; 1504; 1462; 1377; 1265; 1192; 1123; 937; 872; 837; 787; 594.

The compound according to the invention, as described previously, is obtained from compound 1 by an additional stage which can be:
  a desolvation of the DMSO solvate of form 1 in water,
  a desolvation of the DMSO solvate of form 3 in water,
  an atomization in ethanol,
  an atomization in acetone,
  a reimpasting in cumene under reflux,
  a heat treatment then a micronization, then a second heat treatment, or
  a heat treatment of form II.

Thus, according to a variant, a subject of the invention is the process for the preparation of a compound of form III as defined previously starting from compound 1, according to one of the following methods:
  a) by stirring and precipitation from DMSO in order to lead to the crystalline DMSO solvate of form 1 as defined previously, which compound is then desolvated in water;
  b) by stirring and precipitation from DMSO in order to lead to the crystalline DMSO solvate of form 3 as defined previously, which compound is then desolvated in water;
  c) by atomization in ethanol;
  d) by atomization in acetone;
  e) by reimpasting in cumene under reflux;
  f) by heat treatment at a temperature comprised between 155° C. and 165° C. for 10 to 20 minutes, followed by a micronization, then by a second heat treatment at a temperature comprised between 155° C. and 165° C. for 10 to 20 minutes,
  g) by treatment of a compound of form II as defined previously, and obtained:
    either by atomization of compound 1 in 1,4-dioxane,
    or by stirring and precipitation of compound 1 from 1,4-dioxane in order to lead to the crystalline 1,4-dioxane hemisolvate as defined previously, which compound is then desolvated by heating from 20 to 80° C. at 5° C.·min$^{-1}$ under a stream of inert gas,
  which treatment consists of a heat treatment at a temperature comprised between 155° C. and 165° C. for 6 to 10 minutes.

Preferentially, the process according to the invention goes through desolvation in water of the crystalline DMSO solvate of form 1 as defined previously.

Preferentially, the process according to the invention goes through desolvation in water of the crystalline DMSO solvate of form 3 as defined previously.

Preferentially also, the process according to the invention goes through atomization in ethanol.

Preferentially also, the process according to the invention goes through atomization in acetone.

Very preferentially, the process according to the invention goes through reinipasting in cumene under reflux.

Even more preferentially, the process according to the invention goes through heat treatment at a temperature comprised between 155° C. and 165° C. for 10 to 20 minutes, followed by a micronization, then a second heat treatment at a temperature comprised between 155° C. and 165° C. for 10 to 20 minutes;

and preferentially, the heat treatments are carried out at 160° C.±1° C. for 15 minutes.

Even more preferentially also, the process according to the invention goes through heat treatment of a compound of form II as defined previously, at a temperature comprised between 155° C. and 165° C. for 6 to 10 minutes;

and preferentially the heat treatment is carried out at 160° C.±1° C. for 7.5 minutes.

Preferably also, the compound of form II as defined previously, is obtained by the atomization of compound 1 in 1,4-dioxane; or, the compound of form II as defined previously, is obtained by the desolvation of a crystalline 1,4-dioxane hemisolvate as defined previously.

According to a variant, a subject of the invention is the process for the preparation of the crystalline DMSO solvate of form 1 as defined previously, starting from compound 1, by stirring and precipitation from DMSO.

According to a variant, a subject of the invention is the process for the preparation of the crystalline DMSO solvate of form 3 as defined previously, starting from compound 1, by stirring and precipitation from DMSO.

According to a variant, a subject of the invention is the process for the preparation of a crystalline 1,4-dioxane hemisolvate as defined previously, starting from compound 1, by stirring and precipitation from 1,4-dioxane.

As for form II mentioned above it can be obtained it according to two synthesis routes:
  directly, by atomization in 1,4-dioxane
  by desolvation of the 1-4-dioxane hemisolvate of compound 1 obtained beforehand by precipitation from 1,4-dioxane.

Also, according to another variant, a subject of the invention is the process for the preparation of a compound of form II as defined previously, starting from compound 1, according to one of the following methods:
  atomization in 1,4-dioxane;
  stirring and precipitation from 1,4-dioxane in order to lead to a crystalline 1,4-dioxane hemisolvate as defined previously, which compound is then subjected to a desolvation by heating from 20 to 80° C. at 5° C.·min$^{-1}$ under a stream of inert gas.

Preferentially, the process for the preparation of a compound of form II as defined previously, goes through desolvation of a crystalline 1,4-dioxane hemisolvate as defined previously.

Preferentially also, the process for the preparation of a compound of form II as defined previously, goes through atomization in 1,4-dioxane.

Alternatively, the subject of the invention is the use of a compound of variety I or of form III as defined previously in order to produce a medicament intended to treat cancers; preferentially hormone-dependent cancers and preferentially also, a cancer chosen from breast, prostate, endometrial or ovarian cancers.

The experimental part which follows is presented in order to illustrate the above procedures and should in no event be considered as limiting the scope of the invention.

Unless defined otherwise, all the technical and scientific terms used in the present Application have the same meaning as that usually understood by an ordinary specialist in the field to which the invention belongs. Moreover, all the patents (or patent applications) as well as the other bibliographical references are incorporated by way of reference.

EXPERIMENTAL PART

1. Compositions According to the Invention

Example 1a

A composition in the form of a tablet and comprising compound 1 as active ingredient is shown in Table 1 below. Such a composition can be prepared by wet granulation according to diagram 1 below for a 5 kg batch and a 40 mg dose.

TABLE 1 centesimal composition of a tablet and coating

| composition | Composition | |
|---|---|---|
| | mass (mg/tablet) | centesimal formula (%) |
| Compound 1 | 40.0 | 10.0 |
| Monohydrated lactose | 146.0 | 36.5 |
| Microcrystalline cellulose | 180.0 | 45.0 |
| Sodium starch glycolate, type A | 16.0 | 4.0 |
| Copovidone | 12.0 | 3.0 |
| Colloidal silica | 2.0 | 0.5 |
| Magnesium stearate | 4.0 | 1.0 |
| Water | — | — |
| Total mass of the tablet | 400.0 | 100.0 |
| tablet | 400.0 | 95.2 |
| Opadry ® II White/coating | 20.0 | 4.8 |

The coating, which was applied to 40 mg tablets, is composed of Opadry® II white (Colorcon); this is a commercially available mixture of coatings used for immediate release tablets. The main objective of this coating is to mask the bad taste of the medicamentous substance. It also reduces the risks linked to handling during the packaging operations of the tablets containing powerful active ingredients.

Example 1b

A composition in the form of a gelatin capsule and comprising compound 1 as active ingredient is shown in Table 2 below.

TABLE 2 centesimal composition of a gelatin capsule

| Composition | Centesimal formula (%) |
|---|---|
| Compound 1 | 7.0 |
| Mannitol | 31.0 |
| Monohydrated lactose | 57.7 |

TABLE 2-continued centesimal composition of a gelatin capsule

| Composition | Centesimal formula (%) |
|---|---|
| anhydrous colloidal silica | 1.4 |
| magnesium stearate | 2.8 |
| gelatin capsule | — |

2. Effect of Disintegration Agent on the Dissolution Profiles

All the excipients are analyzed according to the monographs of the current European Pharmacopoeia.

The effect of the disintegration agent appears by comparison of the dissolution values at 30 minutes of compositions 2 and 17 described in section 3 below, without sodium starch glycolate.

Different tests have been carried out on the effect of the addition of a disintegration agent on the dissolution profile and the disintegration time of the tablet was studied. Four compositions of tablets were produced in order to study the effect of two disintegration agents, sodium starch glycolate, type A (Explotab®) and pregelatinized corn starch (Starch 1500®).

TABLE 3

Composition of the tablet without coating

| Composition | Centesimal formulation (%) | | | |
|---|---|---|---|---|
| | 1 | 2 | 3 | 4 |
| internal phase | | | | |
| Compound I | 15.0 | 15.0 | 15.0 | 15.0 |
| Sodium starch glycolate, type A | — | 1.0 | — | 1.5 |
| Lactose | 30.0 | 26.0 | 30.0 | 25.0 |
| Microcrystalline cellulose | 49.2 | 37.4 | 46.0 | 36.4 |
| Copovidone | 4.2 | 4.0 | 4.0 | 4.0 |
| external phase | | | | |
| pregelatinized corn starch | — | 15.0 | — | 15.0 |
| Sodium starch glycolate, type A | — | — | 3.0 | 1.5 |

TABLE 3-continued

Composition of the tablet without coating

| Composition | Centesimal formulation (%) | | | |
|---|---|---|---|---|
| | 1 | 2 | 3 | 4 |
| anhydrous colloidal silica | 0.8 | 0.8 | 1.0 | 0.8 |
| magnesium stearate | 0.8 | 0.8 | 1.0 | 0.8 |
| Total | 100.0 | 100.0 | 100.0 | 100.0 |

Figure 2:
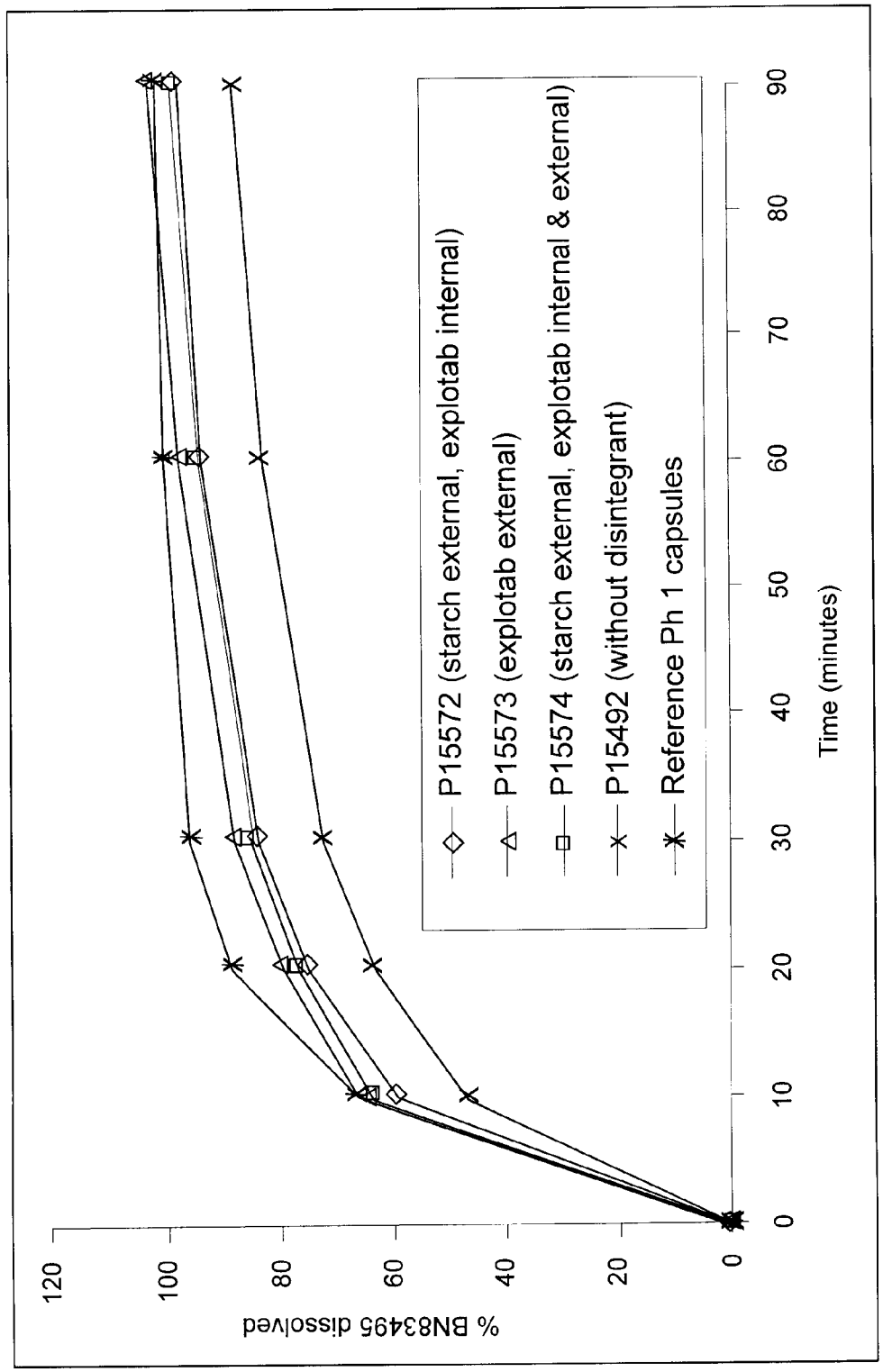
FIG. 2: shows the comparative dissolution curves of different compositions of compound 1 as a function of time. Each curve corresponds to a solid composition containing different disintegration agents.

The results obtained show that the addition of a disintegration agent accelerates the dissolution profile of the tablet making it closer to the reference capsule (cf. FIG. 2).

3. Protective Effect of Binders on the Active Ingredient During the Wet Granulation Process A study demonstrating the protective effect of binder and/or diluent (microcrystalline cellulose, copovidone, carboxymethyl cellulose) was carried out by comparison of the final level of impurity as well as the behaviour of these formulations during their manufacture. Different solid compositions obtained by wet granulation were analyzed by HPLC, on an Alliance 2695 system with 2487 UV detector from Waters (high performance liquid chromatography) according to the conditions described in the table (Table 4) below.

TABLE 4

HPLC analytical method for the analysis of 40 mg tablets of compound I. HPLC method used for the assay of compound I and impurities

| Parameters | Conditions |
|---|---|
| Column | Phenomenex POLAR RP 250 × 4.6 mm - particle sizes 4 μm |
| Elution rate | 1.2 ml/min |
| Temperature of the column | 20 ± 2° C. |
| Detection | UV 215 nm |
| Mobile phase | Isocratic acetonitrile/acidified water (0.1% acid orthophosphoric) 51/49 v/v |
| Analysis time | 15 min |
| Diluent | acetonitrile |
| Reference solution | 0.2 mg/ml in solution in acetonitrile |
| Sample solution | 0.2 mg/ml in acetonitrile |
| Temperature of the samples | Ambient temperature |

TABLE 5

Solid compositions containing compound 1 and using different excipients.

| No. of ref. composition | Micronized Compound 1 5 μm % (m/m) | mannitol % (m/m) | MCC % (m/m) | Lactose % (m/m) | Copovidone % (m/m) | Colloidal silica % (m/m) | Magnesium stearate % (m/m) | Impurities % (m/m) |
|---|---|---|---|---|---|---|---|---|
| 1 | 7 | 31.0 | — | 57.8 | — | 1.4 | 2.8 | 9.9% |
| 2 | 7 | — | 31.0 | 52.8 | 5.0 | 1.4 | 2.8 | 1.4% |
| 17 | 15 | — | 49.2 | 30.0 | 4.2 carboxy- | 0.8 | 0.8 | 1.7% |

TABLE 5-continued

Solid compositions containing compound 1 and using different excipients.

| No. of ref. composition | Micronized Compound 1 5 μm % (m/m) | mannitol % (m/m) | MCC % (m/m) | Lactose % (m/m) | | Colloidal silica % (m/m) | Magnesium stearate % (m/m) | Impurities % (m/m) |
|---|---|---|---|---|---|---|---|---|
| | | | | | methyl cellulose | | | |
| 3 | 7 | — | 31.0 | 52.8 | 5 | 1.4 | 2.8 | 1.1 |

4. Stability of the Tablets Dosed at 5 mg and at 40 mg as a Function of the Storage Conditions, at 6 Months and at 12 Months in Blister Packs A tablet form (centesimal formula of Example 1a) was stabilized after primary packaging in blister packs.

The purpose of this is to check the stability of this form over periods of 6 months and 12 months.

The recommended normal storage conditions are 25° C. and 60% relative humidity (25° C./60% RH) and the data generated under these conditions are shown in Tables 6 and 7 for the tablets dosed at 5 mg and 40 mg respectively.

In addition, other storage conditions (e.g. 40° C./75% RH) were also investigated up to the end of the 6-month stability period and the data generated are shown in Tables 8 and 9 for tablets dosed at 5 mg and 40 mg respectively.

TABLE 6

Stability study on tablets packaged in blister packs containing 5 mg of active ingredient and stored at 25° C./60% RH.

| | Stability scores (months) | | | | |
|---|---|---|---|---|---|
| Tests | initial | 3 | 6 | 9 | 12 |
| Dosage: Compound 1 (mg/unit) | 5.0 | 5.0 | 4.9 | 5.0 | 5.0 |
| Impurities (%) (m/m) | <0.1 | 0.2 | 0.3 | 0.4 | 0.5 |
| Dissolution % compound I dissolved (Min-Max) at time [min] | | | | | |
| 10 minutes | 58-64 | 61-66 | 61-65 | 61-64 | 62-65 |
| 20 minutes | 76-80 | 78-82 | 77-81 | 77-80 | 79-82 |
| 30 minutes | 83-87 | 85-90 | 84-89 | 84-87 | 86-89 |
| 60 minutes | 91-95 | 92-97 | 91-97 | 91-95 | 94-98 |
| 90 minutes | 92-97 | 95-100 | 94-99 | 94-98 | 96-101 |

Table 6 provides a compilation of assay, impurity and dissolution test results from the stability study of tablets packaged in blister packs, containing 5 mg of active ingredient and stored at 25° C./60% RH.

TABLE 7

Stability study of tablets packaged in blister packs, containing 40 mg of active ingredient and stored at 25° C./60% RH.

| | Stability scores (months) | | | | |
|---|---|---|---|---|---|
| Tests | initial | 3 | 6 | 9 | 12 |
| Dosage: Compound 1 (mg/unit) | 38.9 | 39.2 | 38.7 | 39.4 | 39.4 |
| Impurities (%) (m/m) | <0.1 | 0.2 | 0.2 | 0.3 | 0.4 |
| Dissolution % compound I dissolved (Min-Max) at time [min] | | | | | |
| 10 minutes | 62-66 | 63-65 | 64-65 | 63-65 | 64-66 |
| 20 minutes | 77-80 | 77-79 | 77-79 | 78-79 | 78-80 |
| 30 minutes | 83-86 | 84-86 | 83-85 | 84-86 | 84-86 |
| 60 minutes | 90-94 | 91-93 | 91-93 | 91-93 | 92-93 |
| 90 minutes | 93-97 | 94-96 | 93-96 | 94-96 | 95-96 |

Table 7 provides a compilation of assay, impurity and dissolution test results from the stability study of tablets packaged in blister packs, containing 40 mg of active ingredient and stored at 25° C./60% RH.

TABLE 8

Stability study of tablets packaged in blister packs, containing 5 mg of active ingredient and stored under different storage conditions

| | Stability scores (months)/storage conditions | | | |
|---|---|---|---|---|
| Tests | initial | 6 months/ 2-8° C. | 6 months/ 25° C./ 60% RH | 6 months/ 40° C./ 75% RH |
| Dosage: Compound 1 (mg/unit) | 5.0 | 5.0 | 4.9 | 4.8 |
| Impurities (%) (m/m) | <0.1 | <0.1 | 0.3 | 1.9 |
| Dissolution % compound I dissolved (Min-Max) within the time [min] | | | | |
| 10 minutes | 58-64 | 59-65 | 61-65 | 62-65 |
| 20 minutes | 76-80 | 77-82 | 77-81 | 78-82 |
| 30 minutes | 83-87 | 85-89 | 84-89 | 85-89 |
| 60 minutes | 91-95 | 92-98 | 91-97 | 92-98 |
| 90 minutes | 92-97 | 94-100 | 94-99 | 95-100 |

Table 8 provides a compilation of assay, impurity and dissolution test results from the stability study of tablets packaged in blister packs, containing 5 mg of active ingredient and stored under different storage conditions.

TABLE 9

Stability study of the tablets packaged in blister packs containing 40 mg of active ingredient and stored under different storage conditions

| Tests | initial | 6 months/ 2-8° C. | 6 months/ 25° C./ 60% RH | 6 months/ 40° C./ 75% RH |
|---|---|---|---|---|
| Dosage: Compound 1 (mg/unit) | 38.9 | 39.0 | 38.7 | 38.3 |
| Impurities (%) (m/m) | <0.1 | <0.1 | 0.2 | 1.4 |
| Dissolution % compound I dissolved (Min-Max) within the time [min] | | | | |
| 10 minutes | | 62-66 | 62-65 | 64-65 | 62-65 |
| 20 minutes | | 77-80 | 76-78 | 77-79 | 78-79 |
| 30 minutes | | 83-86 | 83-84 | 83-85 | 84-85 |
| 60 minutes | | 90-94 | 90-92 | 91-93 | 91-93 |
| 90 minutes | | 93-97 | 93-94 | 93-96 | 94-95 |

In Table 8 tests of assay, impurities and of dissolution of the stability study of tablets packaged in blister packs containing 40 mg of active ingredient and stored under different storage conditions are grouped together After 12 months' storage at 25° C./60% RH, no significant change was observed for the assay and the dissolution.

Statistical analysis of the results obtained by regression line with a confidence interval of 95% promises at least three years' conformity with the product quality specifications.

The accelerated stabilities at a temperature of 40° C. and 75% relative humidity (40° C./75% RH) show results in conformity with the product quality specifications.

The stability of the product under the most severe conditions reinforces confidence in the projections carried out for the tablets stored at 25° C./60% RH.

5. Preparation of Compound 1 Variety I

5.1 Synthesis of Compound 1

Example 5

The first stage consists of condensing 2-carbetoxycycloheptanone with resorcinol in methanesulphonic acid, the reaction is taken to 25° C. for 4 hours. The intermediate 3-hydroxy-8,9,10,11-tetrahydrocyclohepta[c]chromen-6 (7H)-one thus formed precipitates by adding ethanol then water then it is isolated by filtration, dried under vacuum at 60° C. and a yield of 78% is obtained. In a second stage, sulphonylisocyanate chloride is converted, in toluenic solution, to sulphamoyl chloride by the action of the formic acid, then condensed with the previous intermediate dissolved in N,N-dimethylacetamide (DMA). The reaction medium is treated with water and extracted with 2-methyltetrahydrofurane (2-MeTHF). The crude compound 1 is then obtained by filtration of the precipitate obtained by adding methylcyclohexane to the organic phase. Finally, pure compound 1 is obtained by recrystallization of the crude product by dissolution in acetone while hot and precipitation by adding methylcyclohexane (the addition of the antisolvent methylcyclohexane having the main purpose of increasing the yield).

Compound 1 is thus obtained with a yield of 65%, and presented hereafter.

Example 1 thus obtained can be subjected to an appropriate treatment aimed at reducing the size of the particles such as micronization (point 5.3 below) or wet grinding (point 5. below).

5.2 Desolvation of the DMSO Solvate of Form 2 of Compound 1 in Water

Example 5a

DMSO Solvate of Form 2 of Compound 1

1 mL of DMSO (Bp=189° C.) is poured into a pill box, then 1 g of compound 1 (Example 1) is added. The solution is stirred using a magnetic stirring bar and a magnetic stirrer. The solid passes into solution rapidly. 1 g of compound 1 is again added, still under magnetic stirring. The solid partly dissolves, then caking is observed. A sample of the caking is analyzed while still moist by X-ray powder diffraction. This analysis, presented hereafter, shows that this is the DMSO solvate of form 2 of compound 1 (Example 5a).

Example 5b

The DMSO solvate of form 2 of compound 1 (Example 5b) is immersed in cold water and left under stirring for five minutes at ambient temperature. The suspension is then filtered and dried.

Compound 1 is thus obtained with a yield of 50% and presented hereafter.

Example 5b thus obtained can be subjected to an appropriate treatment aimed at reducing the size of the particles such as micronization or wet grinding.

5.3 Micronization

Micronization is carried out using a compressed air-jet micronizer at a temperature comprised between 18 and 25° C. The characteristics of the compressed air used are the following:

CO: <5 ppm,
$CO_2$: <500 ppm,
Hydrocarbons: <0.5 mg·m$^{-3}$,
Number of particles per ft$^3$>0.5μ: <10000,
Maximum performance: 2300 cfm at 13 bar,
Maximum operating pressure: 13 bar.

Example 5c

Variety I of Compound 1 with a Particle Size 3 μm 249 g of compound 1 (Example 1) are micronized using a compressed air-jet micronizer. The micronization parameters are: a Venturi pressure of 80 psi, a pressure of the micronizer of 110 psi and a feed rate of 12 kg·h$^{-1}$.

Example 3-1 is thus obtained with a yield of 97%.

Example 5d

Variety I of Compound 1 with a Particle Size 5 μm 16.5 kg of compound 1 (Example 5) are micronized using a compressed air-jet micronizer. The micronization parameters are: a Venturi pressure of 80 psi, a pressure of the micronizer of 32 psi and a feed rate 0114.4 kg·h$^{-1}$.

Example 5d is thus obtained with a yield of 98% and presented hereafter.

Example 5e

Variety I of Compound 1 with a Particle Size 9 μm 150 g of compound 1 (Example 51) are micronized using a compressed air-jet micronizer. The micronization parameters are: a Venturi pressure of 50 psi, a pressure of the micronizer of 60 psi and a feed rate of 15 kg·h$^{-1}$.

Example 5e is thus obtained with a yield of 98%.

Example 5f

Variety I of Compound 1 with a Particle Size 15 μm 39 g of compound 1 (Example 5) are micronized using a compressed air-jet micronizer. The micronization parameters are: a Venturi pressure of 30 psi, a pressure of the micronizer of 10 psi and a feed rate of 40 g in 15 minutes.

Example 5f is thus obtained with a yield of 74%.

5.4 Wet Grinding

Example 5g 0.69 g of compound 1 (Example 5) are ground with 0.068 g of methylcyclohexane in a Fritsch type planetary model P4 ball mill.

The wet grinding parameters are: 7 agate balls 10 mm in diameter, a grinding torque Ω (speed of rotation of the disc)–ω (speed of rotation of the flasks) of 100-100 rpm, a period of 12 effective hours out of a total of 18 hours according to the following 72 sequences: 10 minutes of grinding—5 minutes' pause, a mass of balls/mass of solute ratio of 14.1; a temperature of 22° C. and a mass of compound 1/mass of methylcyclohexane ratio of 9%.

Example 3 is thus obtained with a yield of 99% and presented hereafter.

6. Description of the Crystals Obtained 6.1 Equipment Used
6.1.1 X-Ray Powder and Single Crystal Diffraction
Siemens D5005 diffractometer, scintillation detector
  Wavelength: 1.54056 Cu, voltage 40 KV, intensity 40 mA
  Measurement range: 3°-30°2 theta
  Interval: 0.04°2 theta
  Duration of the interval: 4s
  Fixed slots: 1.6 mm
  Kβ filter (Ni)
  Without internal reference
  EVA software (v 12.0) for data processing
Smart Apex Bruker diffractometer, two-dimensional detector
  SMART software for determination of the parameters and orientation of the crystal matrix
  SAINT software for data integration and processing
  WinGX software for determination of the space group and the structural resolution
6.1.2 DSC
  Netzsch DSC 204F1
  Aluminium crucible and pierced lid
  Atmosphere: Helium
  Initial temperature: 20° C.
  Final temperature: 200° C.
  Temperature gradient: 5° C.·min$^{-1}$
6.1.3 IR
  KBr pellet
  Bruker IFS28 type spectrometer
  Spectral range: 400-4000 cm$^{-1}$
6.1.4 NMR of the solid
  Bruker Avance 500 MHz spectrometer
  MAS (Magic Angle Spinning) 4 mm probe
  Bruker XwinNMR software
  VACP (Variable Amplitude Cross-Polarization) with MAS (11 kHz) and proton decoupling (spinal 64, 65 kHz)
  External reference: Adamantane
6.1.5 Particle Size Distribution
  Malvern Mastersizer S laser granulometer
  Size of the sample: 30 to 50 mg
  Dispersion medium: 0.50% (m/v) Nonidet in water
  Mie theory with as refractive indices: particle RI=1.55; imaginary RI=1.00; dispersant RI=1.38
  Sonication time: 60 seconds
  Sonication energy: 50 to 60 Hz
  Recirculation time: 30 seconds at 2000 rpm$^{-1}$
  Obscuration: 15-25%
6.2 Characterization of the Examples
6.2.1 Examples 5 and 5b It has been possible to isolate single crystals by slow evaporation of a saturated solution in ethanol at 4° C. for 2 days. These single crystals have made it possible to resolve the complete structure of variety I of compound 1 by X-ray diffraction.

X-ray single crystal diffraction: the crystalline structure of compound 1 variety I has been resolved and exhibits the following cell parameters:

| | |
|---|---|
| Cell structure | Monoclinic |
| Space group | P2$_1$/c (no. 14) |
| Cell parameter a | 11.995(5) Å |
| Cell parameter b | 11.236(5) Å |
| Cell parameter c | 10.403(5) Å |
| Cell parameter α | 90° |
| Cell parameter β | 99.09° |
| Cell parameter γ | 90° |
| Cell volume | 1384.5(10) Å$^3$ |
| Number of molecules per cell: Z | 4 |
| Calculated density | 1.484 g · cm$^{-3}$ |

The reduced coordinates (×10$^4$) and equivalent isotropic displacement parameters (Å$^2$×10$^3$) of compound 1 variety I are the following:

| | X | Y | Z | U(eq) |
|---|---|---|---|---|
| C(1) | 8517(2) | 4055(2) | 6064(2) | 49(1) |
| C(2) | 9769(2) | 4143(2) | 6671(2) | 48(1) |
| C(3) | 10572(2) | 3420(2) | 5997(2) | 54(1) |
| C(4) | 10389(2) | 2096(2) | 5973(3) | 55(1) |
| C(5) | 9230(2) | 1711(2) | 5284(2) | 52(1) |
| C(6) | 8303(2) | 1868(2) | 6098(2) | 40(1) |
| C(7) | 7962(1) | 2946(2) | 6473(2) | 39(1) |
| C(8) | 7097(1) | 3009(2) | 7309(2) | 38(1) |
| C(9) | 6675(1) | 1951(2) | 7734(2) | 37(1) |
| C(10) | 7790(1) | 791(2) | 6485(2) | 40(1) |
| C(11) | 6681(2) | 4058(2) | 7781(2) | 48(1) |
| C(12) | 5914(2) | 4037(2) | 8627(2) | 50(1) |
| C(13) | 5561(2) | 2959(2) | 9052(2) | 41(1) |
| C(14) | 5924(2) | 1896(2) | 8619(2) | 41(1) |
| N | 2943(1) | 2531(2) | 8742(2) | 47(1) |
| O(1) | 7012(1) | 872(1) | 7312(1) | 45(1) |
| O(2) | 8002(1) | −206(1) | 6149(2) | 54(1) |
| O(3) | 4881(1) | 3037(1) | 10036(1) | 53(1) |
| O(4) | 3320(1) | 2749(1) | 11088(1) | 58(1) |
| O(6) | 4066(1) | 1037(1) | 10021(2) | 69(1) |
| S(1) | 3768(1) | 2248(1) | 10030(1) | 41(1) |

The reduced coordinates of the hydrogen atoms (×10⁴) of compound 1 variety I are the following:

|        | x        | Y        | Z        | U(eq)  |
|--------|----------|----------|----------|--------|
| H(11)  | 6924(18) | 4720(20) | 7470(20) | 55(6)  |
| H(12)  | 5679(19) | 4770(20) | 8940(20) | 63(6)  |
| H(14)  | 5738(17) | 1098(19) | 8870(20) | 54(6)  |
| H(1A)  | 8120(18) | 4743(19) | 6260(20) | 55(6)  |
| H(2A)  | 9964(17) | 4984(19) | 6657(19) | 53(6)  |
| H(3A)  | 11368(19)| 3541(19) | 6340(20) | 60(6)  |
| H(4A)  | 10960(20)| 1750(20) | 5580(20) | 68(7)  |
| H(5A)  | 9062(19) | 2184(19) | 4450(20) | 61(7)  |
| H(1B)  | 8421(19) | 4050(19) | 5070(20) | 66(6)  |
| H(2B)  | 9894(16) | 3890(17) | 7600(20) | 48(5)  |
| H(3B)  | 10467(17)| 3666(18) | 5110(20) | 53(6)  |
| H(4B)  | 10461(19)| 1776(19) | 6860(20) | 61(7)  |
| H(5B)  | 9219(19) | 900(20)  | 5100(20) | 63(7)  |
| H(1N)  | 2770(20) | 3270(20) | 8750(20) | 68(8)  |
| H(2N)  | 3240(20) | 2300(20) | 8060(20) | 72(8)  |

The interplanar spacings of compound 1 variety I are the following:

| H  | K | L | 2Theta/deg | d/Å   | I/rel, | |F(hkl)| |
|----|---|---|------------|-------|--------|---------|
| 1  | 0 | 0 | 7.46       | 11.84 | 53.58  | 69.88   |
| 1  | 1 | 0 | 10.85      | 8.15  | 11.9   | 33.95   |
| -1 | 1 | 1 | 13.10      | 6.75  | 3.97   | 23.76   |
| 1  | 1 | 1 | 14.58      | 6.07  | 2.02   | 18.88   |
| 2  | 0 | 0 | 14.95      | 5.92  | 2.18   | 28.47   |
| 0  | 2 | 0 | 15.76      | 5.62  | 66.66  | 166.12  |
| 2  | 1 | 0 | 16.91      | 5.24  | 16.31  | 62.45   |
| 0  | 0 | 2 | 17.25      | 5.14  | 6.51   | 56.96   |
| 1  | 2 | 0 | 17.46      | 5.08  | 22.31  | 75.46   |
| -1 | 0 | 2 | 17.69      | 5.01  | 17.58  | 96      |
| -2 | 1 | 1 | 17.88      | 4.96  | 6.14   | 40.56   |
| 0  | 1 | 2 | 18.98      | 4.67  | 10.23  | 55.68   |
| 1  | 2 | 1 | 20.01      | 4.43  | 6.69   | 47.56   |
| 1  | 1 | 2 | 21.41      | 4.15  | 100    | 197.19  |
| -2 | 1 | 2 | 22.47      | 3.95  | 26.25  | 106.22  |
| 3  | 0 | 0 | 22.50      | 3.95  | 8.86   | 87.39   |
| -2 | 2 | 1 | 22.56      | 3.94  | 7.86   | 58.39   |
| 0  | 2 | 2 | 23.45      | 3.79  | 13.11  | 78.51   |
| 3  | 1 | 0 | 23.87      | 3.72  | 2.91   | 37.71   |
| 2  | 0 | 2 | 24.65      | 3.61  | 40.18  | 204.83  |
| 1  | 3 | 0 | 24.91      | 3.57  | 16.69  | 94.37   |
| 1  | 2 | 2 | 25.47      | 3.49  | 6.03   | 58.08   |
| 2  | 1 | 2 | 25.91      | 3.44  | 23.6   | 116.99  |
| -3 | 0 | 2 | 26.19      | 3.40  | 3.64   | 65.73   |
| -2 | 2 | 2 | 26.38      | 3.38  | 2.42   | 38.19   |
| 3  | 1 | 1 | 26.62      | 3.35  | 6.43   | 62.81   |
| 3  | 2 | 0 | 27.59      | 3.23  | 6.14   | 63.74   |
| -3 | 2 | 1 | 27.84      | 3.20  | 4.33   | 54.08   |
| 2  | 3 | 0 | 28.17      | 3.17  | 4.87   | 58.06   |
| -2 | 3 | 1 | 28.78      | 3.10  | 2.52   | 42.75   |
| 1  | 1 | 3 | 29.35      | 3.04  | 3.06   | 48.04   |
| 2  | 2 | 2 | 29.40      | 3.04  | 2.08   | 39.73   |

6.2.2 Example 5a

It was possible to isolate single crystals by slow evaporation of a saturated solution of DMSO at ambient temperature. These single crystals made it possible to resolve the complete structure of the DMSO solvate of form 2 of compound 1 by X-ray diffraction.

Single crystal X-ray diffraction: The crystalline structure of the DMSO solvate of form 2 of compound 1 was resolved and exhibits the following cell parameters:

| Cell structure     | Monoclinic              |
|--------------------|-------------------------|
| Space group        | C2/c (no. 15)           |
| Cell parameter a   | 28.713(2) Å             |
| Cell parameter b   | 9.399(7) Å              |
| Cell parameter c   | 16.6487(12) Å           |
| Cell parameter β   | 126.015(9)°             |
| Cell volume        | 3634(3) Å³              |
| Z, Z'              | 8, 1                    |
| Calculated density | 1.416 g · cm⁻³          |

The atomic coordinates of the atoms in the cell (×10⁴) and equivalent isotropic displacement parameters (Å²×10³) (U(eq) equals a third of the value of the orthogonal tensor Uij) of the DMSO solvate of form 2 of compound 1 are the following:

|        | x         | Y         | Z         | U(eq)   |
|--------|-----------|-----------|-----------|---------|
|        |           | DMSO      |           |         |
| S(1S)  | 2081(1)   | 5757(4)   | 1369(3)   | 94(1)   |
| O(1S)  | 2139(4)   | 5214(12)  | 2274(8)   | 134(4)  |
| C(1S)  | 2694(6)   | 6782(14)  | 1798(12)  | 115(5)  |
| C(2S)  | 2252(6)   | 4239(14)  | 912(13)   | 114(5)  |
|        |           | compound 1|           |         |
| S(1)   | 1113(1)   | 7393(3)   | 2439(2)   | 73(1)   |
| O(1)   | -859(2)   | 4386(7)   | 1159(5)   | 65(2)   |
| O(2)   | 705(3)    | 6637(7)   | 1385(5)   | 75(2)   |
| O(3)   | -1629(3)  | 3534(7)   | 975(6)    | 78(2)   |
| O(4)   | 788(4)    | 7592(8)   | 2833(7)   | 89(2)   |
| O(5)   | 1316(4)   | 8561(8)   | 2190(6)   | 97(3)   |
| N(1)   | 1623(4)   | 6326(9)   | 3100(6)   | 74(2)   |
| C(1)   | 433(4)    | 5393(11)  | 1383(7)   | 67(3)   |
| C(2)   | -81(4)    | 5473(10)  | 1307(7)   | 62(2)   |
| C(3)   | -349(4)   | 4271(10)  | 1238(7)   | 55(2)   |
| C(4)   | -144(4)   | 2931(9)   | 1268(7)   | 52(2)   |
| C(5)   | 390(4)    | 2899(10)  | 1371(7)   | 62(3)   |
| C(6)   | 665(4)    | 4097(11)  | 1428(7)   | 68(3)   |
| C(7)   | -1196(4)  | 3258(10)  | 1019(7)   | 61(2)   |
| C(8)   | -992(4)   | 1858(10)  | 995(8)    | 60(2)   |
| C(9)   | -477(4)   | 1725(8)   | 1161(6)   | 49(2)   |
| C(10)  | -266(4)   | 209(9)    | 1168(7)   | 66(3)   |
| C(11)  | -585(4)   | -447(11)  | 169(7)    | 69(3)   |
| C(12)  | -1167(5)  | -1113(14) | -192(10)  | 89(4)   |
| C(13)  | -1582(5)  | -65(12)   | -242(9)   | 86(4)   |
| C(14)  | -1408(5)  | 699(12)   | 721(10)   | 86(3)   |

The coordinates of the hydrogen atoms (×10⁴) and equivalent isotropic displacement parameters (Å²×10³) (U(eq) equals a third of the value of the orthogonal tensor Uij) of the DMSO solvate of form 2 of compound 1 are the following:

|         | x     | Y     | Z     | U(eq) |
|---------|-------|-------|-------|-------|
|         |       | DMSO  |       |       |
| H(1S1)  | 2689  | 7616  | 2126  | 172   |
| H(1S2)  | 2697  | 7060  | 1247  | 172   |
| H(1S3)  | 3032  | 6232  | 2258  | 172   |
| H(2S1)  | 2582  | 3754  | 1460  | 172   |
| H(2S2)  | 2335  | 4560  | 461   | 172   |
| H(2S3)  | 1930  | 3599  | 573   | 172   |
|         |       | compound 1 |  |       |
| H(2)    | -232  | 6351  | 1304  | 75    |
| H(5)    | 550   | 2024  | 1399  | 75    |
| H(6)    | 1011  | 4045  | 1496  | 82    |
| H(10A)  | 140   | 250   | 1442  | 79    |
| H(10B)  | -305  | -390  | 1599  | 79    |
| H(11A)  | -345  | -1179 | 174   | 83    |

-continued

| | x | Y | Z | U(eq) |
|---|---|---|---|---|
| H(11B) | −652 | 273 | −305 | 83 |
| H(12A) | −1342 | −1518 | −846 | 107 |
| H(12B) | −1101 | −1882 | 253 | 107 |
| H(13A) | −1940 | −563 | −505 | 103 |
| H(13B) | −1661 | 662 | −721 | 103 |
| H(14A) | −1750 | 1087 | 628 | 103 |
| H(14B) | −1239 | 14 | 1259 | 103 |

The interplanar spacings of the DMSO solvate of form 2 of compound 1 are the following:

| H | K | L | 2Theta/deg | d/Å | I/rel, | |F(hkl)| |
|---|---|---|---|---|---|---|
| 2 | 0 | 0 | 7.61 | 11.61 | 93.62 | 158.42 |
| 1 | 1 | 0 | 10.15 | 8.71 | 44.56 | 103.26 |
| −2 | 0 | 2 | 10.62 | 8.32 | 5.71 | 54.77 |
| −1 | 1 | 1 | 10.80 | 8.18 | 10.04 | 52.22 |
| −4 | 0 | 2 | 13.01 | 6.80 | 9.86 | 88.39 |
| 0 | 0 | 2 | 13.14 | 6.73 | 24.61 | 141 |
| −3 | 1 | 1 | 13.19 | 6.71 | 75.41 | 175.25 |
| 1 | 1 | 1 | 13.26 | 6.67 | 58.06 | 154.51 |
| 4 | 0 | 0 | 15.25 | 5.81 | 8.76 | 97.89 |
| −5 | 1 | 2 | 18.19 | 4.87 | 39.9 | 176.99 |
| 1 | 1 | 2 | 18.33 | 4.84 | 72.53 | 240.47 |
| −6 | 0 | 2 | 18.53 | 4.78 | 41.04 | 258.66 |
| −3 | 1 | 3 | 18.55 | 4.78 | 24.52 | 141.58 |
| −5 | 1 | 1 | 18.68 | 4.75 | 21.01 | 131.96 |
| 2 | 0 | 2 | 18.71 | 4.74 | 8.13 | 116.24 |
| 3 | 1 | 1 | 18.77 | 4.72 | 6.81 | 75.49 |
| −2 | 2 | 1 | 19.97 | 4.44 | 27.29 | 161.17 |
| 0 | 2 | 1 | 20.00 | 4.44 | 4.3 | 64.06 |
| −5 | 1 | 3 | 20.02 | 4.43 | 50.8 | 220.36 |
| −1 | 1 | 3 | 20.14 | 4.41 | 33.54 | 180.21 |
| 2 | 2 | 0 | 20.37 | 4.36 | 5.62 | 74.65 |
| 5 | 1 | 0 | 21.32 | 4.16 | 24.81 | 164.42 |
| −4 | 0 | 4 | 21.33 | 4.16 | 58.24 | 356.44 |
| −2 | 2 | 2 | 21.70 | 4.09 | 10.75 | 110.24 |
| −4 | 2 | 1 | 22.73 | 3.91 | 2.86 | 59.66 |
| −2 | 0 | 4 | 22.75 | 3.91 | 32.04 | 282.72 |
| 6 | 0 | 0 | 22.96 | 3.87 | 3.7 | 96.94 |
| −4 | 2 | 2 | 22.99 | 3.87 | 55.47 | 265.91 |
| 0 | 2 | 2 | 23.06 | 3.85 | 30.27 | 197.08 |
| −5 | 1 | 4 | 23.64 | 3.76 | 2.09 | 53.09 |
| −7 | 1 | 2 | 23.79 | 3.74 | 2.79 | 61.84 |
| 3 | 1 | 2 | 23.96 | 3.71 | 9.87 | 117.16 |
| −7 | 1 | 3 | 24.00 | 3.71 | 11.93 | 128.99 |
| 1 | 1 | 3 | 24.21 | 3.67 | 100 | 376.83 |
| 4 | 2 | 0 | 24.35 | 3.65 | 22.95 | 181.63 |
| −8 | 0 | 2 | 25.26 | 3.52 | 14.41 | 211.56 |
| 4 | 0 | 2 | 25.46 | 3.50 | 2.89 | 95.47 |
| 5 | 1 | 1 | 25.48 | 3.49 | 9.78 | 124.38 |
| −7 | 1 | 4 | 25.97 | 3.43 | 3.4 | 74.81 |
| −1 | 1 | 4 | 26.17 | 3.40 | 38.29 | 253.11 |
| −8 | 0 | 4 | 26.20 | 3.40 | 4.21 | 118.77 |
| 0 | 0 | 4 | 26.45 | 3.37 | 22.75 | 279.11 |
| −6 | 2 | 3 | 27.32 | 3.26 | 2.61 | 69.16 |
| 4 | 2 | 1 | 27.54 | 3.24 | 3.15 | 76.69 |
| −5 | 1 | 5 | 28.42 | 3.14 | 5.77 | 107.23 |
| 7 | 1 | 0 | 28.51 | 3.13 | 18.44 | 192.32 |
| −1 | 3 | 1 | 28.98 | 3.08 | 5.27 | 104.63 |
| −7 | 1 | 5 | 29.39 | 3.04 | 2.61 | 74.74 |
| −3 | 1 | 5 | 29.53 | 3.02 | 15.12 | 180.83 |
| 3 | 1 | 3 | 29.81 | 3.00 | 2.86 | 79.49 |
| 6 | 2 | 0 | 29.88 | 2.99 | 4.93 | 104.61 |

The X-ray powder diffraction diagram of DMSO solvate of form 2 of compound 1 exhibits the following characteristic peaks expressed as an angle (°2 theta) to approximately ±0.1°2 theta: (FIGS. 1 and 2). 7.6; 18.7; 24.2; 29.9.

Figure 5:
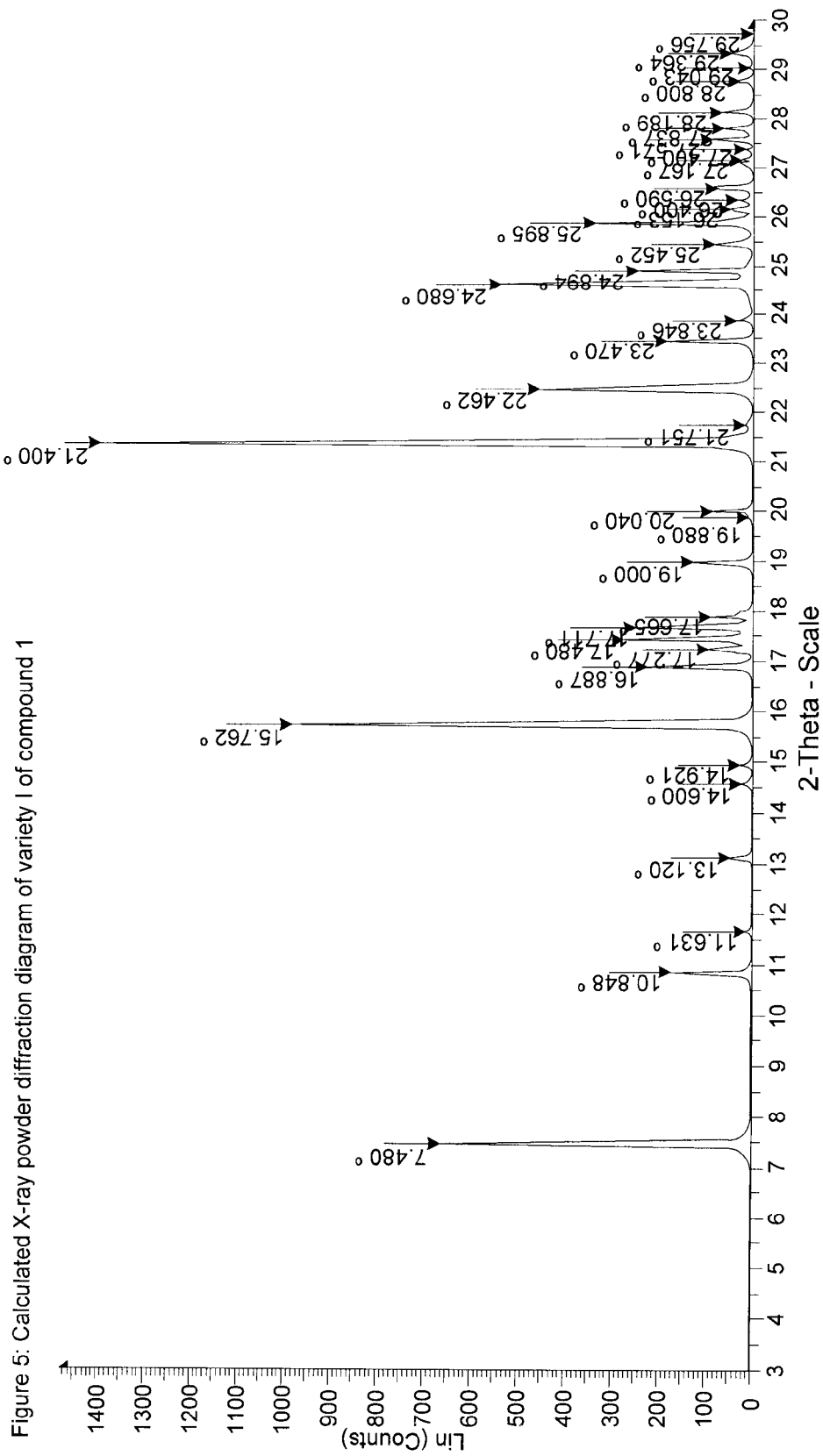
FIG. 5: calculated X-ray powder diffraction diagram of variety I of compound 1

6.2.3 Examples 5c-5g 6.2.3.1 X-Ray Powder Diffraction (FIGS. 5 and 6)

The X-ray powder diffraction diagram of variety I of compound 1 after micronization or wet grinding exhibits the following characteristic peaks expressed as an angle (°2 theta) to approximately ±0.1°2 theta: 7.5; 10.9; 11.7; 13.1; 14.6; 15.0; 15.8; 17.0; 17.3; 17.5; 17.7; 17.9; 19.0; 19.9; 20.0; 21.4; 21.8; 22.5; 23.5; 23.9; 24.7; 24.9; 25.5; 25.9; 26.2; 26.4; 26.6; 27.2; 27.4; 27.6; 27.8; 28.2; 28.8; 29.0; 29.4; 29.8.

The X-ray powder diffraction diagram of variety I of compound 1 after micronization or wet grinding and then heating to 160° C. exhibits the following characteristic peaks expressed as an angle (°2 theta) to approximately ±0.1°2 theta: 7.5; 10.9; 11.7; 13.1; 14.6; 15.0; 15.8; 17.0; 17.3; 17.5; 17.7; 17.9; 19.0; 19.9; 20.0; 21.4; 21.8; 22.5; 23.5; 23.9; 24.7; 24.9; 25.5; 25.9; 26.2; 26.4; 26.6; 27.2; 27.4; 27.6; 27.8; 28.2; 28.8; 29.0; 29.4; 29.8 without additional peaks corresponding to the novel form produced during heating to 160° C.

6.2.3.2 DSC (FIG. 7)

Using DSC, the thermogram obtained at 5° C.·min$^{-1}$ of variety I of compound 1 after micronization or wet grinding comprises the melting peak of variety I (onset 170°±5° C.), optionally a small melting peak of a novel polymorphic form produced during analysis (onset 180±2° C.) representing less than 10% of the enthalpy exchanged during the melting peak of variety I and does not exhibit any endothermic event (or less than 0.5 J/g) between 140-155° C.

6.2.3.3 IR (FIG. 8)

The IR spectrum of variety I of compound 1 after micronization or wet grinding exhibits the characteristic peaks expressed in cm$^{-1}$ to approximately ±5 cm$^{-1}$: 3310; 3167; 3059; 2928; 2858; 1690; 1605; 1454; 1385; 1261; 1188; 1126; 941; 891; 853; 798; 733; 679; 598; 544; 455.

6.2.3.4 NMR of the Solid (FIG. 9)

The spectrum of variety I of compound 1 after micronization or wet grinding obtained by NMR of the solid exhibits the following characteristic peaks expressed in ppm to approximately ±0.2 ppm 163.1; 156.1; 153.8; 153.1; 130.4; 127.6; 107.6; 35; 25.

6.2.3.5 Particle Size

The particle size distribution of variety I of compound 1 after micronization according to Example 2-2 is the following: D10(%)=1.2 µm; D50(%)=5.2 µm and D90(%)=11.0 µm.

The particle size distribution of variety I of compound 1 after wet grinding according to Example 3 is the following: D10(%)=0.6 µm; D50(%)=3.1 µm and D90(%)=13.7 µm.

7. Formulation 7.1 Formulation in the Form of Gelatin Capsules

Variety I of compound 1 according to the invention, can be formulated in a gelatin capsule containing: 5 to 30% active ingredient (preferably 6 to 13%), 40 to 92% diluent (preferably 65 to 92%, very preferably 85 to 90%), 0 to 30% disintegration agent (preferably 0 to 22%, very preferably 0%), 0 to 5% surfactant (preferably 0%), 0 to 5% solubilizant (preferably 0%), 0.1 to 3% flow agent (preferably 0.9 to 1.4%), 0.5 to 3% lubricant (preferably 0.6 to 2.8%).

The preferred excipients for formulating these gelatin capsules are mannitol, lactose, corn starch, colloidal silica, magnesium stearate, and sodium lauryl sulphate, and more particularly mannitol, lactose, colloidal silica, and magnesium stearate.

The gelatin capsules presented below were manufactured by mixing powder according to the standard techniques known to a person skilled in the art.

| Ex | Ex 5d | M | L | CS | SLS | PEG | CS | MS |
|----|-------|------|------|------|------|------|------|------|
| 7a | 6.0% | 87.2% | / | / | 4.8% | / | 1.3% | 0.7% |
| 7b | 6.0% | 87.2% | / | / | / | 4.8% | 1.3% | 0.7% |
| 7c | 6.0% | 43.6% | 43.6% | / | 4.8% | / | 1.3% | 0.7% |
| 7d | 6.0% | 43.6% | 43.6% | / | / | 4.8% | 1.3% | 0.7% |
| 7e | 12.3% | 65.0% | 21.2% | / | / | / | 0.9% | 0.6% |
| 7f | 12.3% | / | 65.0% | 21.2% | / | / | 0.9% | 0.6% |
| 7g | 7.0% | 31.0% | 57.8% | / | / | / | 1.4% | 2.8% |
| 7h | 6.0% | 92.0% | / | / | / | / | 1.3% | 0.7% |
| 7i | 6.0% | 46.0% | 46.0% | / | / | / | 1.3% | 0.7% |

M = mannitol;
L = lactose;
CS = Corn starch;
SLS = Sodium lauryl sulphate;
PEG = polyethylene glycol;
CS = colloidal silica;
MS = magnesium stearate

Example 7j the example of gelatin capsules 7j is prepared from compound 1 of Example 5: 40 mg of compound 1 are mixed with 260 mg of lactose and placed in gelatin capsules.

Example 7k the example of gelatin capsules 7k is prepared according to formula 7g with Example 5c as active ingredient instead of Example 5d.

Example 7l the example of gelatin capsules 7l is prepared with 7.2% example 5d, 31.9% mannitol, 59.4% lactose and 1.5% colloidal silica.

Example 7m the example of gelatin capsules 7m is prepared according to formula 7g with Example 5d as active ingredient.

Example 7n the example of gelatin capsules 4n is prepared according to formula 4g with Example 5e as active ingredient instead of Example 5d.

Example 7o the example of gelatin capsules 4o is prepared with Example 5f as active ingredient: 40 mg of Example 5f are mixed with 260 mg of lactose and placed in gelatin capsules.

7.2 Formulation in the Form of Tablets

Variety I of compound 1 according to the invention, can be formulated in a tablet containing: 5 to 30% active ingredient (preferably 7 to 20% and very preferably 10 to 15%), 40 to 92% diluent (preferably 34 to 89% and very preferably 70 to 85%), 0 to 40% disintegration agent (preferably 0 to 20% and very preferably 3 to 5%), 0 to 8% binding agent (preferably 2 to 5%), 0.1 to 3% flow agent (preferably 0.5 to 1.4%), 0.5 to 3% lubricant (preferably 0.5 to 2.8%).

The preferred excipients for formulating these gelatin capsules are maltodextrin, mannitol, microcrystalline cellulose, lactose, corn starch, sodium starch glycolate, crospovidone, polyvinylpyrrolidone, carboxymethyl cellulose, colloidal silica, magnesium stearyl fumarate, and magnesium stearate and more particularly microcrystalline cellulose, lactose, sodium starch glycolate, polyvinylpyrrolidone, colloidal silica, and magnesium stearate.

The tablets presented below were manufactured by wet granulation according to the standard techniques known to a person skilled in the art.

| Example/Excipient | % Example 5d | % Maltodextrin | % Mannitol | % Microcrystalline cellulose | % Lactose | % Corn starch | % Sodium starch glycolate | % Polyvinylpolypyrrolidone | % Polyvinylpyrrolidone | % Carboxymethylcellulose | % Colloidal silica | % Sodium stearyl fumarate | % Magnesium stearate |
|---|---|---|---|---|---|---|---|---|---|---|---|---|---|
| 7aa | 7.0 | / | 31.0 | / | 57.8 | / | / | / | / | / | 1.4 | / | 2.8 |
| 7ab | 7.0 | / | 31.0 | / | 52.8 | / | / | / | 5.0 | / | 1.4 | / | 2.8 |
| 7ac | 7.0 | / | 31.0 | / | 52.8 | / | / | / | / | 5.0 | 1.4 | / | 2.8 |
| 7ad | 20.0 | / | / | 44.2 | 28.3 | / | / | / | 4.2 | / | 0.8 | / | 2.5 |
| 7ae | 15.0 | / | 36.0 | / | 41.5 | 3.0 | / | / | 3.0 | / | 1.0 | / | 0.5 |
| 7af | 15.0 | 27.5 | 26.0 | 25.0 | / | 5.0 | / | / | / | / | 1.0 | / | 0.5 |
| 7ag | 15.0 | 26.5 | / | 25.0 | 26.0 | 6.0 | / | / | / | / | 1.0 | / | 0.5 |
| 7ah | 15.0 | 18.0 | / | 20.0 | 40.0 | 4.5 | / | / | / | / | 1.0 | / | 1.5 |
| 7ai | 15.0 | 8.0 | / | 10.0 | 45.0 | 15.5 | 4.0 | / | / | / | 1.0 | / | 1.5 |
| 7aj | 15.0 | 14.5 | / | 20.0 | / | 40.0 | / | / | 8.0 | / | 1.0 | / | 1.5 |
| 7ak | 10.0 | / | / | 45.0 | 36.5 | / | 4.0 | / | 3.0 | / | 0.5 | / | 1.0 |
| 7al | 15.0 | 30.5 | / | 10.0 | 35.0 | 5.0 | / | / | 2.0 | / | 1.0 | / | 1.5 |
| 7am | 15.0 | / | / | 12.5 | 35.0 | 35.0 | / | / | / | / | 1.0 | / | 1.5 |
| 7an | 15.0 | / | / | 39.2 | 21.7 | / | 16.7 | / | 4.2 | / | 0.8 | / | 2.5 |
| 7ao | 15.0 | / | / | 46.7 | 30.8 | / | / | / | 4.2 | / | 0.8 | 2.5 | / |
| 7ap | 15.0 | / | / | 45.8 | 30.0 | / | / | 1.7 | 4.2 | / | 0.8 | / | 2.5 |
| 7aq | 15.0 | / | / | 49.2 | 30.0 | / | / | / | 4.2 | / | 0.8 | / | 0.8 |
| 7ar | 15.0 | / | / | 46.7 | 30.8 | / | / | / | 4.2 | / | 0.8 | / | 2.5 |
| 7s | 10.0 | / | / | 37.0 | 37.0 | 10.0 | 4.0 | / | / | / | 1.0 | / | 1.0 |

8. Physico-Chemical and Biological Properties

8.1 Dissolution Kinetics

The dissolution kinetics (expressed as a percentage of compound 1 dissolved as a function of time) are measured according to the standard techniques known to a person skilled in the art, and presented in the table below.

| Time (min.) | Example 7j | Example 7k | Example 7l | Example 7n | Example 7o |
|---|---|---|---|---|---|
| 0 | 0% | 0% | 0% | 0% | 0% |
| 10 | 4.3% | 58.0% | 53.1% | 58.0% | 46.9% |
| 20 | 7.8% | 78.1% | 82.0% | 84.5% | 65.6% |
| 30 | 10.6% | 84.8% | 93.8% | 92.6% | 73.7% |
| 60 | 15.7% | 94.3% | 102.6% | 100.8% | 82.7% |
| 90 | 18.8% | 98.0% | 104.6% | 105.1% | 87.5% |

The above dissolution results are expressed as a percentage of theoretical strength. The theoretical strength in gelatin capsules 4j to 4n is 40 mg of active ingredient. These examples are experimental, a slight excess of active ingredient during weighing is possible and explains percentages greater than 100% at the final dissolution point.

8.2 Bioavailability

The comparative bioavailability of compound 1 was studied in dogs after a single administration of two gelatin capsules by oral route. The blood samples are taken 1; 1.5; 2; 4; 6; 9; 12; 24; 30 and 48 hours after administration. The area under the curve (AUC) is one of the pharmacokinetic parameters measured in the samples of plasma from the dogs. The results obtained are presented in the table below

| Example | AUC (ng · mL$^{-1}$ · h) |
|---|---|
| Example 4k | 826 |
| Example 4l | 844 |
| Example 4m | 806 |
| Example 4n | 581 |

8.3 Chemical Stability

A stability study was carried out at 100° C. between variety I of compound 1 and the compound 1 described in patent EP 880514. The chemical stability of compound 1 is studied using HPLC with different scores.

The operating conditions of the HPLC method are the following:
    column: Interchim UP3HDO-15XS, 150×4.6 mm,

| eluent A: | water | 2500 |
|---|---|---|
|  | trifluoroacetic acid | 0.5 |
| eluent B: | acetonitrile |  | gradient:

| Time (min) | % A | % B |
|---|---|---|
| 0 | 80 | 20 |
| 22 | 5 | 95 |
| 24.2 | 80 | 20 | detection: 205 nm,
injection: 20 microliters,
temperature: 40° C.,
solution injected: 0.5 mg·mL$^{-1}$ (acetonitrile)

| | HPLC Purity | |
|---|---|---|
| Scores | Compound 1 Patent EP 880514 | Variety I of compound 1 |
| T0 | 99.6% | 99.6% |
| T1 day at 100° C. | 99.1% | 99.6% |
| T2 days at 100° C. | 98.8% | 99.7% |
| T3 days at 100° C. | 98.7% | 99.7% |
| T7 days at 100° C. | 98.0% | 99.7% |

9. Preparation of compound 1 of Form III

Form III of compound 1 as described in the present Application is obtained by a stage of synthesis of compound 1 (Example 5) followed by an additional stage which can be:
    a desolvation of the DMSO solvate of form 1 in water: Example 9a,
    a desolvation of the DMSO solvate of form 3 in water: Example 9b,
    an atomization in ethanol: Example 9c,
    an atomization in acetone: Example 9d
    a reimpasting in cumene under reflux: Example 9e,
    a heat treatment then a micronization, then a second heat treatment: Example 9f,
    a heat treatment of form II: Example 9g.

9.1 Desolvation of the DMSO Solvate of Form 1 in Water

Example 9aa

DMSO Solvate of Form 1 of Compound 1

1 mL of DMSO (Bp=189° C.) is poured into a pill box, then 1 g of compound 1 (Example 5) is added. The solution is stirred using a magnetic stirring bar and a magnetic stirrer. The solid passes into solution rapidly. 1 g of compound 1 is again added, still under magnetic stirring. The solid partly dissolves, then caking is observed. A sample of the caking is analyzed while still moist by X-ray powder diffraction. This analysis, presented hereafter, shows that this is the DMSO solvate of form 1 of compound 1 (Example 9aa).

Example 9a

The DMSO solvate of form 2 of compound 1 (Example 9aa) is immersed in cold water and left under stirring for five minutes at ambient temperature. The suspension is then filtered and dried.

Compound 1 of form III is thus obtained with a yield of 50% and presented hereafter.

9.2 Desolvation of the DMSO Solvate of Form 3 in Water

Example 9ba

DMSO Solvate of Form 3 of Compound 1

1 mL of DMSO (Bp=189° C.) is poured into a pill box, then 1 g of compound 1 (Example 1) is added. The solution is stirred using a magnetic stirring bar and a magnetic stirrer. The solid passes into solution rapidly. The solution is left under magnetic stirring for 24 hours. Caking is then observed.

A sample of the caking is analyzed while still moist by X-ray powder diffraction. This analysis, presented hereafter, shows that this is the DMSO solvate of form 3 of compound 1 (Example 9ba).

Example 9b

The DMSO solvate of form 3 of compound 1 (Example 3ba) is immersed in cold water and left under stirring for five minutes at ambient temperature. The suspension is then filtered and dried.

Compound 1 of form III is thus obtained with a yield of 50% and presented hereafter.

9.3 Atomization in Ethanol

Example 9c

The product obtained is produced with a Büchi 190 spray-dryer. 2 g of compound 1 (Example 5) are dissolved in 200 mL of ethanol (Bp=78° C.). The dry air inlet temperature is adjusted to 90° C. with a pressure of 3 bar. The outlet temperature is measured at 38° C. during the atomization. The outlet flow rate is adjusted to 700 NI/hour. 570 mg of dry powder are recovered and analyzed by X-ray powder diffraction. This analysis shows that this is form III of compound 1 which is structurally pure by comparison with the diagram calculated from the resolved single crystal structure.

Compound 1 of form III is thus obtained with a yield of 29% and presented hereafter.

9.4 Atomization in Acetone

Example 9d

The product obtained is produced with a Büchi 290 spray-dryer comprising an inert loop. 2 g of compound 1 (Example 1) are dissolved in 100 mL of acetone (Bp=56° C.). The dry air inlet temperature is adjusted to 70° C. The outlet temperature is measured at 50° C. during the atomization. The outlet flow rate is adjusted to 7600 NI/hour. 1 g of dry powder is recovered and analyzed by X-ray powder diffraction. This analysis shows that this is form III of compound 1 which is structurally pure by comparison with the diagram calculated from the resolved single crystal structure.

Compound 1 of form III is thus obtained with a yield of 50% and presented hereafter 9.5 Reimpasting in Cumene Under Reflux Example 9e 10 g of compound 1 (Example 5) are suspended in 100 of cumene (Bp=152° C.). The mixture is taken to reflux under stirring, then cooled down to ambient temperature. Analysis of the powder recovered and dried shows that it is form III of compound 1.

Compound 1 of form III is thus obtained with a yield of 99% and presented hereafter.

9.6 Heat treatment then micronization, then second heat treatment

Example 9f 150 g of compound 1 are heated in a ventilated oven at 160° C. for 15 minutes. The product thus heated is then micronized using a compressed air-jet micronizer. The micronization parameters are for the first pass: a Venturi pressure of 80 psi, a pressure of the micronizer of 120 psi and a feed rate of 1.2 kg·h$^{-1}$ and for the second pass: a Venturi pressure of 50 psi, a pressure of the micronizer of 50 psi and a feed rate of 1.2 kg·h$^{-1}$. The micronization yield is 69%. 15 g of the product thus obtained is heated at 160° C. for 15 minutes in a ventilated oven.

Compound 1 of form IIII is thus obtained with a yield of 69% and presented hereafter.

9.7 Heat Treatment of Form II 9.7.1 Obtaining Form II

Form II of compound 1 can be obtained by two synthesis routes:

by desolvation of 1,4-dioxane hemisolvate of compound 1 obtained beforehand by precipitation from 1,4-dioxane;

directly, by atomization in 1,4-dioxane.

Example 9h 1,4-dioxane Hemisolvate of Compound 1

A solution of compound 1 (Example 5) in 1,4-dioxane was prepared at ambient temperature and left under stirring for 24 hours. During the stirring, significant precipitation was observed. The solid was then filtered and analyzed by X-ray powder diffraction. The product obtained at the end of this stage is 1,4-dioxane hemisolvate of compound 1.

The 1,4-dioxane hemisolvate of compound 1 is thus obtained with a yield of 80% and presented hereafter.

Example 9i

Compound 1 of Form II

According to a first synthesis route, 1,4-dioxane hemisolvate of compound 1 (Example 9h) is heated from 20 to 80° C. at 5° C.·min$^{-1}$ under a flow of inert gas and produces, by desolvation, form II of compound 1 characterized by its X-ray diffraction pattern.

Compound 1 of form II is thus obtained with a yield of 99% and presented hereafter.

According to a second synthesis route, compound 1 of form II can be obtained as follows: 1 g of compound 1 (Example 5) was dissolved in 100 mL of 1,4-dioxane (Bp=101° C.). The inlet temperature: dust-free dry air was adjusted to 130° C. with a pressure of 3 bars. The outlet temperature was measured at 88° C. during the atomization. The outlet flow rate was adjusted to 700 NI/hour. The product obtained at the end of this stage is form II.

Compound 1 of form II is thus obtained with a yield of 50% and presented hereafter.

9.7.2 Obtaining Form III

Example 9g

The recovered dry powder of compound 1 of form II (Example 9i), was placed in an oven at 100° C. for a period of between 6 and 10 minutes, preferably for 7.5 minutes. The powder recovered after this treatment, analyzed by X-ray diffraction, is shown to be form III of compound 1 which is structurally pure by comparison with the calculated diagram obtained from the resolved single crystal structure.

Compound 1 of form III is thus obtained with a yield of 99% and presented hereafter 10. Characterization of the Solid Phases Obtained 10.1 Equipment Used
10.1.1 X-Ray Powder and Single Crystal Diffraction
Siemens D5005 diffractometer, scintillation detector
  Wavelength: 1.54056 Cu, voltage 40 KV, intensity 40 mA
  Measurement range: 3°-30°2 theta
  Interval: 0.04°2 theta
  Duration of the interval: 4s
  Fixed slots: 1.6 mm
  Kβ filter (Ni)
  Without internal reference
  EVA software (v 12.0) for data processing
Smart Apex Bruker diffractometer, two-dimensional detector
  SMART software for determination of the parameters and orientation of the crystal matrix
  SAINT software for data integration and processing
  WinGX software for determination of the space group and the structural resolution
10.1.2 DSC
  Netzsch DSC 204F1
  Aluminium crucible and pierced lid
  Atmosphere: Helium
  Initial temperature: 20° C.
  Final temperature: 200° C.
  Temperature gradient: 5° C.·min$^{-1}$
10.1.3 TG-DSC
  Netzsch STA449C
  Aluminium crucible and pierced lid
  Atmosphere: Helium
  Initial temperature: 25° C.
  Final temperature: 200° C.
  Temperature gradient: 5° C.·min$^{-1}$
10.1.4 IR
  KBr pellet
  Bruker IFS28 type spectrometer
  Spectral range: 400-4000 cm$^{-1}$
10.1.5 NMR of the Solid
  Bruker Avarice 500 MHz spectrometer
  MAS (Magic Angle Spinning) 4 mm probe
  Bruker XwinNMR software
  VACP (Variable Amplitude Cross-Polarization) with MAS (11 kHz) and proton decoupling (spinal 64, 65 kHz)
  External reference: Adamantane
10.2 Characterization of the Examples
10.2.1 Form I of Compound 1
  The X-ray powder diffraction diagram of form I of compound 1 exhibits the following characteristic peaks expressed as an angle (°2 theta) to approximately ±0.1°2 theta: 7.5; 10.9; 11.7; 13.1; 14.6; 15.0; 15.8; 17.0; 17.3; 17.5; 17.7; 17.9; 19.0; 19.9; 20.0; 21.4; 21.8; 22.5; 23.5; 23.9; 24.7; 24.9; 25.5; 25.9; 26.2; 26.4; 26.6; 27.2; 27.4; 27.6; 27.8; 28.2; 28.8; 29.0; 29.4; 29.8.
10.2.2 DMSO Solvate of Form 1 of Compound 1
  It was possible to isolate single crystals by slow evaporation of a saturated solution of DMSO at ambient temperature. These single crystals made it possible to resolve the complete structure of the DMSO solvate of form 1 of compound 1 by X-ray diffraction.
  Single-crystal X-ray diffraction: The crystalline structure of DMSO solvate of form 1 of compound 1 exhibits the following cell parameters:

| Cell structure | Orthorhombic |
| --- | --- |
| Space group | P n a 21 (no. 33) |
| Cell parameter a | 7.865(2) Å |
| Cell parameter b | 26.831(7) Å |
| Cell parameter c | 8.552(2) Å |
| Cell volume | 1804.7(8) Å$^3$ |
| Z, Z' | 4, 1 |
| Calculated density | 1.426 g · cm$^{-3}$ |

The atomic coordinates of the atoms in the cell ($\times 10^4$) and equivalent isotropic displacement parameters (Å$^2 \times 10^3$) (U(eq) equals a third of the value of the orthogonal tensor Uij) are the following:

| | x | Y | Z | U(eq) |
| --- | --- | --- | --- | --- |
| DMSO | | | | |
| S(1S) -sof 82% | 3004(1) | −4776(1) | 3282(1) | 53(1) |
| C(1S) -sof 82% | 1525(19) | −5222(5) | 3781(17) | 111(5) |
| C(2S) -sof 82% | 3218(15) | −4964(4) | 1289(10) | 90(3) |
| S(1B) -sof 18% | 1716(9) | −4777(3) | 2442(10) | 89(3) |
| C(1S) -sof 18% | 1470(70) | −5220(20) | 4050(50) | 64(14) |
| C(2S) -sof 18% | 3630(80) | −4960(20) | 1660(80) | 150(30) |
| O(1S) -sof 100% | 2086(3) | −4288(1) | 3208(3) | 71(1) |
| compound 1 | | | | |
| S(1) | 3171(1) | −3991(1) | −2614(1) | 50(1) |
| O(1) | 3373(2) | −2953(1) | 2905(2) | 45(1) |
| O(2) | 1598(3) | −3716(1) | −1780(3) | 56(1) |
| O(3) | 4389(3) | −2669(1) | 5103(2) | 61(1) |
| O(4) | 2553(4) | −4480(1) | −2855(3) | 76(1) |
| O(5) | 4621(3) | −3906(1) | −1670(3) | 74(1) |
| N(1) | 3426(4) | −3741(1) | −4247(3) | 55(1) |
| C(1) | 1942(3) | −3277(1) | −938(3) | 45(1) |
| C(2) | 2474(4) | −3321(1) | 585(3) | 42(1) |
| C(3) | 2806(3) | −2890(1) | 1397(3) | 39(1) |
| C(4) | 2600(4) | −2416(1) | 761(3) | 39(1) |
| C(5) | 1978(4) | −2393(1) | −768(4) | 50(1) |
| C(6) | 1654(4) | −2819(1) | −1618(4) | 53(1) |
| C(7) | 3867(4) | −2561(1) | 3808(3) | 43(1) |
| C(8) | 3741(3) | −2061(1) | 3159(3) | 41(1) |
| C(9) | 3098(3) | −1989(1) | 1720(3) | 41(1) |
| C(10) | 2897(4) | −1464(1) | 1080(4) | 54(1) |
| C(11) | 1668(4) | −1148(1) | 2029(5) | 62(1) |
| C(12) | 2392(5) | −921(1) | 3500(5) | 74(1) |
| C(13) | 2971(5) | −1291(1) | 4739(5) | 72(1) |
| C(14) | 4365(4) | −1646(1) | 4198(4) | 54(1) |

The coordinates of the hydrogen atoms ($\times 10^4$) and equivalent isotropic displacement parameters (Å$^2 \times 10^3$) (U(eq) equals a third of the value of the orthogonal tensor Uij) are the following:

| | x | Y | Z | U(eq) |
| --- | --- | --- | --- | --- |
| DMSO | | | | |
| H(1S1) -sof 82% | 1272 | −5197 | 4877 | 166 |
| H(1S2) -sof 82% | 1975 | −5547 | 3560 | 166 |
| H(1S3) -sof 82% | 505 | −5171 | 3186 | 166 |
| H(2S1) -sof 82% | 2119 | −4966 | 799 | 135 |
| H(2S2) -sof 82% | 3699 | −5292 | 1245 | 135 |
| H(2S3) -sof 82% | 3949 | −4734 | 751 | 135 |
| H(1S4) -sof 18% | 2436 | −5201 | 4734 | 96 |
| H(1S5) -sof 18% | 1380 | −5553 | 3640 | 96 |
| H(1S6) -sof 18% | 456 | −5143 | 4632 | 96 |
| H(2S4) -sof 18% | 4360 | −5076 | 2485 | 224 |

-continued

|  | X | Y | Z | U(eq) |
|---|---|---|---|---|
| H(2S5) -sof 18% | 4157 | −4679 | 1154 | 224 |
| H(2S6) -sof 18% | 3449 | −5220 | 918 | 224 |
| compound 1 | | | | |
| H(1N) | 3930(40) | −3453(9) | −4340(50) | 80(12) |
| H(2N) | 2890(40) | −3888(11) | −5020(30) | 64(11) |
| H(2) | 2605 | −3631 | 1051 | 51 |
| H(5) | 1778 | −2083 | −1222 | 60 |
| H(6) | 1247 | −2797 | −2636 | 63 |
| H(10A) | 2494 | −1482 | 10 | 65 |
| H(10B) | 4000 | −1302 | 1068 | 65 |
| H(11A) | 1251 | −881 | 1368 | 75 |
| H(11B) | 701 | −1353 | 2313 | 75 |
| H(12A) | 1537 | −706 | 3958 | 89 |
| H(12B) | 3353 | −714 | 3215 | 89 |
| H(13A) | 1998 | −1486 | 5073 | 87 |
| H(13B) | 3380 | −1107 | 5640 | 87 |
| H(14A) | 5219 | −1456 | 3636 | 64 |
| H(14B) | 4908 | −1790 | 5110 | 64 |

The interplanar spacings of the DMSO solvate form 1 are the following:

| H | K | L | 2Theta/deg | d/Å | I/rel, | |F(hkl)| |
|---|---|---|---|---|---|---|
| 0 | 2 | 0 | 6.58 | 13.42 | 26.46 | 51.61 |
| 0 | 1 | 1 | 10.85 | 8.15 | 19.64 | 51.99 |
| 1 | 1 | 0 | 11.72 | 7.55 | 5.73 | 30.36 |
| 1 | 2 | 0 | 13.04 | 6.78 | 50.44 | 100.35 |
| 0 | 3 | 1 | 14.32 | 6.18 | 35.57 | 92.69 |
| 1 | 1 | 1 | 15.65 | 5.66 | 11.88 | 41.47 |
| 1 | 2 | 1 | 16.67 | 5.32 | 6.67 | 33.15 |
| 1 | 4 | 0 | 17.36 | 5.10 | 4.75 | 41.24 |
| 1 | 3 | 1 | 18.24 | 4.86 | 100 | 140.76 |
| 0 | 5 | 1 | 19.51 | 4.55 | 3.97 | 42.54 |
| 1 | 5 | 0 | 20.02 | 4.43 | 4.96 | 48.79 |
| 0 | 0 | 2 | 20.76 | 4.28 | 19.58 | 142.36 |
| 0 | 2 | 2 | 21.80 | 4.07 | 15.41 | 93.94 |
| 1 | 5 | 1 | 22.58 | 3.94 | 58.83 | 134.63 |
| 2 | 0 | 0 | 22.59 | 3.93 | 59.76 | 271.6 |
| 2 | 1 | 0 | 22.84 | 3.89 | 14.54 | 95.81 |
| 1 | 6 | 0 | 22.86 | 3.89 | 5.27 | 57.75 |
| 1 | 1 | 2 | 23.90 | 3.72 | 4.68 | 40.32 |
| 1 | 2 | 2 | 24.59 | 3.62 | 15.88 | 76.48 |
| 2 | 0 | 1 | 24.90 | 3.57 | 12 | 95.3 |
| 2 | 1 | 1 | 25.12 | 3.54 | 17.07 | 81.13 |
| 1 | 6 | 1 | 25.14 | 3.54 | 4.28 | 40.67 |
| 0 | 7 | 1 | 25.45 | 3.50 | 10.41 | 90.79 |
| 2 | 2 | 1 | 25.78 | 3.45 | 31.33 | 112.94 |
| 0 | 8 | 0 | 26.56 | 3.35 | 6.34 | 104.82 |
| 2 | 3 | 1 | 26.85 | 3.32 | 21.73 | 98.17 |
| 1 | 4 | 2 | 27.19 | 3.28 | 8.87 | 63.57 |
| 2 | 4 | 1 | 28.28 | 3.15 | 16.18 | 89.51 |
| 0 | 6 | 2 | 28.87 | 3.09 | 2.69 | 52.79 |
| 1 | 5 | 2 | 28.99 | 3.08 | 2.13 | 33.37 |

The X-ray powder diffraction diagram of the DMSO solvate of form 1 of compound 1 exhibits the following characteristic peaks expressed as an angle (°2 theta) to approximately ±0.1°2 theta: 6.6; 10.9; 13.1; 14.3; 15.7; 16.7; 17.4; 18.3; 19.6; 20.8; 21.9; 22.6; 23.0; 24.7; 24.9; 25.2; 25.5; 25.8; 26.6; 26.9; 27.2; 28.3 (FIGS. 1 and 2).

2.2.3 DMSO Solvate of Form 3 of Compound 1

It was possible to isolate single crystals by slow evaporation of a saturated solution of DMSO at ambient temperature. These single crystals made it possible to resolve the complete structure of the DMSO solvate of form 3 of compound 1 by X-ray diffraction.

Single crystal X-ray diffraction: The crystalline structure of the DMSO solvate of form 3 of compound 1 was resolved and exhibits the following cell parameters:

| Cell structure | Monoclinic |
|---|---|
| Space group | P2$_1$/c |
| Cell parameter a | 13.842(1) Å |
| Cell parameter b | 7.243(1) Å |
| Cell parameter c | 18.778(1) Å |
| Cell parameter β | 104.950(2)° |
| Cell volume | 1818.8(3) Å$^3$ |
| Z, Z' | 4, 1 |
| Calculated density | 1.415 g·cm$^{-3}$ |

The coordinates of the hydrogen atoms (×10$^4$) and equivalent isotropic displacement parameters (Å$^2$×10$^3$) (U(eq) equals a third of the value of the orthogonal tensor Uij) are the following:

|  | X | Y | Z | U(eq) |
|---|---|---|---|---|
| DMSO | | | | |
| S(1S) | 5679(1) | −678(1) | 1794(1) | 60(1) |
| O(1S) | 5140(1) | −2300(3) | 1995(1) | 76(1) |
| C(2S) | 4755(3) | 819(4) | 1282(2) | 82(1) |
| C(1S) | 6168(2) | −1393(5) | 1053(2) | 88(1) |
| compound 1 | | | | |
| S(1) | 6816(1) | 4107(1) | −341(1) | 44(1) |
| N(1) | 6172(2) | 4790(3) | −1114(1) | 56(1) |
| O(1) | 10785(1) | 2986(2) | 1043(1) | 41(1) |
| O(2) | 7556(1) | 2659(2) | −587(1) | 44(1) |
| O(3) | 12316(1) | 3301(2) | 1722(1) | 62(1) |
| O(4) | 7413(1) | 5558(2) | 47(1) | 68(1) |
| O(5) | 6214(1) | 3068(3) | 19(1) | 63(1) |
| C(1) | 8322(1) | 1848(3) | −41(1) | 35(1) |
| C(2) | 9174(1) | 2840(2) | 267(1) | 37(1) |
| C(3) | 9947(1) | 1942(2) | 760(1) | 33(1) |
| C(4) | 9902(1) | 94(2) | 954(1) | 32(1) |
| C(5) | 9009(1) | −851(2) | 624(1) | 36(1) |
| C(6) | 8229(1) | 6(3) | 132(1) | 38(1) |
| C(7) | 11620(1) | 2256(3) | 1521(1) | 40(1) |
| C(8) | 11595(1) | 332(3) | 1739(1) | 36(1) |
| C(9) | 10769(1) | −716(2) | 1466(1) | 33(1) |
| C(10) | 10762(2) | −2712(3) | 1689(1) | 44(1) |
| C(11) | 10836(2) | −2998(3) | 2510(1) | 55(1) |
| C(12) | 11875(2) | −2835(4) | 3005(1) | 62(1) |
| C(13) | 12374(2) | −977(4) | 3018(1) | 58(1) |
| C(14) | 12530(2) | −382(3) | 2271(1) | 47(1) |

The coordinates of the hydrogen atoms (×10$^4$) and equivalent isotropic displacement parameters (Å$^2$×10$^3$) (U(eq) equals a third of the value of the orthogonal tensor Uij) are the following:

|  | X | y | Z | U(eq) |
|---|---|---|---|---|
| DMSO | | | | |
| H(2S1) | 4344 | 167 | 869 | 123 |
| H(2S2) | 5069 | 1847 | 1109 | 123 |
| H(2S3) | 4348 | 1260 | 1590 | 123 |
| H(1S1) | 6696 | −2271 | 1229 | 132 |
| H(1S2) | 6427 | −341 | 852 | 132 |
| H(1S3) | 5647 | −1955 | 677 | 132 |
| compound 1 | | | | |
| HN1 | 5730(20) | 3950(40) | −1360(15) | 67(8) |
| HN2 | 6490(20) | 5300(40) | −1342(16) | 64(9) |
| H(2) | 9230 | 4075 | 148 | 45 |
| H(5) | 8946 | −2085 | 741 | 43 |
| H(6) | 7646 | −641 | −81 | 45 |
| H(10A) | 11319 | −3338 | 1568 | 53 |
| H(10B) | 10151 | −3281 | 1403 | 53 |

-continued

| | x | y | z | U(eq) |
|---|---|---|---|---|
| H(11A) | 10412 | −2096 | 2663 | 66 |
| H(11B) | 10576 | −4213 | 2575 | 66 |
| H(12A) | 12292 | −3756 | 2855 | 74 |
| H(12B) | 11851 | −3134 | 3503 | 74 |
| H(13A) | 13019 | −1014 | 3376 | 70 |
| H(13B) | 11970 | −53 | 3179 | 70 |
| H(14A) | 13037 | 574 | 2353 | 56 |
| H(14B) | 12779 | −1429 | 2049 | 56 |

The interplanar spacings of the DMSO solvate form 3 are the following:

| h | k | l | 2θ/° | d/Å | I/rel. | |F(hkl)| |
|---|---|---|---|---|---|---|
| 1 | 0 | 0 | 6.60 | 13.37 | 17.46 | 34.28 |
| 0 | 0 | 2 | 9.74 | 9.07 | 17.01 | 50.02 |
| −1 | 0 | 2 | 10.27 | 8.61 | 60.85 | 99.75 |
| 1 | 0 | 2 | 13.12 | 6.74 | 8.70 | 48.35 |
| 0 | 1 | 1 | 13.15 | 6.73 | 2.09 | 16.81 |
| 1 | 1 | 0 | 13.89 | 6.37 | 32.93 | 70.48 |
| −1 | 1 | 1 | 14.15 | 6.25 | 9.87 | 39.31 |
| 1 | 1 | 1 | 15.29 | 5.79 | 18.39 | 58.07 |
| −1 | 1 | 2 | 15.98 | 5.54 | 70.84 | 119.22 |
| −2 | 1 | 1 | 17.77 | 4.99 | 100.00 | 157.96 |
| 1 | 1 | 2 | 17.96 | 4.93 | 2.26 | 23.99 |
| 2 | 1 | 0 | 18.04 | 4.91 | 3.73 | 31.00 |
| 2 | 0 | 2 | 18.39 | 4.82 | 22.48 | 109.68 |
| −2 | 1 | 2 | 18.83 | 4.71 | 25.27 | 84.24 |
| 0 | 1 | 3 | 19.10 | 4.64 | 44.16 | 113.07 |
| 2 | 1 | 1 | 19.58 | 4.53 | 3.05 | 30.49 |
| −3 | 0 | 2 | 19.78 | 4.49 | 13.70 | 92.30 |
| −2 | 0 | 4 | 20.62 | 4.30 | 95.08 | 253.85 |
| 1 | 1 | 3 | 21.45 | 4.14 | 51.77 | 138.03 |
| 2 | 1 | 2 | 22.13 | 4.01 | 4.74 | 43.13 |
| −1 | 1 | 4 | 22.61 | 3.93 | 24.41 | 100.12 |
| −3 | 1 | 1 | 22.84 | 3.89 | 64.70 | 164.68 |
| −3 | 1 | 2 | 23.31 | 3.81 | 2.35 | 32.07 |
| −2 | 1 | 4 | 24.03 | 3.70 | 60.09 | 167.40 |
| 3 | 0 | 2 | 24.40 | 3.65 | 14.20 | 116.93 |
| 0 | 2 | 1 | 25.06 | 3.55 | 4.08 | 45.58 |
| 2 | 1 | 3 | 25.41 | 3.50 | 4.75 | 49.91 |
| 1 | 1 | 4 | 25.45 | 3.50 | 16.21 | 92.36 |
| 1 | 2 | 0 | 25.46 | 3.50 | 9.39 | 70.33 |
| 1 | 2 | 1 | 26.27 | 3.39 | 10.61 | 77.23 |
| −1 | 1 | 5 | 26.72 | 3.33 | 4.25 | 49.77 |
| −3 | 1 | 4 | 27.09 | 3.29 | 7.04 | 65.01 |
| −2 | 2 | 1 | 27.82 | 3.20 | 11.13 | 84.10 |
| −1 | 0 | 6 | 28.51 | 3.13 | 2.66 | 59.69 |
| −2 | 2 | 2 | 28.52 | 3.13 | 3.31 | 47.10 |
| −1 | 2 | 3 | 28.60 | 3.12 | 5.99 | 63.51 |
| 2 | 2 | 1 | 29.04 | 3.07 | 6.40 | 66.75 |
| −2 | 0 | 6 | 29.08 | 3.07 | 12.26 | 130.81 |
| 2 | 1 | 4 | 29.20 | 3.06 | 21.47 | 122.94 |
| 4 | 1 | 0 | 29.40 | 3.04 | 5.99 | 65.40 |
| 0 | 0 | 6 | 29.52 | 3.02 | 8.88 | 113.14 |
| −4 | 1 | 3 | 29.65 | 3.01 | 2.46 | 42.34 |

Figure 3:
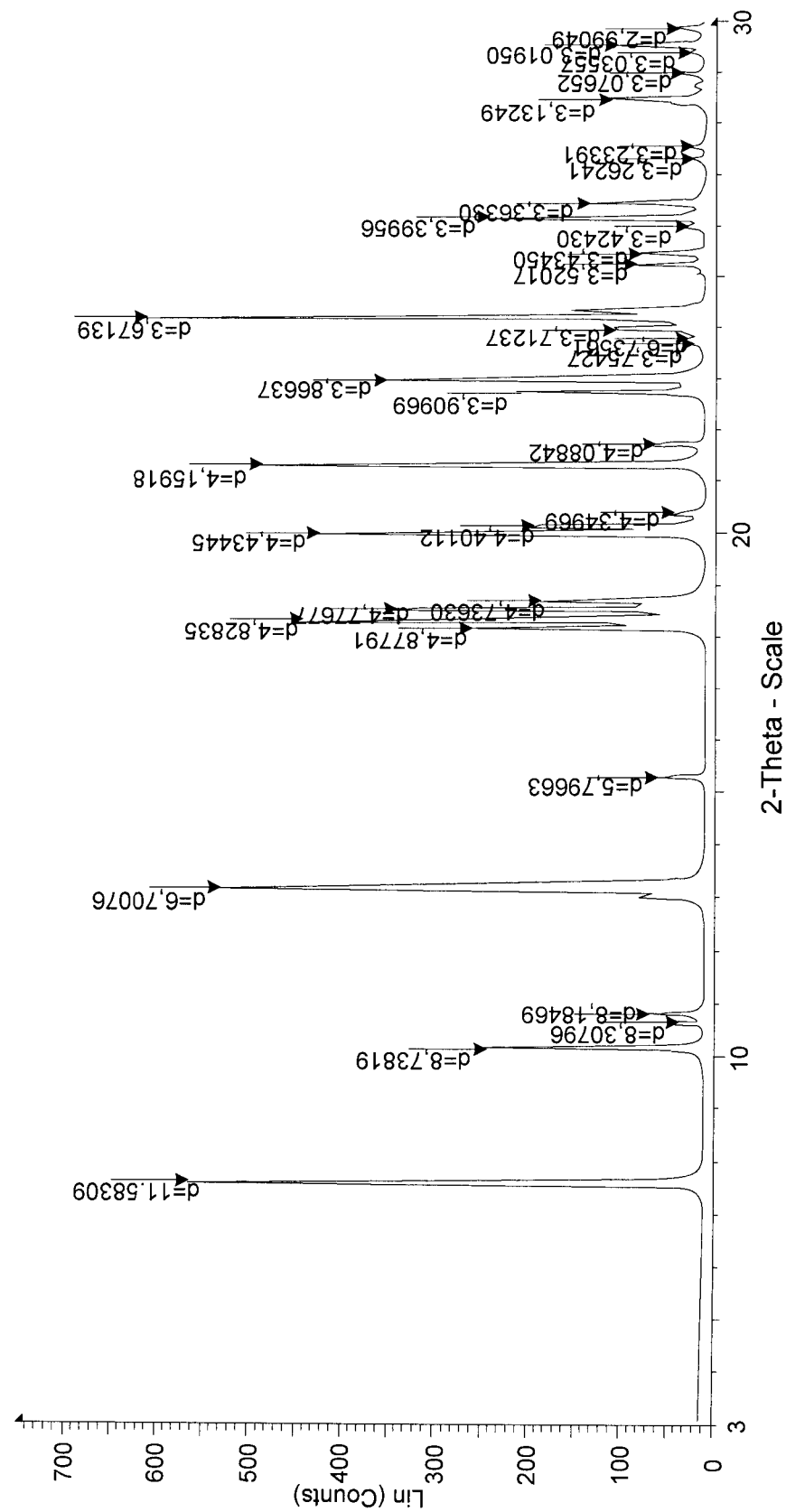
FIG. 3: calculated X-ray diffraction diagram of the DMSO solvate of form 2 of compound 1
Figure 4:
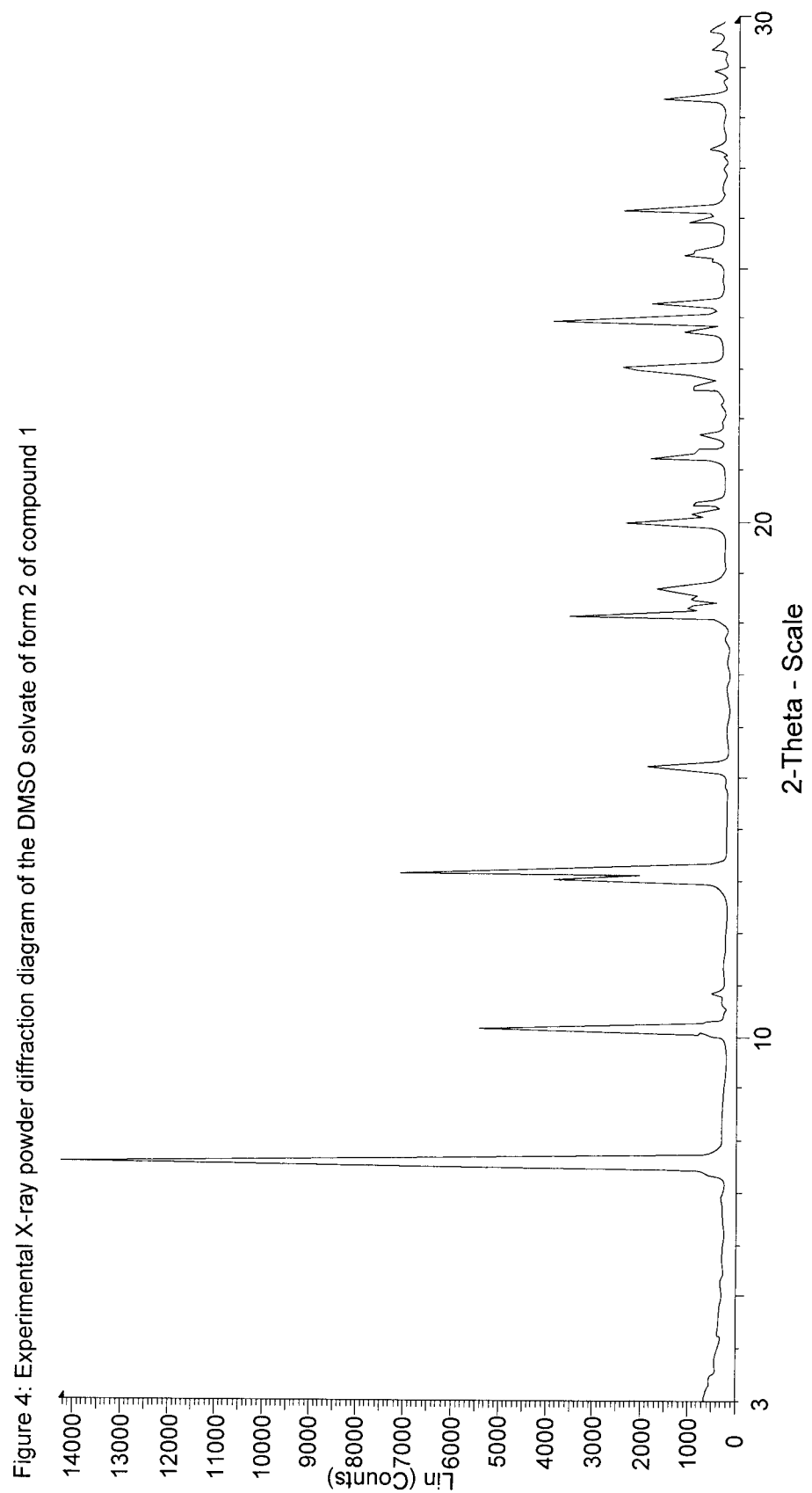
FIG. 4: experimental X-ray powder diffraction diagram of the DMSO solvate of form 2 of compound 1

The X-ray powder diffraction diagram of the DMSO solvate of form 3 of compound 1 exhibits the following characteristic peaks expressed as an angle (°2 theta) to approximately ±0.1°2 theta: (FIGS. 3 and 4). 9.7; 13.9; 16.0; 17.8; 19.1; 22.1.

2.2.4 Single Crystal X-Ray Diffraction of the Form III

By slow evaporation at ambient temperature of a saturated solution of compound 1 in an acetone/n-heptane mixture, 50% v/v, it was possible to isolate single crystals which have made it possible to resolve the complete structure of form III of compound 1 by X-ray diffraction.

Single crystal X-ray diffraction: The crystalline structure of compound 1 form III was resolved and exhibits the following cell parameters

| Cell structure | Monoclinic |
|---|---|
| Space group | Cc (no. 9) |
| Cell parameter a | 11.327(1) Å |
| Cell parameter b | 20.489(2) Å |
| Cell parameter c | 7.870(1) Å |
| Cell parameter β | 131.55(1)° |
| Cell volume | 1366.9(2) Å$^3$ |
| Number of molecules per cell: Z | 4 |
| Calculated density | 1.53 g·cm$^{-3}$ |

The reduced coordinates ($\times 10^4$) and the equivalent isotropic motion parameters ($\text{Å}^2 \times 10^3$) of compound 1 form III are the following:

| | x | y | z | U(eq) |
|---|---|---|---|---|
| S(1) | 14534(1) | −1891(1) | 11571(1) | 41(1) |
| O(1) | 9079(2) | −569(1) | 5756(3) | 39(1) |
| O(2) | 13824(2) | −1450(1) | 12407(3) | 48(1) |
| O(3) | 6862(3) | −250(1) | 2510(3) | 57(1) |
| O(4) | 13672(3) | −1754(1) | 9246(3) | 62(1) |
| O(5) | 14551(3) | −2522(1) | 12277(5) | 73(1) |
| N(1) | 16289(3) | −1661(2) | 12982(5) | 55(1) |
| C(1) | 12910(3) | −904(1) | 11114(4) | 36(1) |
| C(2) | 11424(3) | −995(1) | 9041(4) | 37(1) |
| C(3) | 10541(3) | −449(1) | 7814(4) | 31(1) |
| C(4) | 11093(3) | 187(1) | 8587(4) | 32(1) |
| C(5) | 12593(3) | 249(1) | 10745(4) | 40(1) |
| C(6) | 13504(3) | −284(1) | 11996(4) | 42(1) |
| C(7) | 8111(3) | −78(1) | 4284(4) | 39(1) |
| C(8) | 8699(3) | 589(1) | 4976(4) | 37(1) |
| C(9) | 10098(3) | 718(1) | 7049(4) | 34(1) |
| C(10) | 10637(3) | 1421(1) | 7790(5) | 43(1) |
| C(11) | 9541(4) | 1809(1) | 7904(5) | 46(1) |
| C(12) | 8072(4) | 2076(1) | 5641(5) | 56(1) |
| C(13) | 6921(4) | 1568(2) | 3890(5) | 55(1) |
| C(14) | 7630(4) | 1111(1) | 3226(5) | 48(1) |

The coordinates of the hydrogen atoms ($\times 10^4$) and equivalent isotropic displacement parameters ($\text{Å}^2 \times 10^3$) (U(eq) equals a third of the value of the orthogonal tensor Uij) are the following:

| | x | y | z | U(eq) |
|---|---|---|---|---|
| HN1 | 16970(60) | −1842(18) | 14350(80) | 78(13) |
| HN2 | 16430(50) | −1342(19) | 12870(60) | 56(12) |
| H(2) | 11025 | −1412 | 8483 | 44 |
| H(5) | 12982 | 664 | 11349 | 48 |
| H(6) | 14506 | −231 | 13414 | 50 |
| H(10A) | 10682 | 1631 | 6729 | 52 |
| H(10B) | 11693 | 1424 | 9273 | 52 |
| H(11A) | 9218 | 1531 | 8530 | 55 |
| H(11B) | 10129 | 2172 | 8944 | 55 |
| H(12A) | 7523 | 2355 | 5918 | 67 |
| H(12B) | 8398 | 2347 | 5004 | 67 |
| H(13A) | 6016 | 1789 | 2538 | 66 |
| H(13B) | 6550 | 1309 | 4487 | 66 |
| H(14A) | 6778 | 901 | 1798 | 57 |
| H(14B) | 8227 | 1369 | 2988 | 57 |

The interplanar spacings are the following:

| H | K | L | 2Theta/deg | d/Å | I/rel, | |F(hkl)| |
|---|---|---|---|---|---|---|
| 0 | 2 | 0 | 8.63 | 10.24 | 16.76 | 35.88 |
| 1 | 1 | 0 | 11.29 | 7.83 | 37.69 | 49.89 |
| −1 | 1 | 1 | 12.05 | 7.34 | 59.53 | 66.98 |

-continued

| H  | K | L | 2Theta/deg | d/Å  | I/rel, | |F(hkl)| |
|----|---|---|-----------|------|--------|---------|
| 1  | 3 | 0 | 16.66     | 5.32 | 57.37  | 91.43   |
| -1 | 3 | 1 | 17.18     | 5.16 | 11.98  | 43.15   |
| 0  | 2 | 1 | 17.35     | 5.11 | 92.5   | 121.09  |
| -2 | 2 | 1 | 17.92     | 4.95 | 73.94  | 111.89  |
| 2  | 0 | 0 | 20.94     | 4.24 | 13.54  | 79.54   |
| -2 | 0 | 2 | 22.60     | 3.93 | 89.64  | 221.49  |
| 2  | 2 | 0 | 22.69     | 3.92 | 23.89  | 81.17   |
| 0  | 4 | 1 | 22.99     | 3.87 | 27.76  | 88.74   |
| -2 | 4 | 1 | 23.43     | 3.79 | 43.01  | 112.65  |
| 1  | 1 | 1 | 23.81     | 3.73 | 20.41  | 78.91   |
| 1  | 5 | 0 | 24.10     | 3.69 | 13.86  | 65.87   |
| -2 | 2 | 2 | 24.23     | 3.67 | 3.27   | 32.19   |
| -3 | 1 | 1 | 24.64     | 3.61 | 12.1   | 63      |
| -1 | 1 | 2 | 24.92     | 3.57 | 10.88  | 60.46   |
| -3 | 1 | 2 | 25.73     | 3.46 | 100    | 189.5   |
| 0  | 6 | 0 | 26.07     | 3.41 | 11.99  | 94.11   |
| 2  | 4 | 0 | 27.29     | 3.27 | 2.04   | 28.78   |
| -3 | 3 | 1 | 27.59     | 3.23 | 12.23  | 71.34   |
| -3 | 3 | 2 | 28.57     | 3.12 | 46.83  | 144.9   |

10.2.5 Examples 9a-9g: Compound 1 of Form III

Analyses by X-ray powder diffraction, by single crystal X-ray diffraction, by DSC, by IR and by NMR of the solid show that Example 9a is identical to Example 9b, to Example 9c, to Example 9d, to Example 9e, to Example 9f and to Example 9g.

10.2.5.1 X-Ray Powder Diffraction

The X-ray powder diffraction diagram of form III of compound 1 exhibits the following characteristic peaks expressed as an angle (°2 theta) to approximately ±0.1°2 theta: 8.6; 11.3; 12.0; 16.7; 17.4; 17.9; 20.9; 22.6; 23.0; 23.4; 23.8; 25.7; 28.6 (FIGS. 5 and 6).

10.2.5.2 DSC

In DSC, the thermogram of form III of compound 1 comprises the melting peak of form III (onset 180°±2° C.) (FIG. 7).

10.2.5.3 IR

The IR spectrum of form 111 of compound 1 exhibits the characteristic peaks expressed in cm$^{-1}$ to approximately ±5 cm$^{-1}$: 3406; 3217; 3082; 2924; 1678; 138 5; 1269; 1134; 1011; 934; 845; 601; 563; 536 (FIG. 8).

10.2.5.4 NMR of the Solid

The spectrum of form III obtained by NMR of the solid exhibits the following characteristic peaks expressed in ppm to approximately ±0.2 ppm: 162.9; 156.4; 151.3; 126.1; 124.7; 118.8; 117.1; 112.9; 35; 20 (FIG. 9).

10.2.6 Example 9h: 1,4-dioxane Hemisolvate of Compound 1

10.2.6.1 Single Crystal X-Ray Diffraction

By slow evaporation at ambient temperature of a saturated solution of compound 1 in 1,4-dioxane, it was possible to isolate single crystals which made it possible to resolve the complete structure of 1,4-dioxane hemisolvate of compound 1 by X-ray diffraction.

The crystalline structure of 1,4-dioxane hemisolvate of compound 1 exhibits the following cell parameters:

| Cell structure | Triclinic |
|---|---|
| Space group | P-1 (no. 2) |
| Cell parameter a | 9.016(4) Å |
| Cell parameter b | 9.765(5) Å |
| Cell parameter c | 10.068(5) Å |
| Cell parameter α | 67.731(9)° |
| Cell parameter β | 78.939(8)° |
| Cell parameter γ | 86.504(9)° |
| Cell volume | 805.0(7) Å$^3$ |
| Z, Z' | 2.1 |
| Calculated density | 1.46 g·cm$^{-3}$ |

The reduced coordinates (×10$^4$) and the equivalent isotropic motion parameters (Å$^2$×10$^3$) of 1,4-dioxane hemisolvate of compound 1 are the following:

| | x | Y | z | U(eq) |
|---|---|---|---|---|
| | | compound 1 | | |
| S | 475(1) | 7183(1) | 1077(1) | 41(1) |
| N(1) | 763(4) | 5616(4) | 989(3) | 47(1) |
| O(1) | -1281(2) | 11547(2) | 2861(2) | 43(1) |
| O(2) | 133(2) | 6737(2) | 2827(2) | 47(1) |
| O(3) | -1860(3) | 13790(3) | 2773(3) | 54(1) |
| O(4) | -870(2) | 7799(3) | 566(2) | 57(1) |
| O(5) | 1837(3) | 8014(3) | 527(3) | 63(1) |
| C(1) | -523(3) | 7714(4) | 3486(3) | 37(1) |
| C(2) | -582(3) | 9222(4) | 2787(3) | 38(1) |
| C(3) | -1256(3) | 10032(3) | 3607(3) | 34(1) |
| C(4) | -1856(3) | 9411(3) | 5087(3) | 34(1) |
| C(5) | -1743(3) | 7874(4) | 5739(3) | 39(1) |
| C(6) | -1092(3) | 7036(4) | 4965(3) | 41(1) |
| C(7) | -1928(3) | 12484(4) | 3529(4) | 41(1) |
| C(8) | -2612(3) | 11855(4) | 5064(3) | 38(1) |
| C(9) | -2564(3) | 10376(4) | 5824(3) | 35(1) |
| C(10) | -3269(4) | 9731(4) | 7424(3) | 45(1) |
| C(11) | -4991(4) | 9893(4) | 7686(4) | 56(1) |
| C(12) | -5519(4) | 11392(4) | 7687(4) | 59(1) |
| C(13) | -5070(4) | 12689(4) | 6262(4) | 57(1) |
| C(14) | -3361(4) | 12922(4) | 5733(4) | 50(1) |
| | | 1,4-dioxane | | |
| O(1B) | 3697(2) | 4239(3) | 922(2) | 52(1) |
| C(2B) | -4194(4) | 15845(4) | 477(4) | 51(1) |
| C(3B) | -5035(4) | 14451(4) | 1488(4) | 59(1) |

The hydrogen coordinates (×10$^4$) and the equivalent isotropic displacement parameters (Å$^2$×10$^3$) of 1,4-dioxane hemisolvate of compound 1 are the following:

| | x | Y | z | U(eq) |
|---|---|---|---|---|
| | | compound 1 | | |
| H(1N) | 1690(40) | 5240(40) | 1000(30) | 47(11) |
| H(2N) | 60(40) | 5060(40) | 1390(40) | 54(12) |
| H(2) | -183 | 9683 | 1798 | 46 |
| H(5) | -2123 | 7407 | 6730 | 46 |
| H(6) | -1030 | 6015 | 5430 | 49 |
| H(10A) | -2839 | 10225 | 7939 | 55 |
| H(10B) | -3023 | 8691 | 7822 | 55 |
| H(11A) | -5381 | 9711 | 6934 | 67 |
| H(11B) | -5416 | 9141 | 8618 | 67 |
| H(12A) | -5123 | 11569 | 8439 | 71 |
| H(12B) | -6612 | 11361 | 7953 | 71 |
| H(13A) | -5500 | 13581 | 6377 | 69 |
| H(13B) | -5506 | 12541 | 5516 | 69 |
| H(14A) | -3170 | 13922 | 5018 | 60 |
| H(14B) | -2896 | 12835 | 6554 | 60 |
| | | 1,4-dioxane | | |
| H(2B1) | -4849 | 16689 | 390 | 61 |
| H(2B2) | -3331 | 15974 | 865 | 61 |
| H(3B1) | -4365 | 13614 | 1606 | 70 |
| H(3B2) | -5381 | 14507 | 2440 | 70 |

The interplanar spacings of 1,4-dioxane hemisolvate are the following:

| H | K | L | 2Theta/deg | d/Å | I/rel, | |F(hkl)| |
|---|---|---|---|---|---|---|
| 0 | 1 | 0 | 9.78 | 9.04 | 8.88 | 16.31 |
| 1 | 0 | 0 | 9.99 | 8.85 | 96.1 | 54.8 |
| 0 | 1 | 1 | 10.87 | 8.14 | 11.91 | 21 |
| 1 | 1 | 1 | 13.62 | 6.50 | 5.21 | 17.46 |
| 1 | −1 | 0 | 13.91 | 6.36 | 5 | 17.48 |
| 1 | 1 | 0 | 14.09 | 6.28 | 20.11 | 35.51 |
| −1 | 1 | 1 | 15.86 | 5.58 | 5.85 | 21.61 |
| 0 | −1 | 1 | 16.14 | 5.49 | 97.94 | 90.03 |
| 1 | −1 | 1 | 17.98 | 4.93 | 2.67 | 16.6 |
| 0 | 2 | 1 | 18.34 | 4.83 | 2.6 | 16.71 |
| 1 | 1 | 2 | 18.99 | 4.67 | 57.23 | 81.32 |
| 0 | 2 | 0 | 19.63 | 4.52 | 12.83 | 39.85 |
| −1 | −1 | 1 | 20.00 | 4.44 | 3.87 | 22.31 |
| 2 | 0 | 0 | 20.06 | 4.42 | 13.37 | 41.58 |
| 1 | 2 | 1 | 20.18 | 4.40 | 28.43 | 61.01 |
| 2 | 0 | 1 | 20.62 | 4.30 | 57.35 | 88.64 |
| 2 | 1 | 1 | 21.35 | 4.16 | 100 | 121.33 |
| −1 | 2 | 1 | 21.65 | 4.10 | 22.75 | 58.7 |
| 0 | 2 | 2 | 21.83 | 4.07 | 4.02 | 24.89 |
| 1 | −2 | 0 | 21.96 | 4.05 | 19.56 | 55.24 |
| 1 | 2 | 0 | 22.19 | 4.00 | 23.96 | 61.82 |
| 2 | −1 | 0 | 22.24 | 3.99 | 15.45 | 49.77 |
| −1 | 1 | 2 | 22.34 | 3.98 | 28.24 | 67.59 |
| −1 | 0 | 2 | 23.43 | 3.79 | 4.95 | 29.72 |
| −2 | 0 | 1 | 23.86 | 3.73 | 2.29 | 20.61 |
| 2 | −1 | 1 | 24.30 | 3.66 | 29.1 | 74.91 |
| 2 | 1 | 2 | 24.44 | 3.64 | 28.94 | 75.16 |
| 0 | −1 | 2 | 24.85 | 3.58 | 13.62 | 52.47 |
| 2 | 0 | 2 | 25.29 | 3.52 | 29.21 | 78.26 |
| −1 | 2 | 2 | 25.42 | 3.50 | 8.32 | 42 |
| 1 | −2 | 1 | 26.21 | 3.40 | 3.8 | 29.32 |
| 1 | 1 | 3 | 27.01 | 3.30 | 13.64 | 57.32 |
| 0 | 1 | 3 | 27.07 | 3.29 | 13.27 | 56.7 |
| −2 | −1 | 1 | 27.32 | 3.26 | 3.16 | 27.92 |
| 0 | 3 | 1 | 27.46 | 3.25 | 14.04 | 59.19 |
| −1 | −1 | 2 | 28.22 | 3.16 | 7.33 | 44.04 |
| 2 | 2 | 0 | 28.40 | 3.14 | 3.67 | 31.36 |
| 0 | 2 | 3 | 28.47 | 3.13 | 3.36 | 30.09 |
| 0 | 3 | 2 | 28.70 | 3.11 | 6.78 | 43.12 |
| 1 | 0 | 3 | 29.12 | 3.06 | 2.24 | 25.18 |
| 1 | 3 | 2 | 29.37 | 3.04 | 2.07 | 24.42 |

10.2.6.2 X-Ray Powder Diffraction

Figure 10:
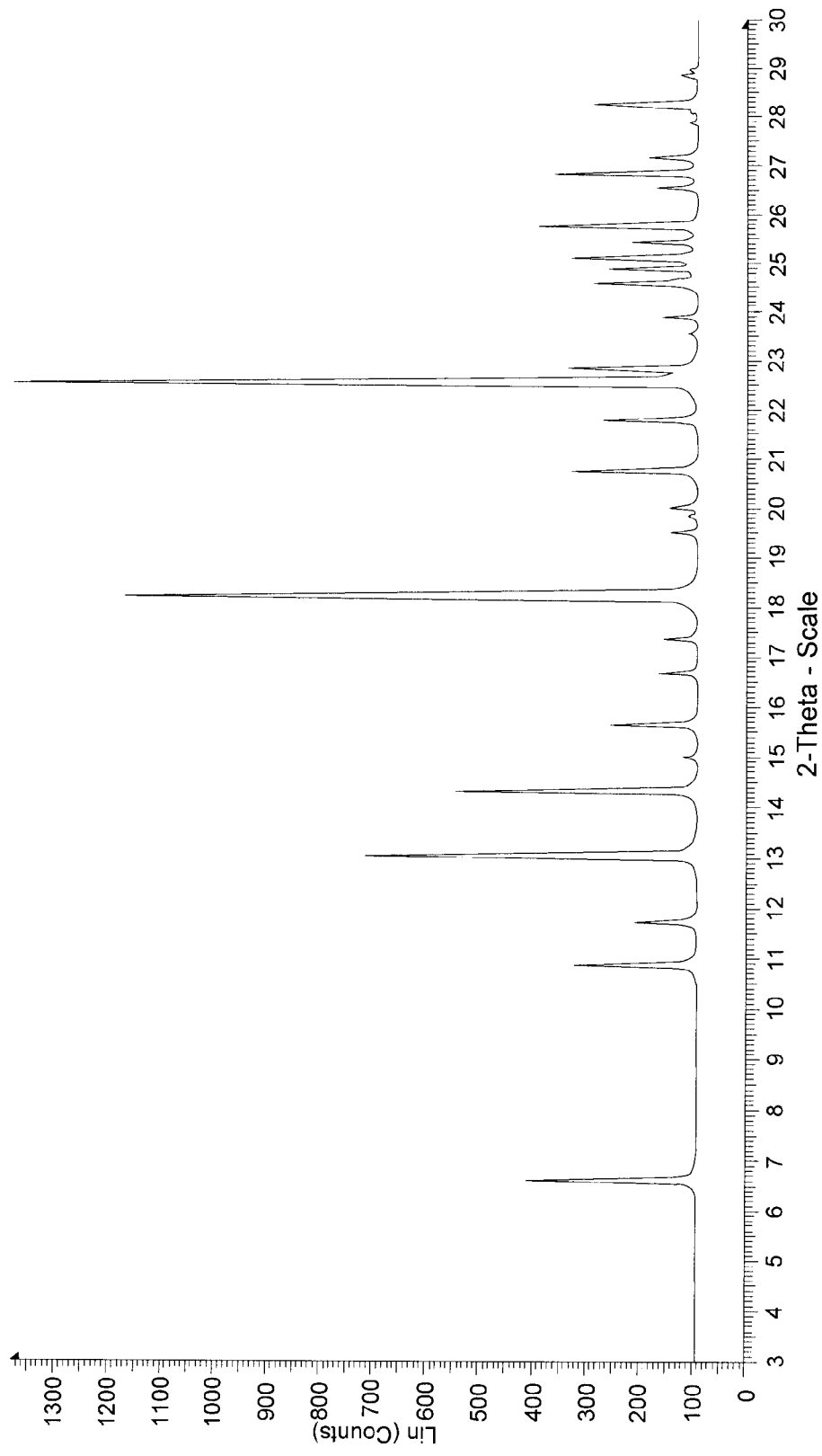
FIG. 10: calculated X-ray diffraction diagram of the DMSO solvate of form 1 of compound 1
Figure 11:
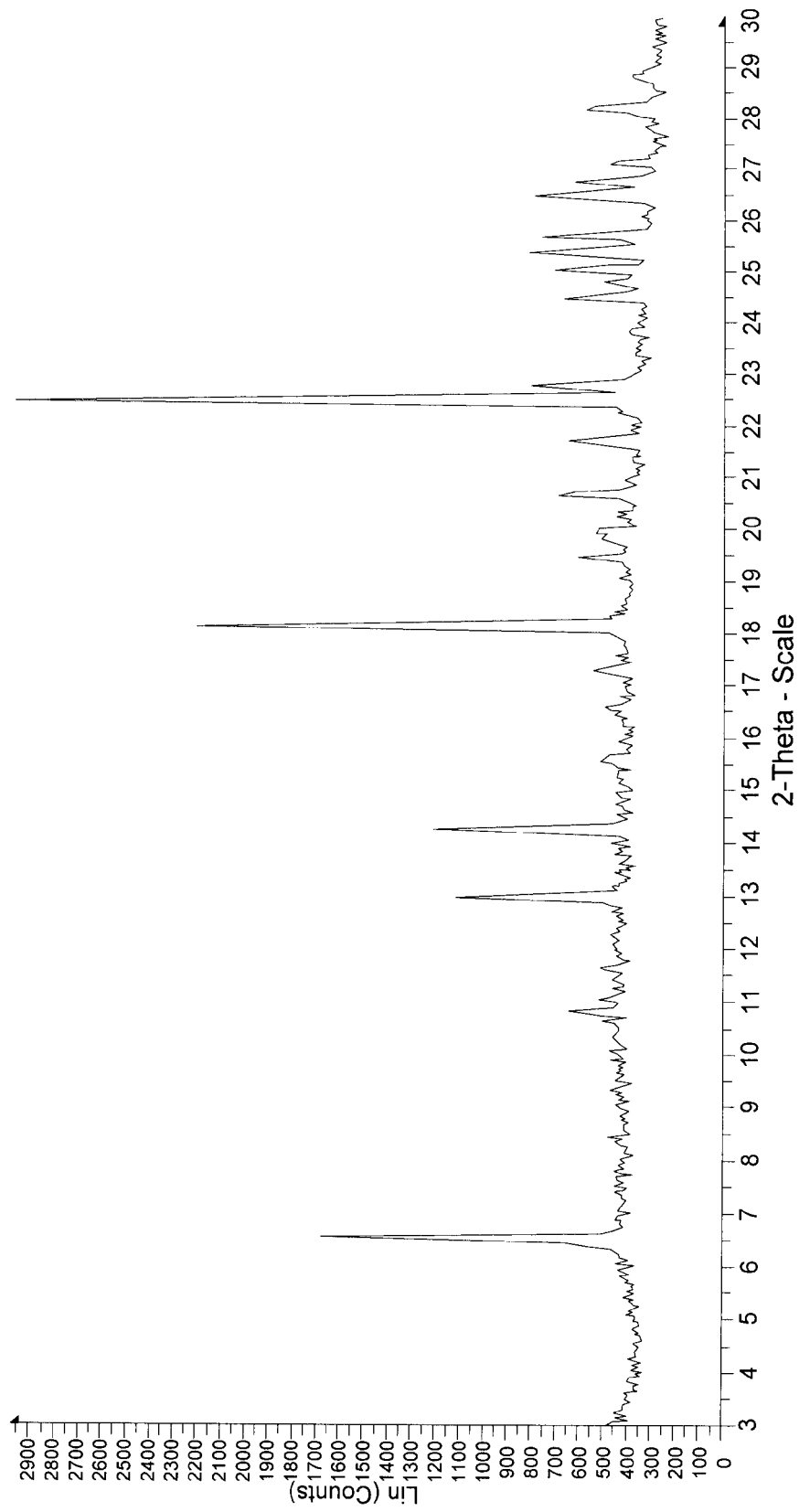
FIG. 11: experimental X-ray powder diffraction diagram of the DMSO solvate of form 1 of compound 1

The X-ray powder diffraction diagram of 1,4-dioxane hemisolvate of compound 1 exhibits the following characteristic peaks expressed as an angle (°2 theta) to approximately ±0.1°2 theta: 9.8; 10.0; 10.8; 13.6; 13.9; 14.1; 15.9; 16.1; 18.0; 18.3; 19.0; 19.6; 20.0; 20.1; 202; 20.6; 21.4; 21.7; 21.8; 22.0; 22.2; 22.3; 23.4; 23.9; 24.3; 24.4; 24.9; 25.3; 25.4; 26.2; 27.0; 27.1; 27.3; 27.5; 28.2; 28.4; 28.5; 28.7; 29.1; 29.4 (FIGS. 10 and 11).

10.2.6.2 TG-DSC

Figure 12:
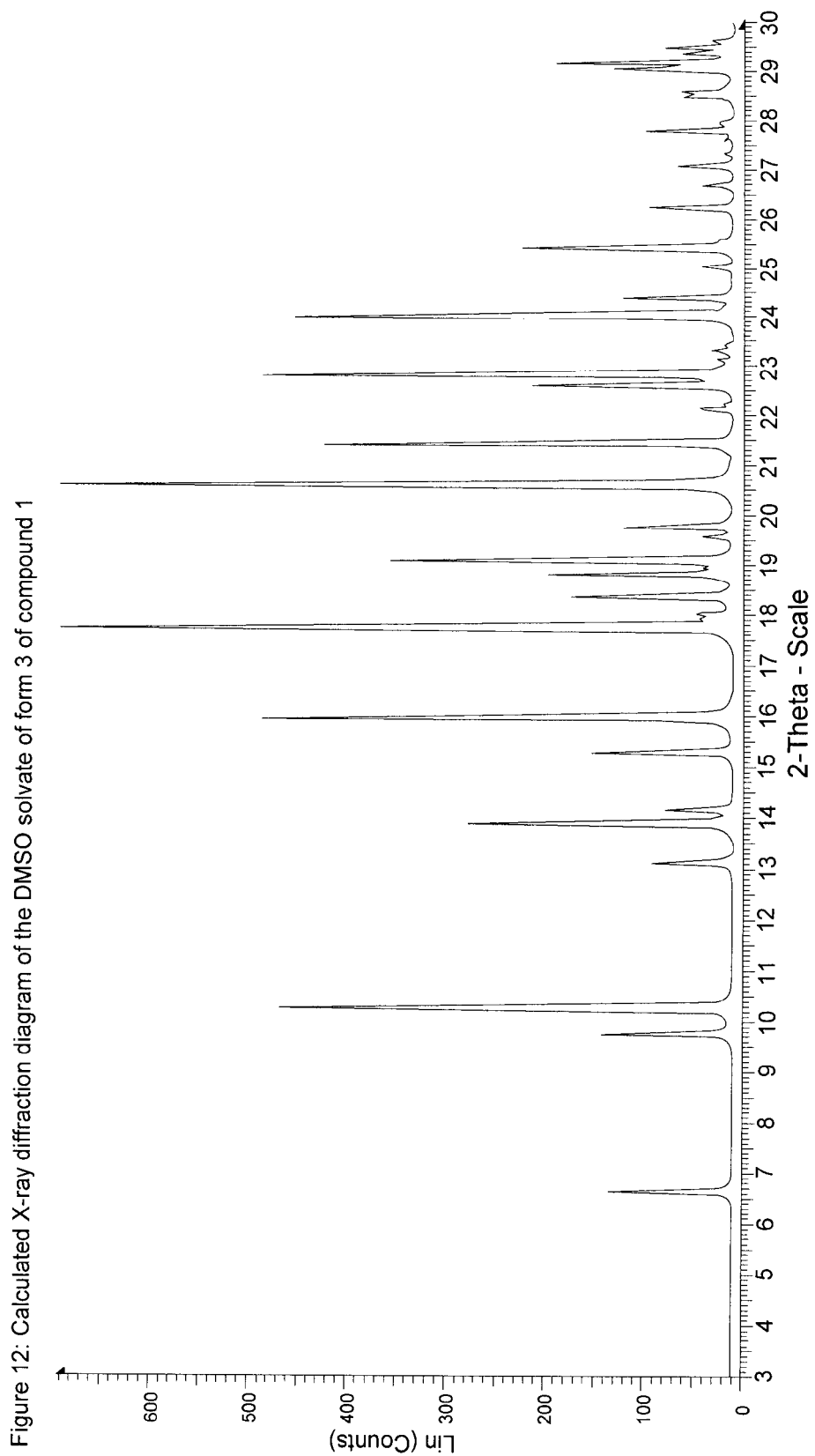
FIG. 12: calculated X-ray diffraction diagram of the DMSO solvate of form 3 of compound 1

Using TG-DSC, the thermogram of 1,4-dioxane hemisolvate of compound 1 shows that the solvate releases 1,4-dioxane starting from 75° C. in order to produce form II of compound 1 (FIG. 12).

10.2.7 Example 9i: Compound 1 of Form II 10.2.7.1 X-Ray Powder Diffraction

Figure 13:
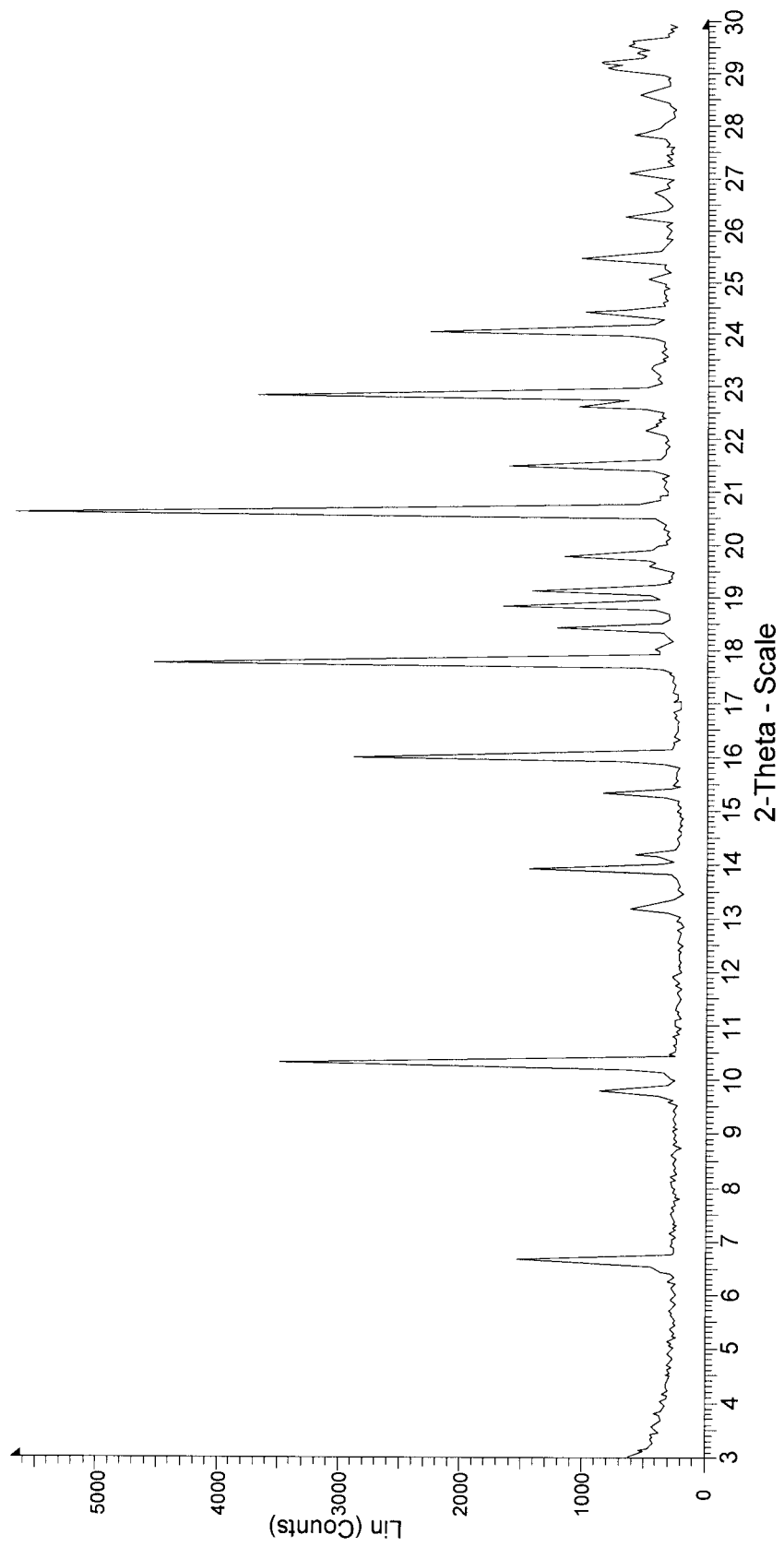
FIG. 13: experimental X-ray powder diffraction diagram of the DMSO solvate of form 3 of compound 1

The X-ray powder diffraction diagram of form II of compound 1 exhibits the following characteristic peaks expressed as an angle (°2 theta) to approximately ±0.1°2 theta: 9.4; 10.7; 12.2; 12.8; 14.3; 15.1; 15.9; 16.9; 18.2; 18.9; 19.4; 19.7; 20.4; 21.1; 21.4; 21.8; 22.0; 22.7; 23.0; 23.2; 23.7; 23.9; 24.4; 24.8; 25.5; 26.8; 27.1; 27.4; 28.1; 28.3; 29.5 (FIG. 13).

10.2.7.2 DSC

Figure 14:
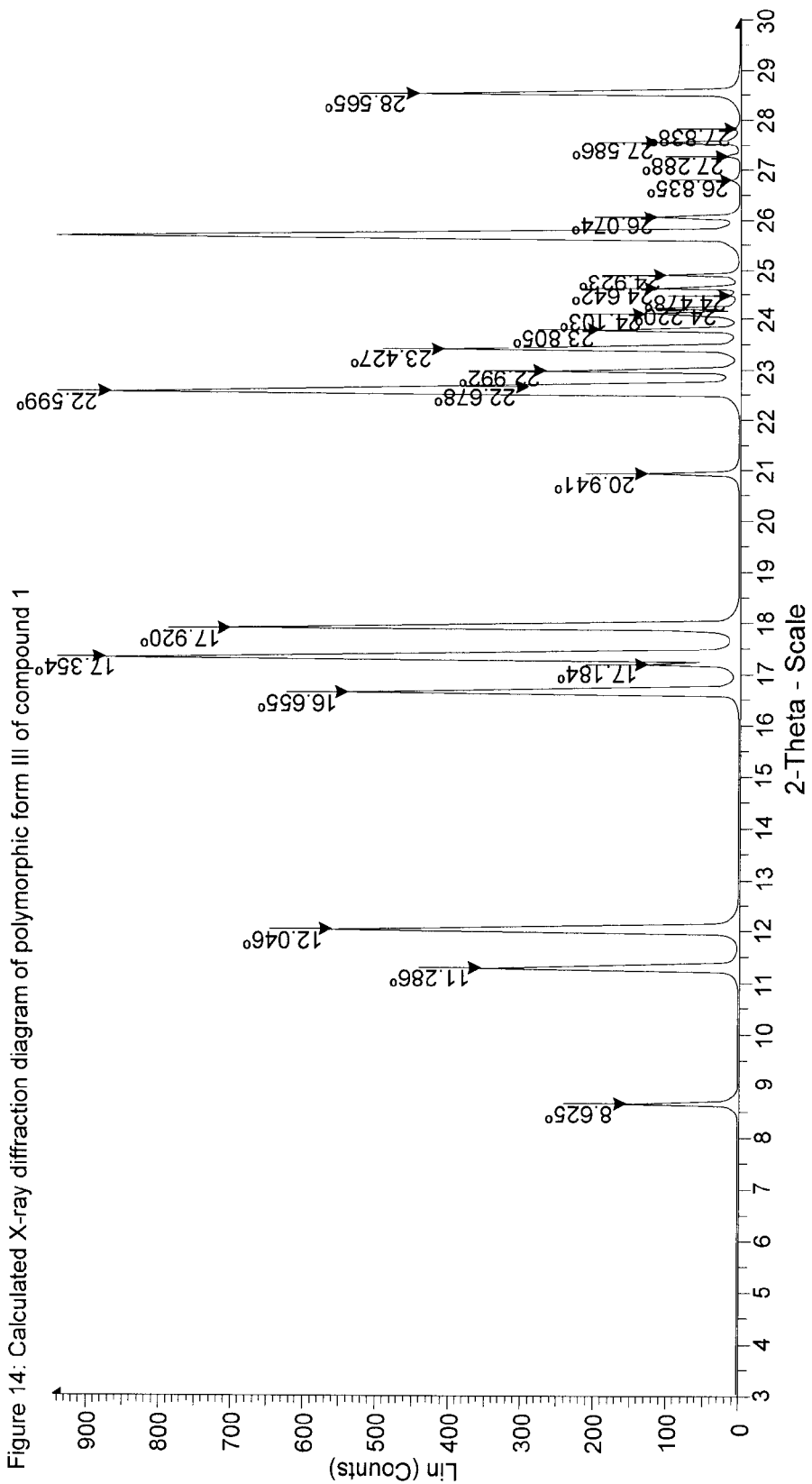
FIG. 14: calculated X-ray diffraction diaciram of polymorphic form III of compound 1

Using DSC, the thermogram of form II of compound 1 comprises an endothermic phenomenon which corresponds to the metastable melting of form II at 165° C.±5° C., then recrystallization to other forms, followed by other melting phenomena (FIG. 14).

10.2.7.3 IR

Figure 15:
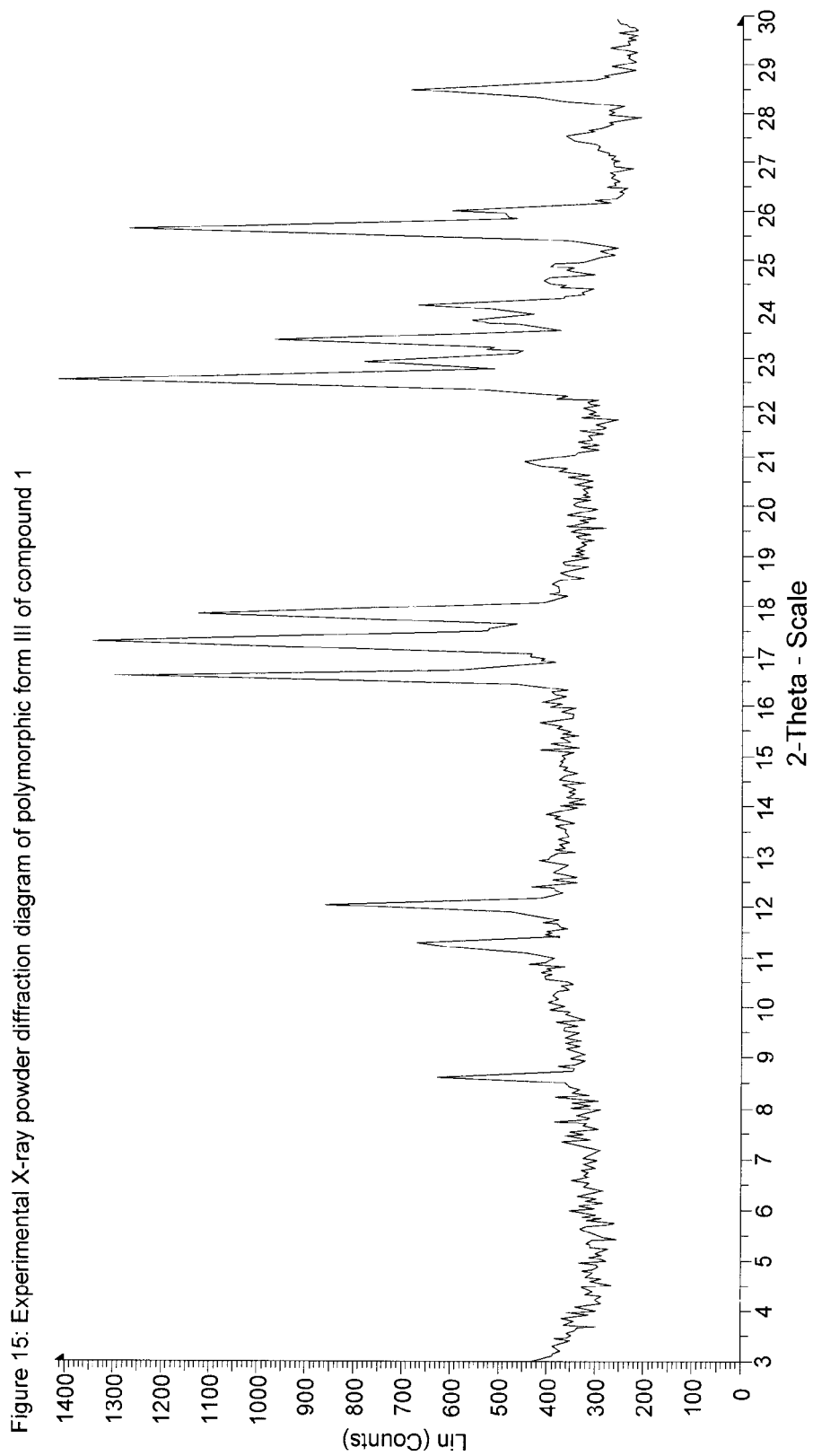
FIG. 15: experimental X-ray powder diffraction diagram of polymorphic form III of compound 1

The IR spectrum of form II of compound 1 exhibits the characteristic peaks expressed in $cm^{-1}$ to approximately ±5 $cm^{-1}$: 3356; 3321; 3186; 3078; 2932; 2851; 1693; 1609; 1504; 1462; 1377; 1265; 1192; 1123; 937; 872; 837; 787; 594 (FIG. 15).

10.2.7.4 NMR of the Solid

Figure 16:
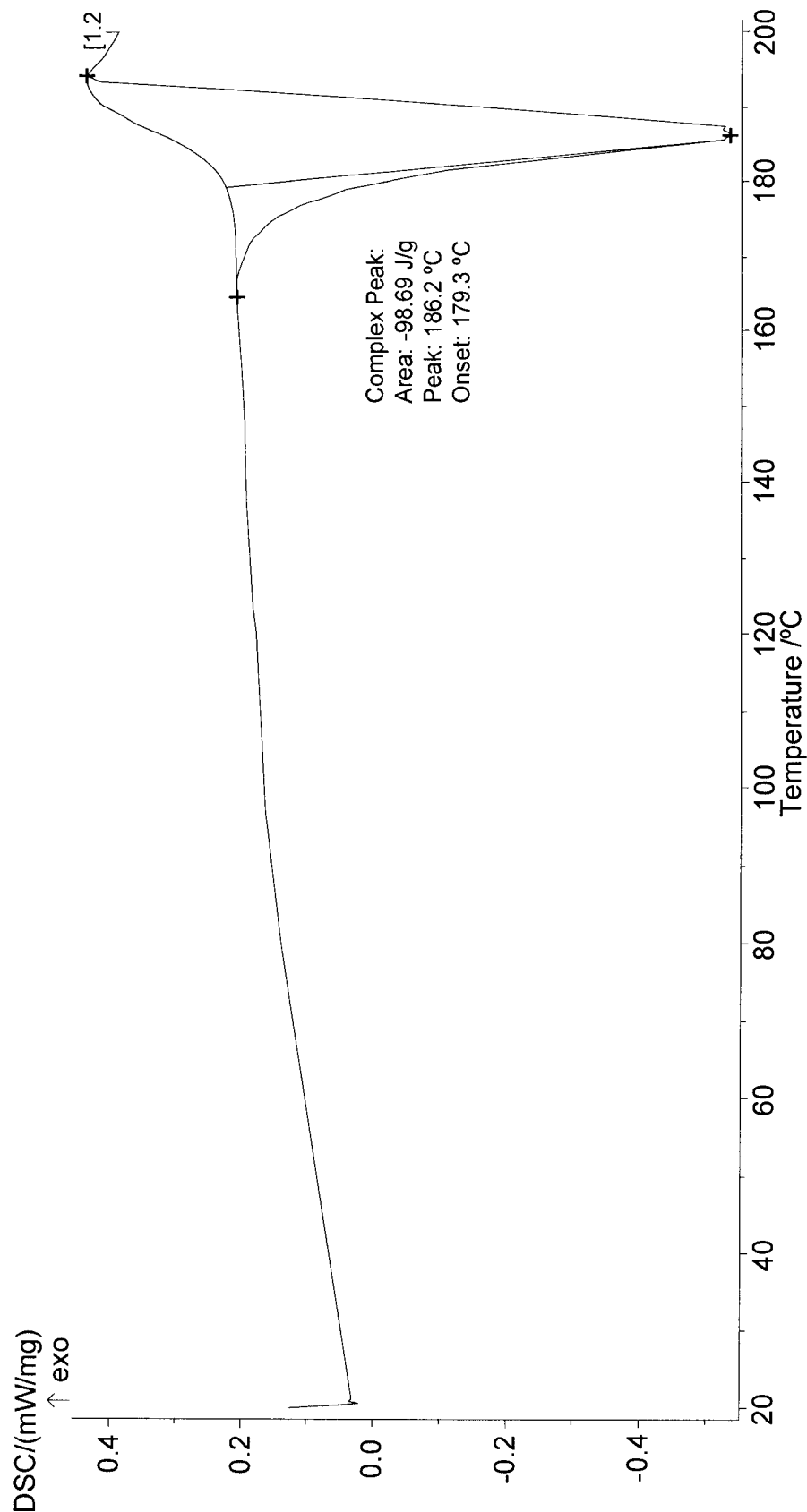
FIG. 16: DSC thermogram of polymorphic form III of compound 1
Figure 17:
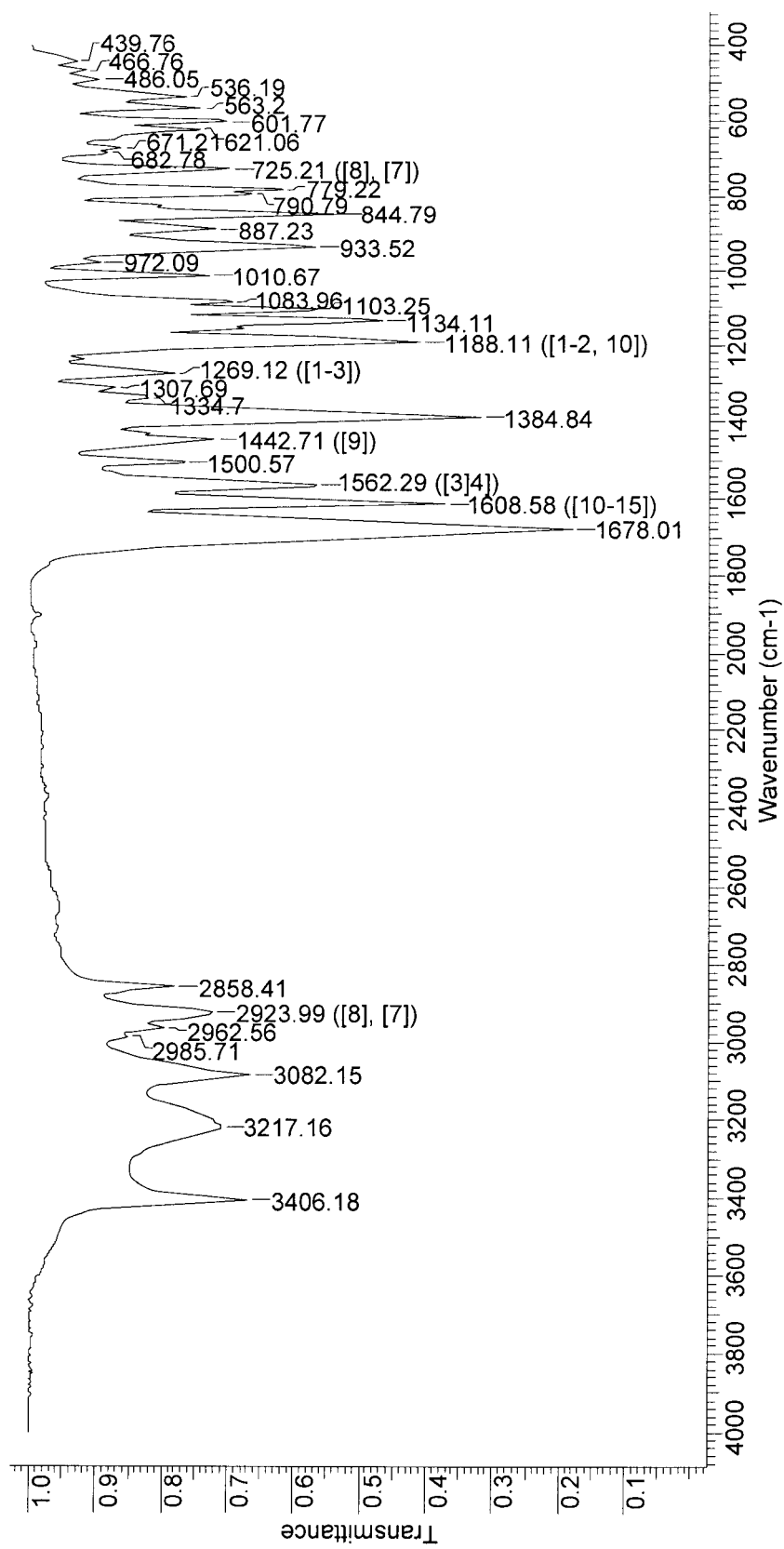
FIG. 17: IR spectrum of polymorphic form III of compound 1
Figure 18:
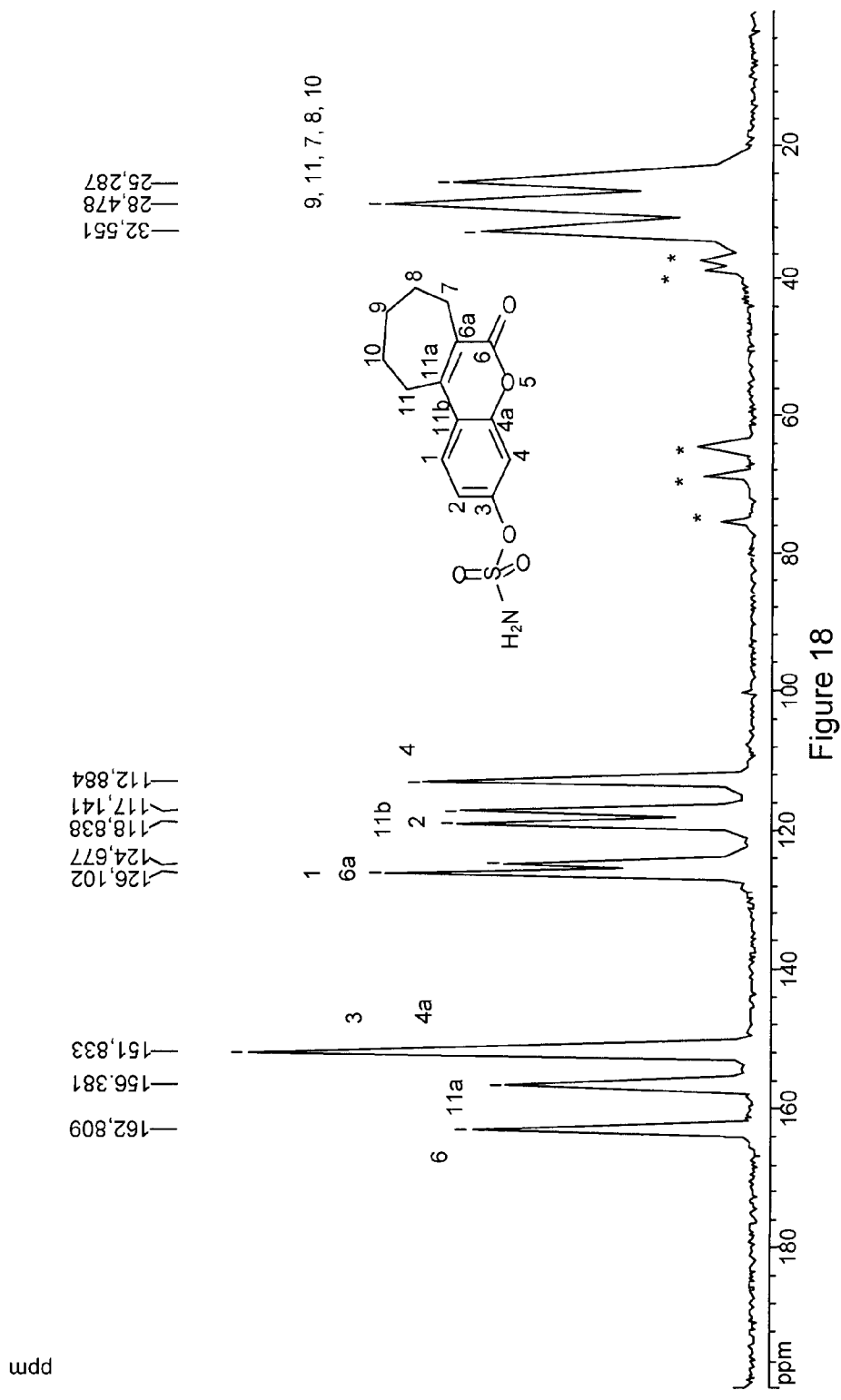
FIG. 18: NMR spectrum of the solid of polymorphic form III of compound 1
Figure 19:
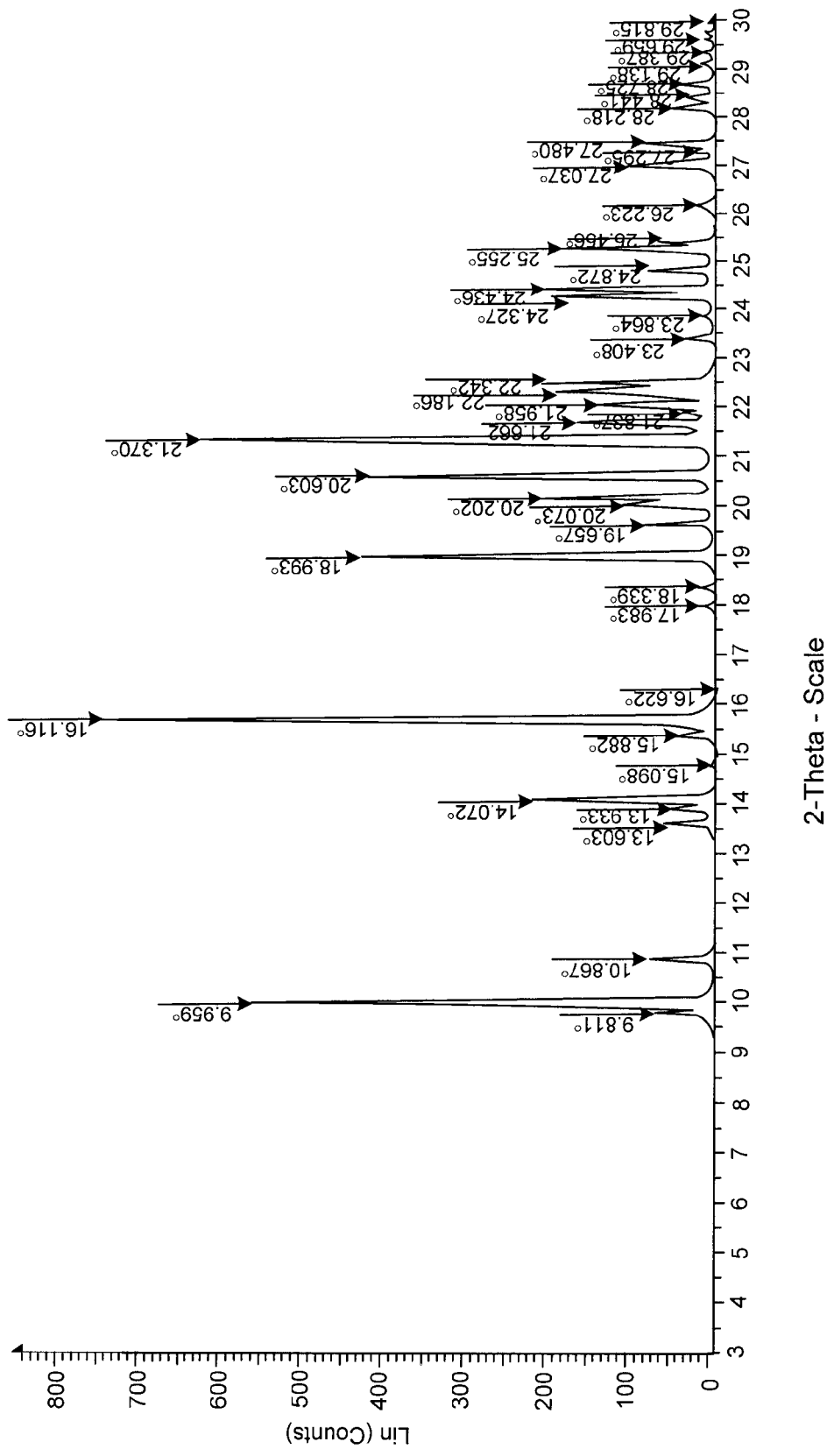
FIG. 19: calculated X-ray diffraction diagram of 1,4-dioxane hemisolvate of compound 1
Figure 20:
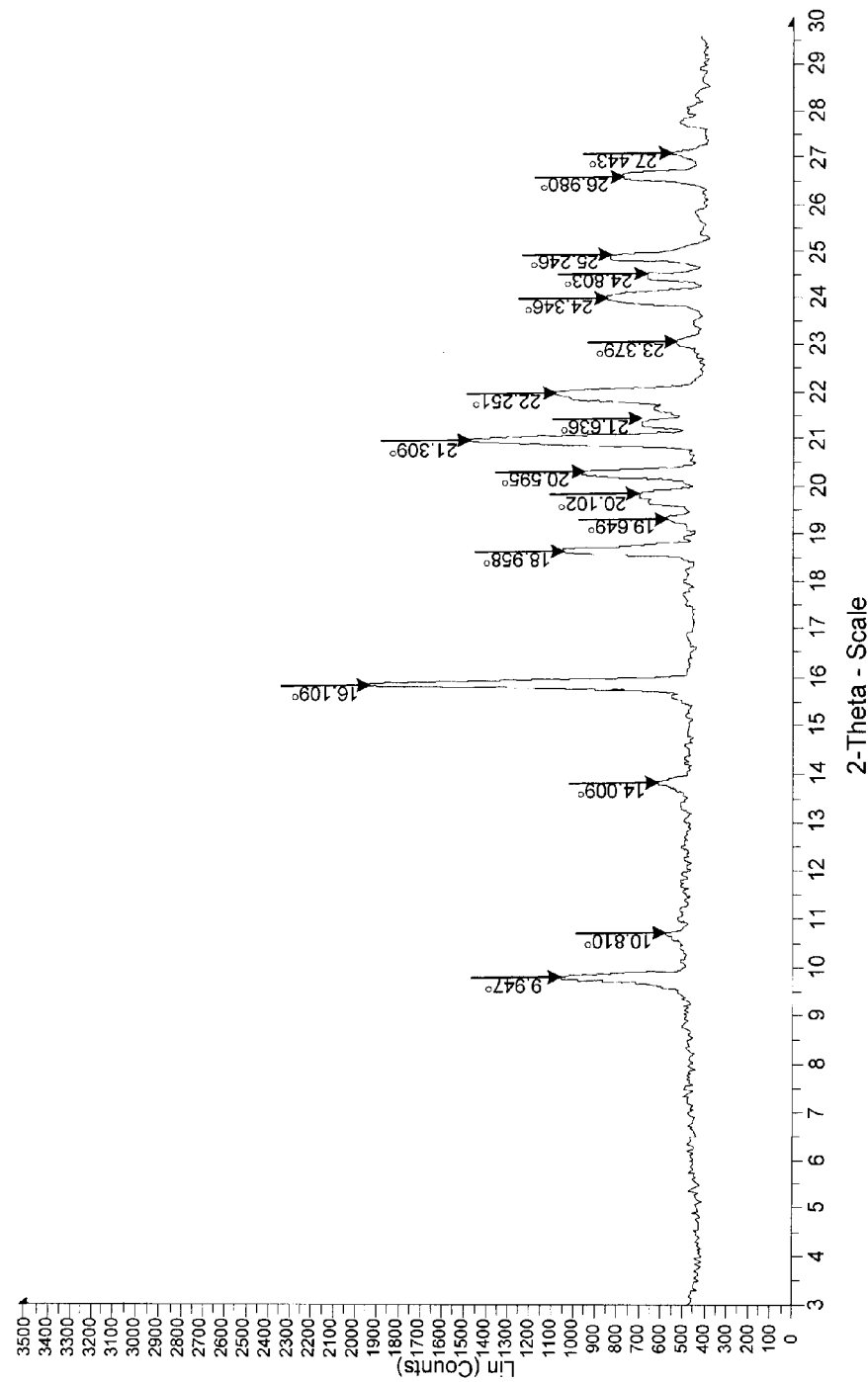
FIG. 20: experimental X-ray powder diffraction diagram of 1,4-dioxane hemisolvate of 5 compound 1
Figure 21:
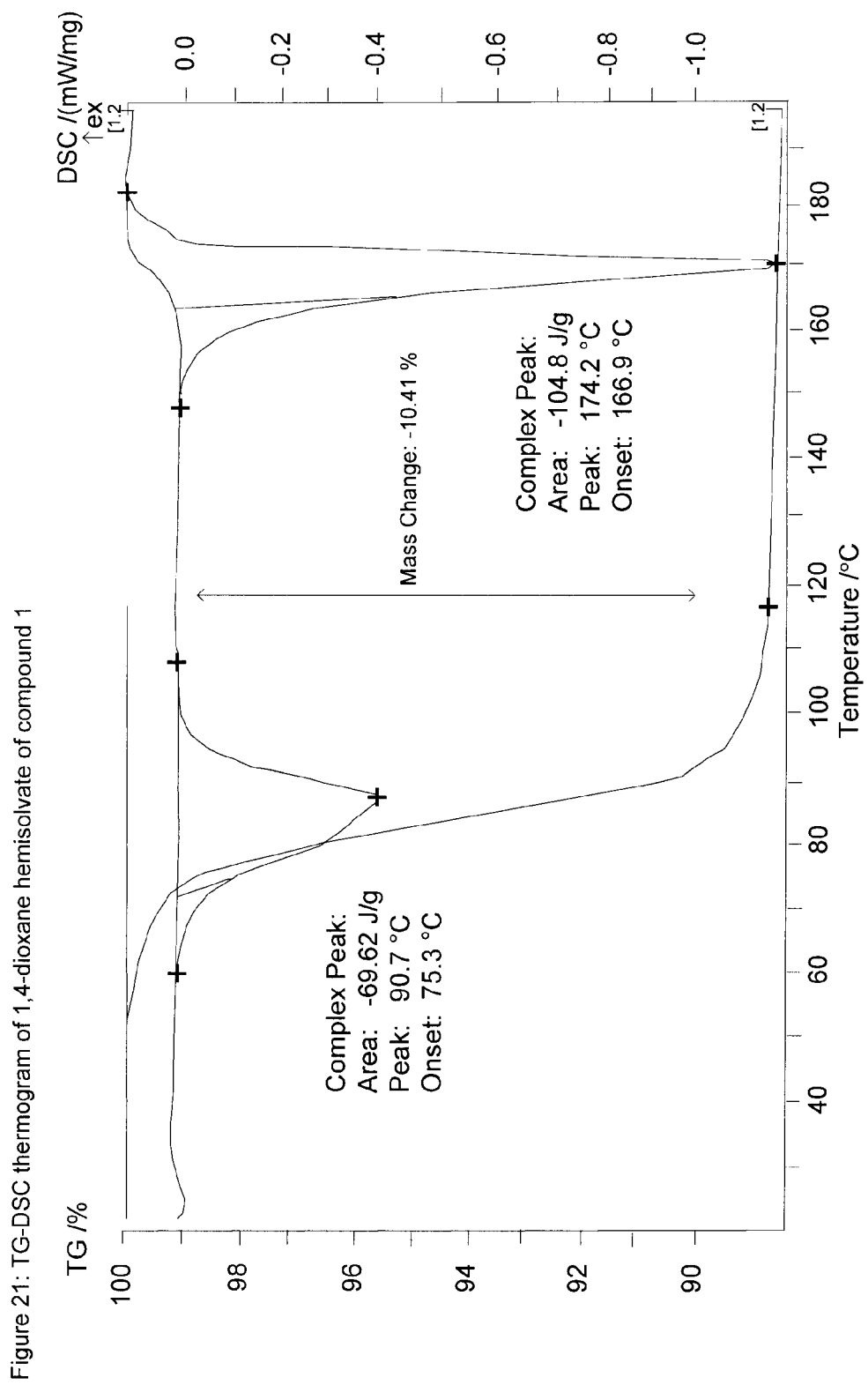
FIG. 21: TG-DSC thermogram of 1,4-dioxane hemisolvate of compound 1
Figure 22:
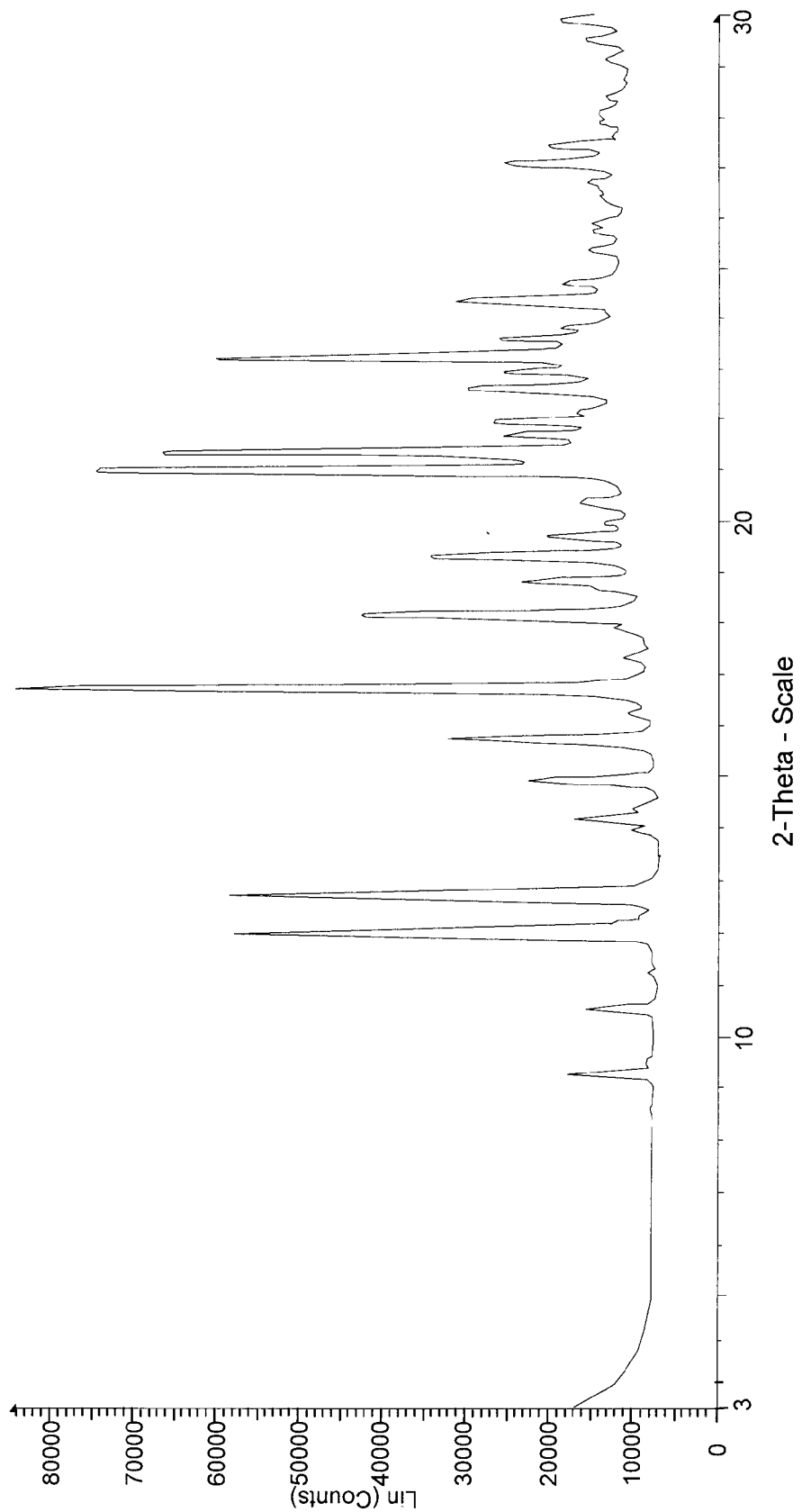
FIG. 22: experimental X-ray powder diffraction diagram of polymorphic form II of compound 1
Figure 23:
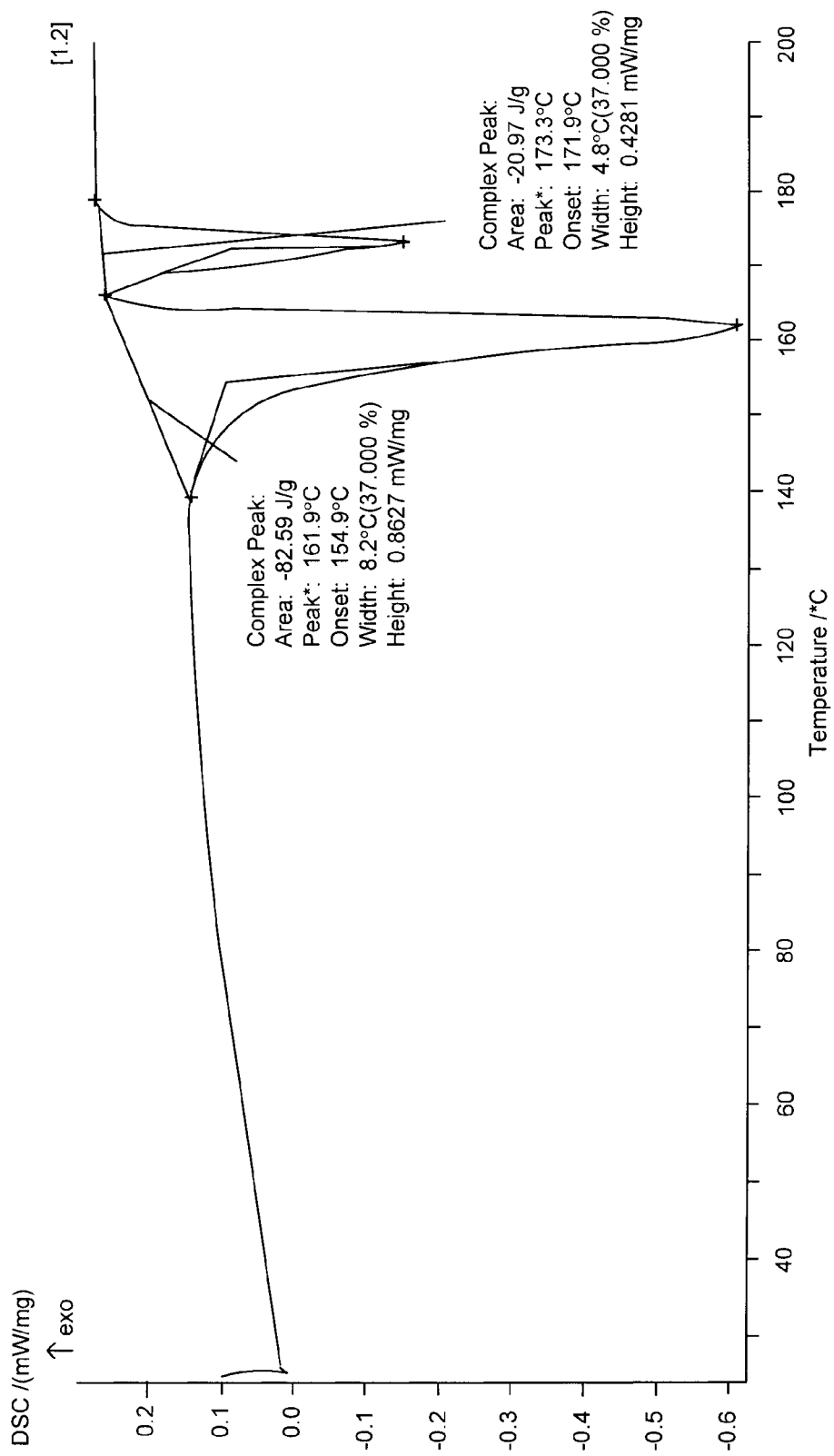
FIG. 23: DSC thermogram of polymorphic form II of compound 1
Figure 24:
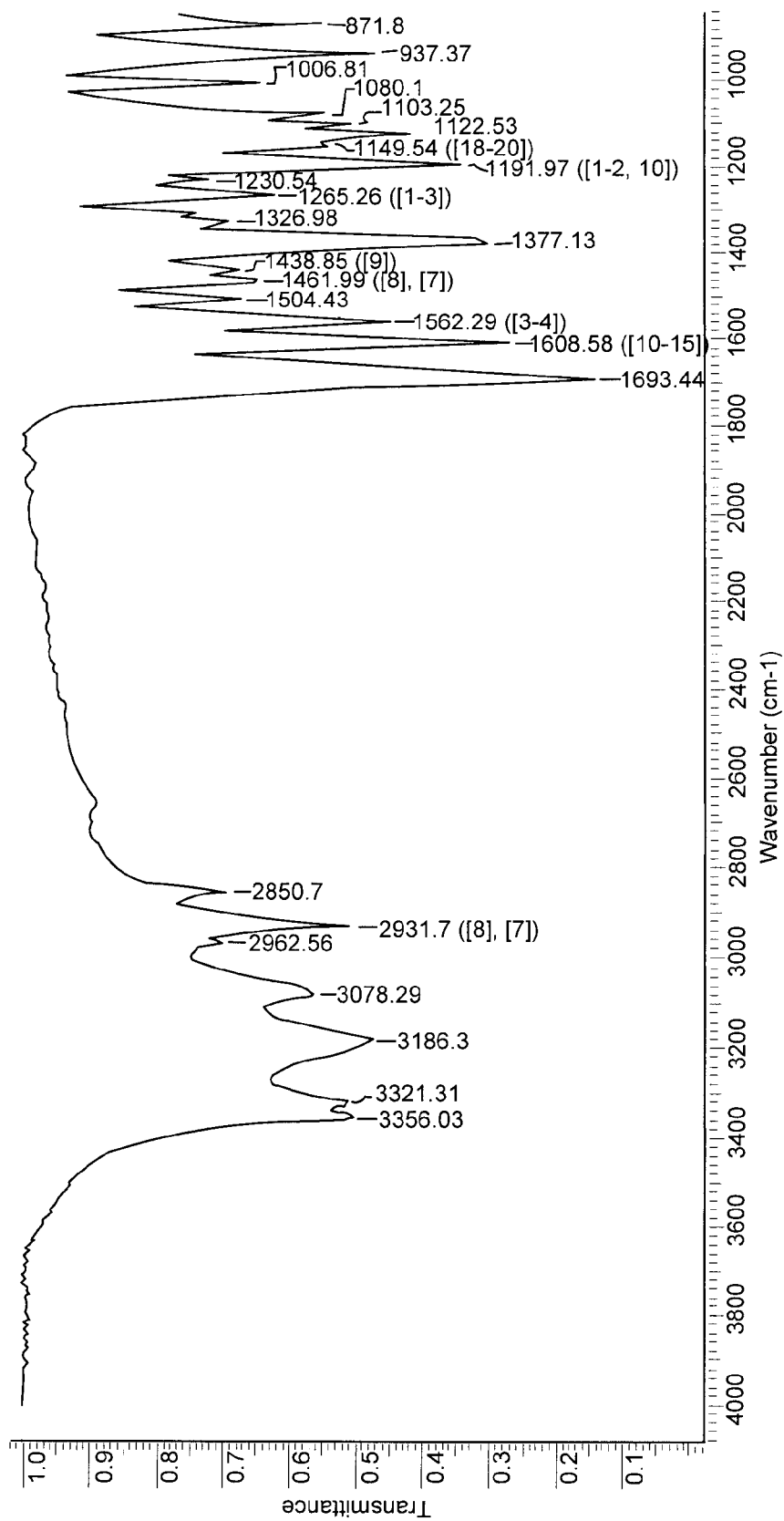
FIG. 24: IR spectrum of polymorphic form II of compound 1
Figure 25:
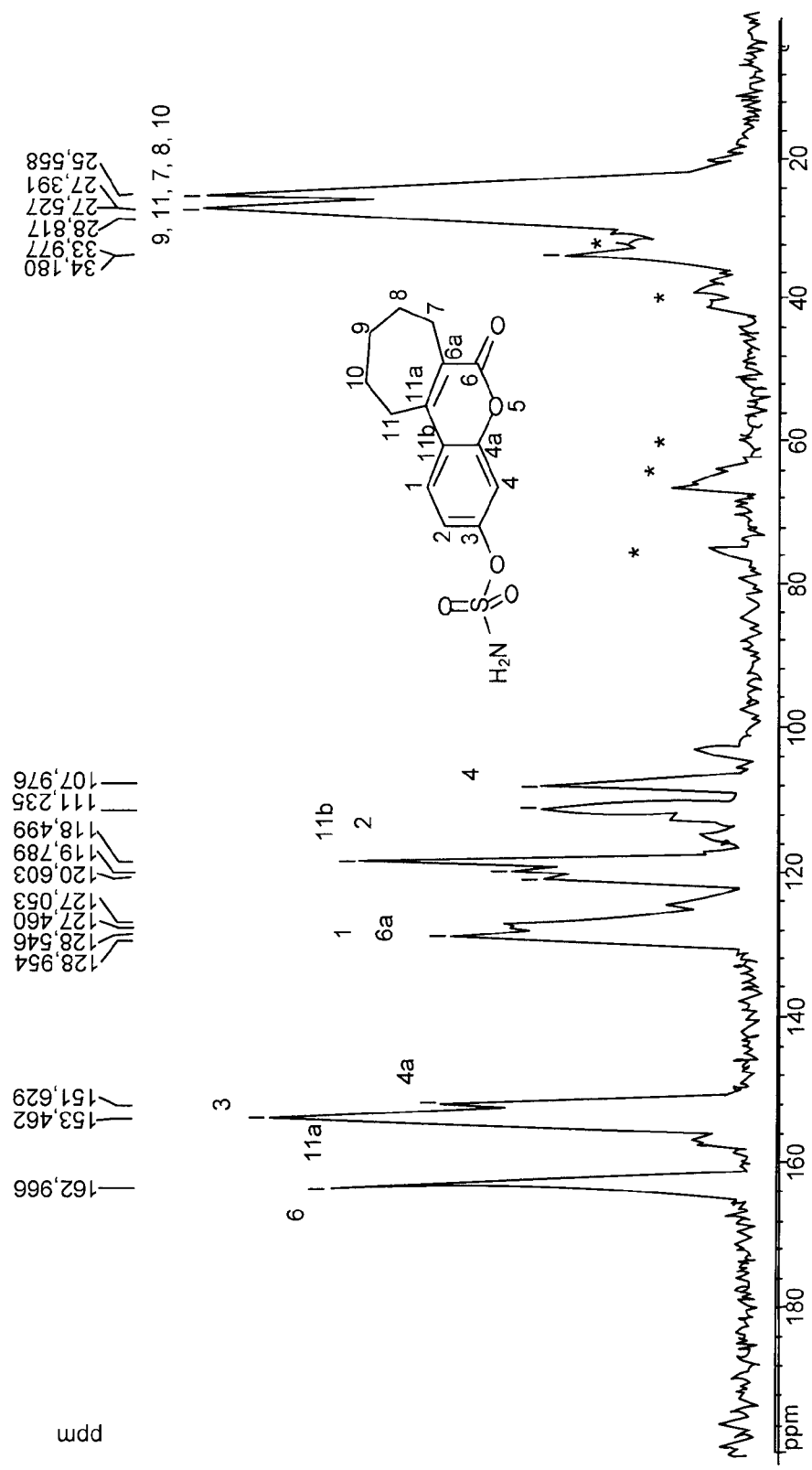
FIG. 25: NMR spectrum of the solid of polymorphic form II of compound 1
Figure 26:
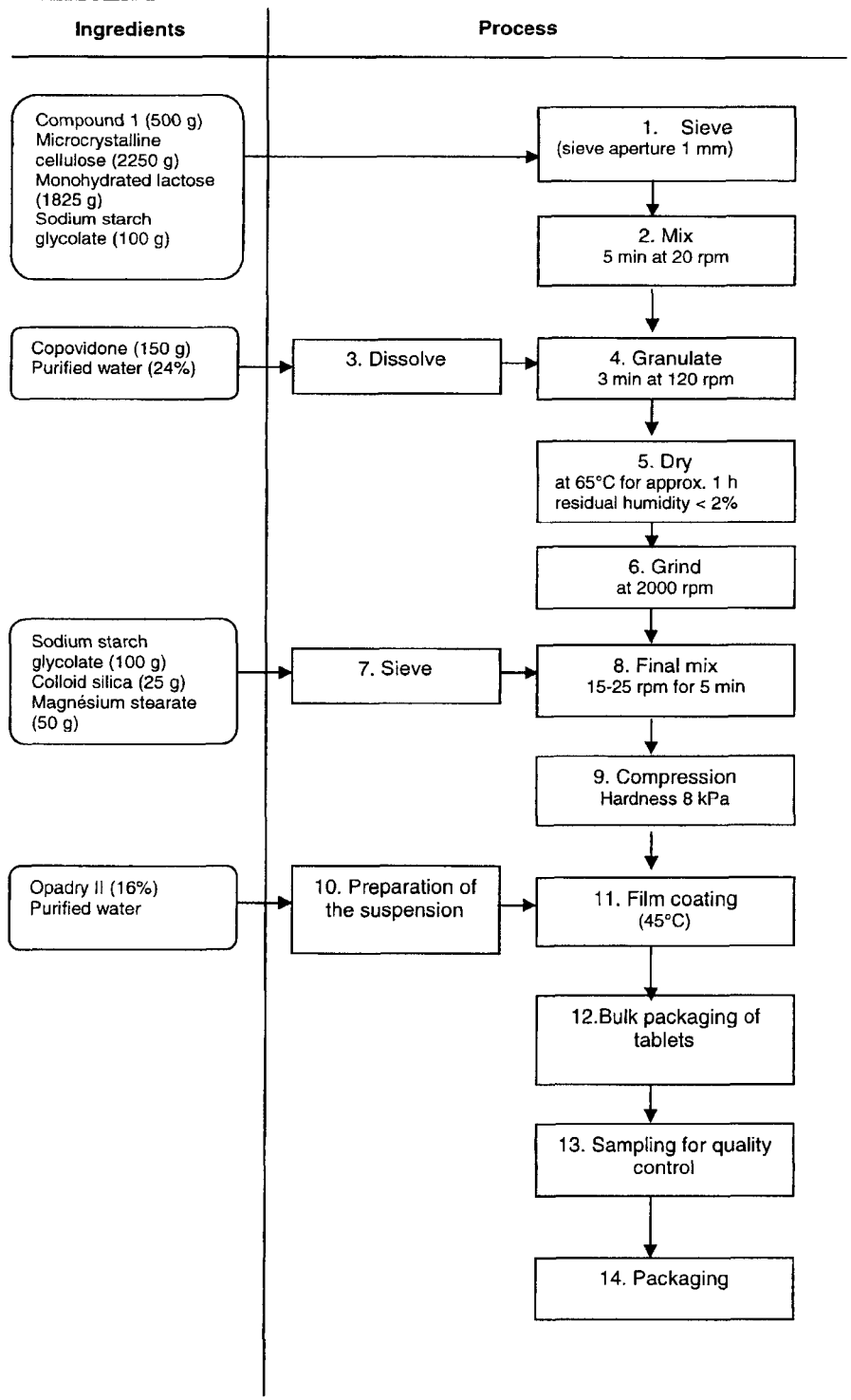
FIG. 26: shows a schematic for the preparation of a tablet form of the composition by wet granulation.

The spectrum of form II obtained by NMR of the solid exhibits the following characteristic peaks expressed in ppm to approximately ±0.2 ppm: 163.0; 154.5; 153.5; 151.6; 128.6; 118.5; 111.4; 108.2; 35; 25 (FIG. 16).

11. Physico-Chemical and Biological Properties 11.1 Conversion Experiments

The applicant has carried out conversion experiments between the different polymorphic forms of compound 1 which have shown that form III is the form which is stable at a high temperature (T>145° C.). This significant property makes it possible, by heating under vacuum, to eliminate traces of solvent (Polymorphism in the Pharmaceutical Industry, Wiley 2006, Ed Hilfiker; Wiley, ISBN: 978-3-527-31146-0). By returning to ambient temperature, form III of compound 1 remains unchanged, which also constitutes a prime advantage in the pharmaceutical industry 11.2 Chemical Stability A stability study was carried out at 150° C. between compound 1 of form III and the compound 1 described in patent EP 880514. This chemical stability of compound 1 is studied using HPLC The operating conditions of the HPLC method are the following:

column: Interchim UP3HDO-15XS, 150×4.6 mm,

| eluent A: | water | 2500 |
|---|---|---|
|  | trifluoroacetic acid | 0.5 |
| eluent B: | acetonitrile |  | gradient

| Time (min) | % A | % B |
|---|---|---|
| 0 | 80 | 20 |
| 22 | 5 | 95 |
| 24.2 | 80 | 20 | detection: 205 nm,
injection: 20 microliters,
temperature: 40° C.,
solution injected: 0.5 mg·mL$^{-1}$ (acetonitrile)

| | HPLC Purity | |
|---|---|---|
| Scores | Compound 1 patent EP 880514 | Compound 1 of form III |
| T0 | 99.6% | 99.4% |
| T2 hours at 150° C. | 7.3% | 41.2% |

The invention claimed is:

1. A polymorphic compound comprising 6-oxo-6,7,8,9,10,11 hexahydrocyclohepta[c]chromen-3-yl sulfamate, wherein the particle size is in the range of between 0.1 and 20 µm, and further wherein the compound comprises X-ray powder diffraction peaks that are ±0.1°2 theta of: 7.5; 10.9; 13.1; 17.7; and 19.0.

2. The compound according to claim 1, wherein the particle size is between 1 and 15 µm.

3. The compound according to claim 1, wherein the particle size is between 3 and 7 µm.

4. The compound according to claim 1, wherein the particle is 5 µm±1 µm.

5. The compound according to claim 1, wherein the compound comprises X-ray diffraction powder characteristic peaks that are ±0.1°2 theta of: 7.5, 10.9, 13.1, 15.0, 15.8, 17.0, 17.7, 19.0, and 22.5.

6. The compound according to claim 1, wherein the compound comprises X-ray diffraction powder characteristic peaks, produced after heating at 160° C. and back to temperature between 18 and 25° C., that are ±0.1°2 theta of: 7.5, 10.9, 13.1, 17.7, and 19.0, no additional peaks corresponding to the shape generated during heating to 160° C.

7. The compound according to claim 1, wherein the compound comprises a DSC heating rate of 5° C. min$^{-1}$; a melting endothermic peak at 170° C.±5° C.; and an endothermic peak at 180° C.±2° C. with the proviso that the peak at 180° C. is more than 10% of the enthalpy exchanged in the merger to 170° C.

8. A polymorphic compound comprising 6-oxo-6,7,8,9,10,11-hexahydrocyclohepta[c]chromen-3-yl sulfamate, wherein the compound comprises X-ray powder diffraction characteristic peaks that are ±0.1°2 theta of: 8.6, 11, 3, and 28.6.

9. The compound according to claim 8, wherein the compound comprises diffraction powder X-ray characteristic peaks that are ±0.1°2 theta of: 8.6, 11, 3; 12.0, 16.6, 20.9, 23.0, and 28.6.

10. The compound according to claim 8, wherein the compound comprises X-ray diffraction on single crystal unit cell parameters of the following:

| Cell Structure | Monoclinic |
| --- | --- |
| Space group | Cc (n° 9) |
| Cell parameter a | 11.327(1) Å |
| Cell parameter b | 20.489(2) Å |
| Cell parameter c | 7.870(1) Å |
| Cell parameter β | 131.55(1)° |
| Cell volume | 1366.9(2) Å$^3$ |
| Number of molecules per cell: Z | 4 |
| Calculated density | 1.53 g · cm$^{-3}$ | reduced coordinates (×10$^4$) and isotropic equivalent parameters of agitation (A2×10$^3$) as follows:

|  | X | y | z | U(eq) |
| --- | --- | --- | --- | --- |
| S(1) | 14534(1) | −1891(1) | 11571(1) | 41(1) |
| O(1) | 9079(2) | −569(1) | 5756(3) | 39(1) |
| O(2) | 13824(2) | −1450(1) | 12407(3) | 48(1) |
| O(3) | 6862(3) | −250(1) | 2510(3) | 57(1) |
| O(4) | 13672(3) | −1754(1) | 9246(3) | 62(1) |
| O(5) | 14551(3) | −2522(1) | 12277(5) | 73(1) |
| N(1) | 16289(3) | −1661(2) | 12982(5) | 55(1) |
| C(1) | 12910(3) | −904(1) | 11114(4) | 36(1) |
| C(2) | 11424(3) | −995(1) | 9041(4) | 37(1) |
| C(3) | 10541(3) | −449(1) | 7814(4) | 31(1) |
| C(4) | 11093(3) | 187(1) | 8587(4) | 32(1) |
| C(5) | 12593(3) | 249(1) | 10745(4) | 40(1) |
| C(6) | 13504(3) | −284(1) | 11996(4) | 42(1) |
| C(7) | 8111(3) | −78(1) | 4284(4) | 39(1) |
| C(8) | 8699(3) | 589(1) | 4976(4) | 37(1) |
| C(9) | 10098(3) | 718(1) | 7049(4) | 34(1) |
| C(10) | 10637(3) | 1421(1) | 7790(5) | 43(1) |
| C(11) | 9541(4) | 1809(1) | 7904(5) | 46(1) |
| C(12) | 8072(4) | 2076(1) | 5641(5) | 56(1) |
| C(13) | 6921(4) | 1568(2) | 3890(5) | 55(1) |
| C(14) | 7630(4) | 1111(1) | 3226(5) | 48(1). |

11. The compound according to claim 8, wherein the compound comprises a DSC at 5° C. min$^{-1}$ and an endothermic peak of melting 180° C.±2° C.

12. The compound according to claim 8, wherein the compound comprises infrared spectroscopy characteristic peaks that are ±5 cm$^{-1}$ of: 3406, 3217, 1678, 1011, and 563.

13. The compound according to claim 12, wherein said infrared spectroscopy comprises the characteristic peaks that are ±5 cm$^{-1}$ of: 3406, 3217, 3082, 2924, 1678, 1385, 1269, 1134, 1011, 934; 845, 601, 563, and 536.

14. The compound according to claim 1, wherein the compound does not comprise a DSC endothermic event between 140 and 155° C.

15. The compound according to claim 1, wherein the compound comprises infrared spectroscopy characteristic peaks that are ±5 cm$^{-1}$ of: 3310, 3167, 3059, 891, 798, 733, 679, and 455.

* * * * *